(12) United States Patent
Rylander et al.

(10) Patent No.: US 10,220,124 B2
(45) Date of Patent: Mar. 5, 2019

(54) FIBER ARRAY FOR OPTICAL IMAGING AND THERAPEUTICS

(75) Inventors: Christopher Rylander, Blacksburg, VA (US); Mehmet A. Kosoglu, Fairfax, VA (US); Robert L. Hood, Blacksburg, VA (US); John L. Robertson, Floyd, VA (US); John H. Rossmeisl, Blacksburg, VA (US); David C. Grant, Blacksburg, VA (US); Marissa N. Rylander, Blacksburg, VA (US)

(73) Assignee: VIRGINIA TECH INTELLECTUAL PROPERTIES, INC., Blacksburg, VA (US)

( * ) Notice: Subject to any disclaimer, the term of this patent is extended or adjusted under 35 U.S.C. 154(b) by 529 days.

(21) Appl. No.: 14/002,058

(22) PCT Filed: Feb. 28, 2012

(86) PCT No.: PCT/US2012/026968
§ 371 (c)(1),
(2), (4) Date: Aug. 28, 2013

(87) PCT Pub. No.: WO2012/154284
PCT Pub. Date: Nov. 15, 2012

(65) Prior Publication Data
US 2013/0338627 A1 Dec. 19, 2013

Related U.S. Application Data

(63) Continuation-in-part of application No. 13/203,800, filed as application No. PCT/US2010/025809 on Mar. 1, 2010.
(Continued)

(51) Int. Cl.
*A61M 1/00* (2006.01)
*A61M 5/158* (2006.01)
(Continued)

(52) U.S. Cl.
CPC ............. *A61M 1/008* (2013.01); *A61B 18/20* (2013.01); *A61M 5/158* (2013.01); *A61N 5/062* (2013.01);
(Continued)

(58) Field of Classification Search
CPC ....... A61M 1/008; A61M 5/158; A61B 18/20; A61N 5/062
(Continued)

(56) References Cited

U.S. PATENT DOCUMENTS 5,483,958 A 1/1996 Merberg et al.
6,148,223 A 11/2000 Davis et al.
(Continued)

FOREIGN PATENT DOCUMENTS

KR 100963395 6/2010
KR 100963395 B1 6/2010
(Continued)

OTHER PUBLICATIONS

Co-pending U.S. Appl. No. 13/203,800 Official Notice of Allowance dated May 5, 2014, 10 pages.
(Continued)

*Primary Examiner* — Carl H Layno
*Assistant Examiner* — Dacheng Xie
(74) *Attorney, Agent, or Firm* — New River Valley IP Law, PC; Michele L. Mayberry

(57) ABSTRACT

The present invention relates to the field of optical imaging and therapeutics. More particularly, embodiments of the present invention provide minimally-invasive Fiberoptic Microneedle Devices (FMDs) for light-based therapeutics, which physically penetrate tissue and deliver light directly into the target area below the skin surface. Embodiments of the invention enable depth-selective and deep photothermal therapeutics and include methods of treating cancer, meth- (Continued)

ods of re-shaping or removing adipose tissue, and methods of delivering drugs or co-delivering drugs and energy to selected tissue.

13 Claims, 51 Drawing Sheets

Related U.S. Application Data

(60) Provisional application No. 61/546,090, filed on Oct. 12, 2011, provisional application No. 61/447,380, filed on Feb. 28, 2011, provisional application No. 61/156,273, filed on Feb. 27, 2009.

(51) Int. Cl.
  *A61B 18/20* (2006.01)
  *A61B 18/22* (2006.01)
  *A61B 18/00* (2006.01)
  *A61N 5/06* (2006.01)

(52) U.S. Cl.
  CPC ..... *A61B 18/22* (2013.01); *A61B 2018/00452* (2013.01); *A61B 2018/00464* (2013.01); *A61B 2018/00476* (2013.01); *A61B 2018/2005* (2013.01); *A61B 2018/208* (2013.01); *A61M 2202/08* (2013.01); *A61N 2005/063* (2013.01); *A61N 2005/0612* (2013.01); *F04C 2270/0421* (2013.01)

(58) Field of Classification Search
  USPC ............. 600/473–478; 606/2–19; 607/86–94
  See application file for complete search history.

(56) References Cited

U.S. PATENT DOCUMENTS

| | | | |
|---|---|---|---|
| 6,343,174 B1 * | 1/2002 | Neuberger ............. | A61B 18/22 385/117 |
| 6,355,054 B1 | 3/2002 | Neuberger | |
| 6,564,087 B1 | 5/2003 | Pitris et al. | |
| 7,027,478 B2 | 4/2006 | Ackley | |
| 8,681,421 B1 * | 3/2014 | Pepper ................ | H01S 3/06708 359/341.1 |
| 2003/0095582 A1 | 5/2003 | Ackley | |
| 2004/0249360 A1 * | 12/2004 | Spehalski ......... | A61M 25/0133 604/523 |
| 2005/0137531 A1 | 6/2005 | Prausnitz et al. | |
| 2006/0276871 A1 * | 12/2006 | Lamson .................... | A61F 2/82 623/1.11 |
| 2007/0032845 A1 | 2/2007 | Neuberger | |
| 2007/0129713 A1 | 6/2007 | Weber | |
| 2008/0009751 A1 * | 1/2008 | Berndt ................. | A61B 5/0075 600/478 |
| 2008/0140023 A1 | 6/2008 | Mcmillan | |
| 2008/0269735 A1 * | 10/2008 | Vila Echague ........ | A61B 18/20 606/15 |
| 2009/0192503 A1 * | 7/2009 | Epshtein ................ | A61B 18/24 606/15 |
| 2011/0125077 A1 * | 5/2011 | Denison ............... | A61N 5/0601 604/20 |
| 2011/0313298 A1 * | 12/2011 | Rylander ............. | A61B 5/0059 600/478 |
| 2012/0022504 A1 * | 1/2012 | Epshtein ............ | A61B 18/1477 604/542 |
| 2013/0066300 A1 | 3/2013 | Rhee et al. | |

FOREIGN PATENT DOCUMENTS

| | | |
|---|---|---|
| WO | 0250584 A2 | 6/2002 |
| WO | 2009042268 A1 | 4/2009 |
| WO | 2010099548 A | 9/2010 |
| WO | 2010102246 A1 | 9/2010 |

OTHER PUBLICATIONS

Co-pending U.S. Appl. No. 13/203,800, Final Office Action dated Nov. 8, 2013, 10 pages.
Co-pending U.S. Appl. No. 13/203,800, Non-Final Office Action dated Apr. 1, 2013, 10 pages.
Co-pending U.S. Appl. No. 13/203,800, Preliminary Amendment dated Aug. 29, 2011 filed, 8 pages.
Co-pending U.S. Appl. No. 13/203,800, Response to Final Office Action filed Jan. 9, 2014, 13 pages.
Co-pending U.S. Appl. No. 13/203,800, Response to Non-Final Office Action filed Jul. 29, 2013, 10 pages.
Co-pending U.S. Appl. No. 13/203,800, Supplemental Amendment filed Oct. 8, 2013, 7 pages.
Co-Pending Application EP 12781846.6, European Search Report dated Aug. 13, 2014, and Communication pursuant to Rules 70(2) and 70a(2) EPC dated Sep. 11, 2014, 7 pages.
Co-Pending U.S. Appl. No. 13/203,800, Issued as U.S. Pat. No. 8,798,722 on Aug. 5, 2014, 37 pages.
Anderson, R.R. and J.A. Parrish, "Selective Photothermolysis: Precise Microsurgery by Selective Absorption of Pulsed Radiation," Science, 1983, 220(4596): p. 524-527.
Anderson, R.R. and J.A. Parrish, "The Optics of Human-Skin," Journal of Investigative Dermatology, 1981, 77(1): p. 13-19.
Campos, V.B., et al., "Ruby laser hair removal: Evaluation of long-term efficacy and side effects. Lasers in Surgery and Medicine," 2000, 26(2): p. 177-185.
Co-Pending U.S. Appl. No. 13/203,800, filed Aug. 29, 2011, published as US 2011/0313298 on Dec. 22, 2011.
Co-Pending Application No. PCT/US10/25809, filed Mar. 1, 2010, published as WO2010/099548 on Dec. Sep. 2, 2010.
Davis, S.P., et al., "Insertion of microneedles into skin: measurement and prediction of insertion force and needle fracture force," Journal of Biomechanics, 2004, 37(8): p. 1155-1163.
Grossman, M.C., et al., "Damage to hair follicles by normal-mode ruby laser pulses," Journal of the American Academy of Dermatology, 1996, 35(6): p. 889-894.
Hood RL, Kosoglu MA, Parker M, Rylander CG, Effects of Microneedle Design Parameters on Hydraulic Resistance, J. Med Devices 2011; 5(3).
Hruby, G.W., et al., "Transurethral Bladder Cryoablation in the Porcine Model." Journal of Urology, 70 (2), 2007, pp. 391-395.
International Application No. PCT/US10/25809, International Preliminary Report on Patentability, dated Aug. 30, 2011.
International Application No. PCT/US10/25809, International Search Report, dated Oct. 14, 2010.
International Application No. PCT/US12/26968, International Preliminary Report on Patentability, dated Sep. 3, 2013, 8 pages.
International Application No. PCT/US12/26968, International Search Report and Written Opinion, dated Nov. 26, 2012.
Johnson, D.E., "Use of the Holmium: Yag (Ho: Yag) Laser for Treatment of Superficial Bladder Carcinoma." Lasers in Surgery and Medicine, 1994, 14(3): p. 213-218.
Kaushik, S., et al., "Lack of Pain Associated with Microfabricated Microneedles," Anesthesia and Analgesia, 2001, 92 (2): p. 502-504.
Khumpuang, S., R. Maeda, and S. Sugiyama, "Design and fabrication of a coupled microneedle array and insertion guide array for safe penetration through skin," in Micromechatronics and Human Science, 2003, MHS 2003: Proceedings of 2003 International Symposium.
Kosoglu Ma, Hood RL, Chen Y, Xu Y, Rylander MN, Rylander CG, "Fiber Optic Microneedles for Transdermal Light Delivery: Ex Vivo Porcine Skin Penetration Experiments," J. Biomech. Engr. 2010; 132(9):091014.
Kosoglu MA, Hood RL, Rossmeisl JH, Grant DC, Xu Y, Robertson JL, Rylander MN, Rylander CG, Fiberoptic Microneedles: Novel Optical Diffusers for Interstitial Delivery of Therapeutic Light, Laser Surg Med 2011; 43(9):914-920.
Li, Xingde, et al., Imaging needle for optical coherence tomography. Optics Letters. vol. 25, No. 20. Oct. 15, 2000.
Meyer, W., R. Schwarz, and K. Neurand, "The skin of domestic mammals as a model for the human skin, with special reference to the domestic pig," Curr Probl Dermatol, 1978, 7: p. 39-52.

(56) References Cited

OTHER PUBLICATIONS

Mumtaz, H., et al. 1996, "Laser Therapy for Breast Cancer: Mr Imaging and Histopathologic Correlation," Radiology, 200(3), pp. 651-658.
Nanni, C.A. and T.S. Alster, "Long-pulsed alexandrite laser-assisted hair removal at 5, 10, and 20 millisecond pulse durations," Lasers in Surgery and Medicine, 1999, 24(5): p. 332-337.
Prudhomme, M., et al., 1996, "Interstitial Diode Laser Hyperthermia in the Treatment of Subcutaneous Tumor," Lasers in Surgery and Medicine, 19(4), pp. 445-450.
Raghavan, R., et al., "Convection-enhanced delivery of therapeutics for brain disease, and its optimization." Neurosurg Focus, 2006. 20(4): p. E12.
Ramasubramanian, M.K., et al., "Mechanics of a mosquito bite with applications to microneedle design," Bioinspiration & Biomimetics, 2008, 3(4).
Ribeiro, J.M.C. and I.M.B. Francischetti, "Role of arthropod saliva in blood feeding: Sialome and post-sialome perspectives," Annual Review of Entomology, 2003, 48: pp. 73-88.
Robinson, D. S., et al., 1998, "Interstitial Laser Hyperthermia Model Development for Minimally Invasive Therapy of Breast Carcinoma," Journal of the American College of Surgeons, 186(3), pp. 284-292.
Roxhed, N., et al., 2007, "Penetration-Enhanced Ultrasharp Microneedles and Prediction on Skin Interaction for Efficient Transdermal Drug Delivery," Journal of Microelectromechanical Systems, 16(6), pp. 1429-1440.
Shergold, O. A., and Fleck, N. A., 2005, "Experimental Investigation into the Deep Penetration of Soft Solids by Sharp and Blunt Punches, with Application to the Piercing of Skin," Journal of Biomechanical Engineering—Transactions of the Asme, 127(5), pp. 838-848.
Stupp, R., et al., "Radiotherapy plus concomitant and adjuvant temozolomide for glioblastoma." N Engl J Med, 2005. 352(10): p. 987-96.
Syed, H.A., et al., "Holmium: YAG Laser Treatment of Recurrent Superficial Bladder Carcinoma: Initial Clinical Experience." Journal of Endourology, 2001, 15(6): p. 625-627.
Utzinger, U. and Richards-Kortum, R. R., 2003, "Fiber Optic Probes for Biomedical Optical Spectroscopy," Journal of Biomedical Optics, 8(1), pp. 121-147.
Vandergrift, W.A., et al., "Convection-enhanced delivery of immunotoxins and radioisotopes for treatment of malignant gliomas." Neurosurg Focus, 2006. 20(4): p. E13.
Wang, C.M., Wang C. Y., Reddy, J. N., "Exact Solutions for Buckling of Structural Members," CRC Series in Computational Mechanics and Applied Analysis, 2004, pp. 35-40.
Yamaguchi, S., et al., "Efficient Nd:YAG laser end pumped by a high-power multistripe laser-diode bar with multiprism array coupling.," Applied Optics, 1996, 35(9): p. 1430-1435.

* cited by examiner

Mosquito Fascicle Surrounded by Labium

Microneedle Penetration of Ex Vivo Porcine Skin at 3A) 0 mm; 3B) 0.5 mm; and 3C) 1 mm Insertion Distance.

Ferrule Array Device: (*left*) in contact with skin, and (*right*) compressed against skin, causing fiber tapers to penetrate skin Critical Buckling Force With and Without Support and the Range of Forces for Insertion into Skin Fiberoptic Microneedle Device (FMD) Schematic Illustration of: (left) device using compression between two rigid plates, and (right) device using layered elastomeric ferrule Laser Ablation of a Gelatin Phantom Using 1064 nm light (.1 W) for a) 0s and b) 3min.

Skin Anatomy, and Fluence Distribution with Surface Delivery Compared to Microneedle Delivery Fiberoptic Microneedle (length= 3mm, average diameter= 125 micron) Penetrating 2 mm Thick Pig Skin Sample.

Fiberoptic Microneedle Device (FMD) Demonstrating Insertion of Microneedles into Skin Figure 19: a) Overview of the FMD setup b) Close-up image of the device Polished Microneedle Delivering Light in Air a) Brightfield microscopy image of optical fiber before etching;
b) Brightfield microscopy image of optical fiber after etching; and
c) Color microscopy image of red laser delivery by the etched fiber.

a) Vacuum chamber, ferrule, and the fiberoptic microneedle; b) Fiberoptic microneedle penetrating 2 mm thick pig skin Fig. 23. Schematic of FMD with multifunctional arborizing, light guiding, and drug delivery fibers for treatment of MGs.

Fig. 24. Light delivery through a customized microneedle surface.

Figure 25. Treatment planning/guidance strategy involving MR imaging and computational modeling to allow the clinician to adjust FMD parameters *during* treatment.

Figure 26: Experimental setup for FMD infusion of SWNHs into an isolated porcine bladder. Bladder has been bisected with the urothelium exposed.

Figure 27: FMD design concept for bladder treatment. Light-guiding HCFs permit simultaneous co-delivery of laser light and fluid agents, enabling a combinatorial treatment.

Figure 28: Image of beveled microneedle at the tip of a HCF. Water is visible inside the hollow bore.

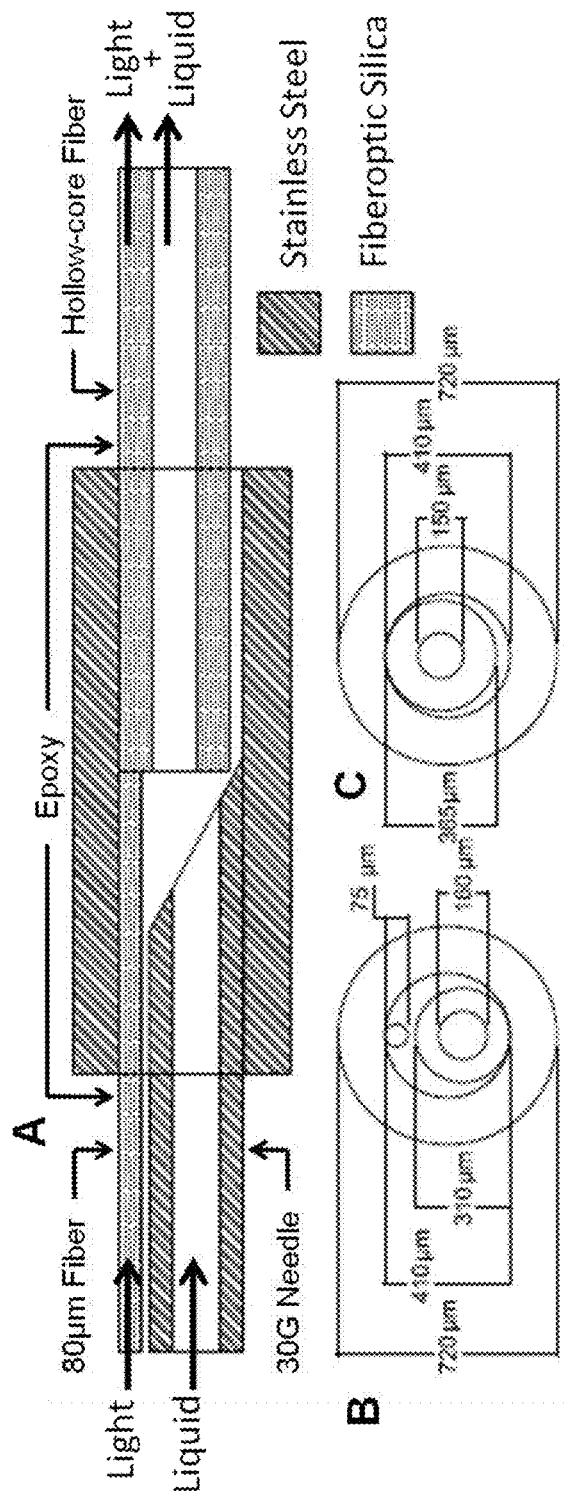

Figure 29: Schematic of FMD co-delivery couple design. A) Cut-away of the co-delivery couple showing the alignment of the light conducting fibers and position of the fluid input, B) cross-section of the input of the couple, exhibiting the position of the light and fluid inputs, and C) cross-section of the output of the couple, exhibiting the position of the codelivery HCF.

FIGS. 29A-C

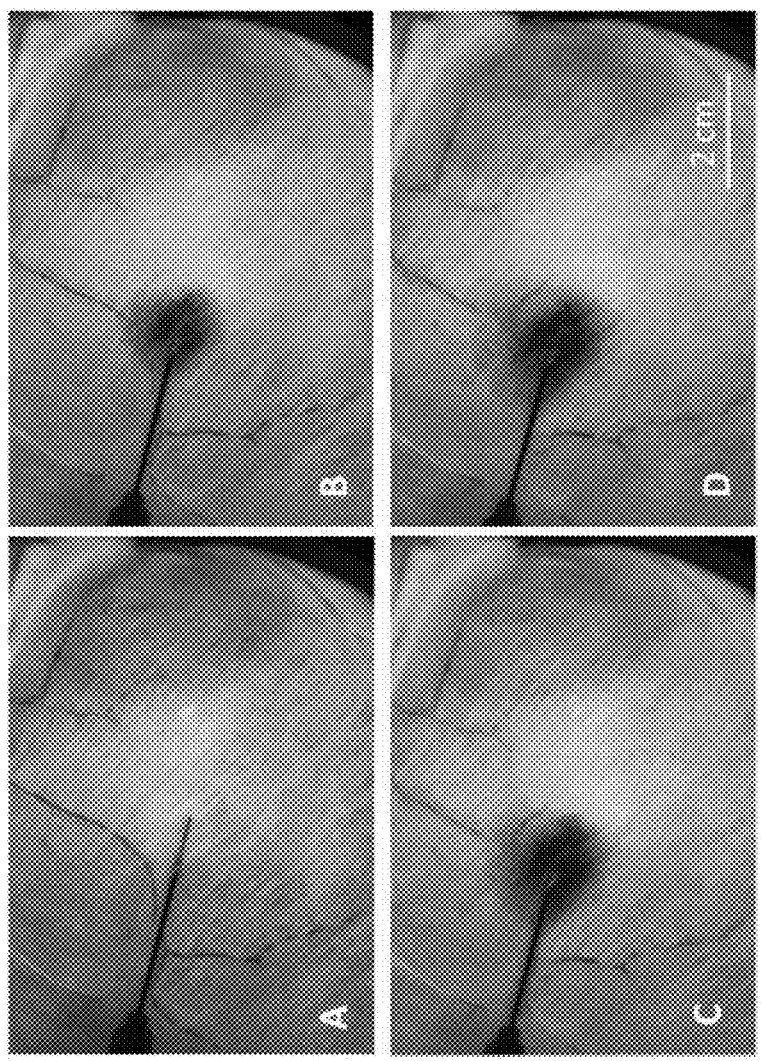
Figure 30: SWNH infusion through HCF into an ex vivo porcine bladder wall. A) t = 0 min, area = 0 B) t = 4 min, area = 1.5 cm2 C) t = 8 min, area = 2.6 cm2 D) t = 12 min, 3.2 cm2
FIGS. 30A-D Figure 31: Area versus time plot of data from image analysis of photographs of the serosa taken every 30 s during SWNH infusion into the bladder wall.

Figure 32: Two sets of infusions, located proximal to the neck and apex of the bladder, respectively, are labeled with their infusion times in minutes.

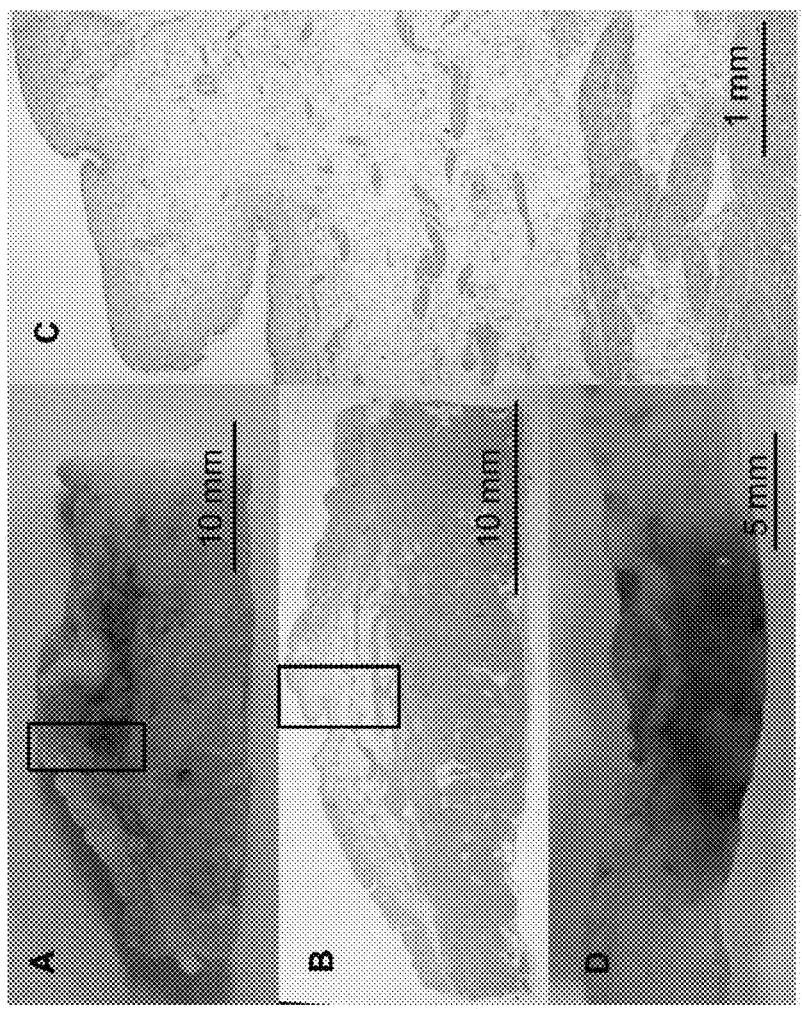

Figure 33: (A) Gross section of formalin-fixed bladder wall following 5 minute infusion into thicker/apical region of uninflated bladder. (B) Histological section cut directly from the gross section (A). (C) Close view of the stained section (location denoted by black boxes in (A) and (B)). (D) Gross section of fixed bladder wall following 10 minute infusion into inflated bladder.

FIGS. 33A-D

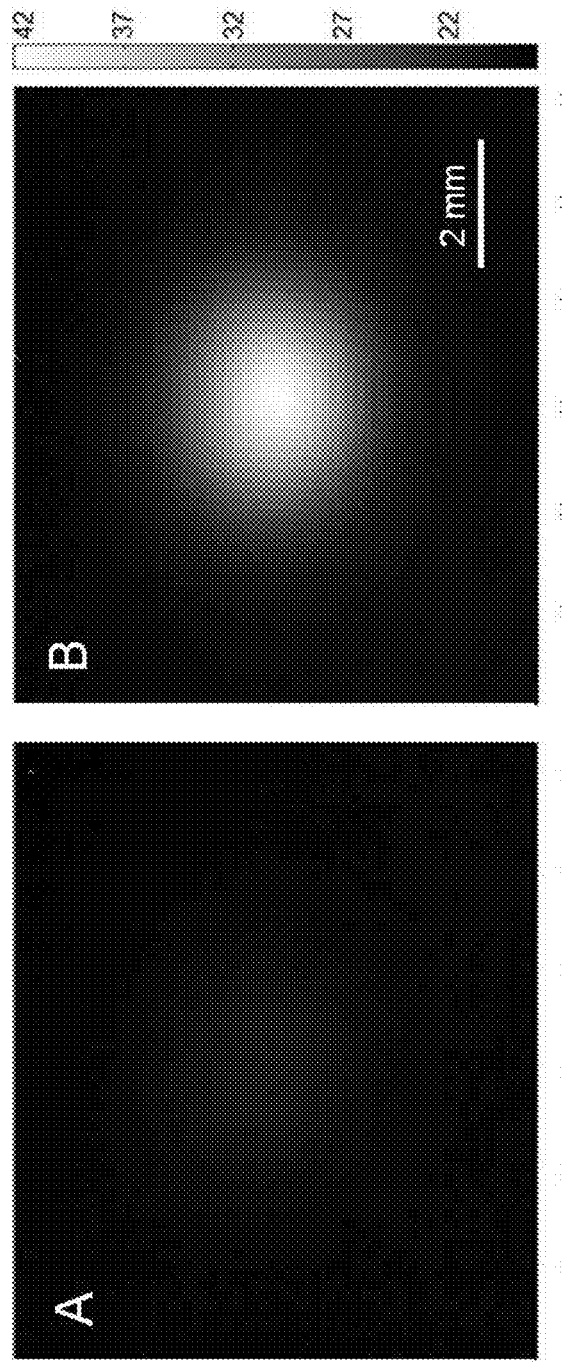
Figure 34: Thermographs of laser heating perfused bladder tissue in regions: (A) without SWNHs and (B) with SWNHs. The color scale depicts temperature in Celsius.
FIGS. 34A-B Figure 35: Thermograph of laser irradiation on SWNH perfused bladder wall with a 1.5 cm beam width. The highest temperature correlates with the laser/SWNH overlap.

Figure 36: Irradiation from light-guiding, hollow-core microneedle after delivering SWNHs into the inflated bladder wall. (A) photograph showing microneedle position, (B) thermograph of non-infused control, and C)thermograph of SWNH perfused tissue.

FIGS. 36A-C

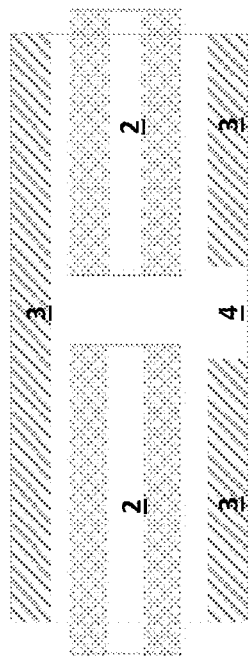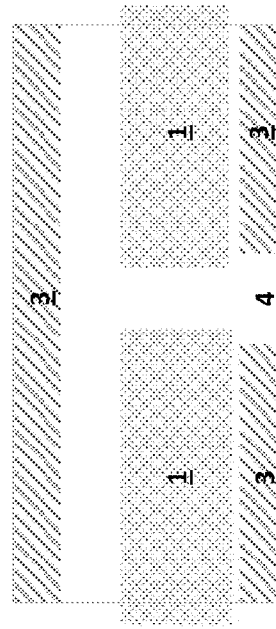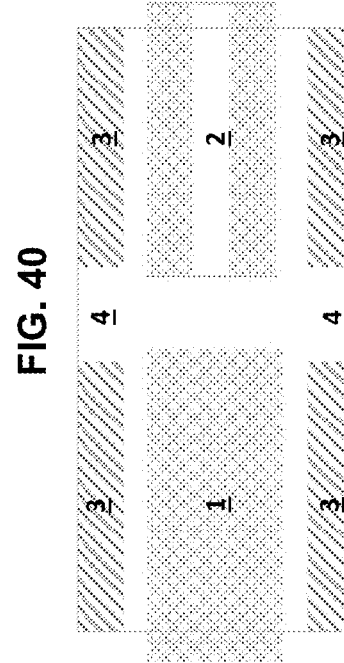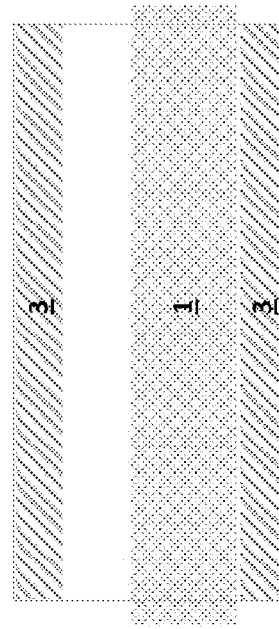
FIGS. 37-42

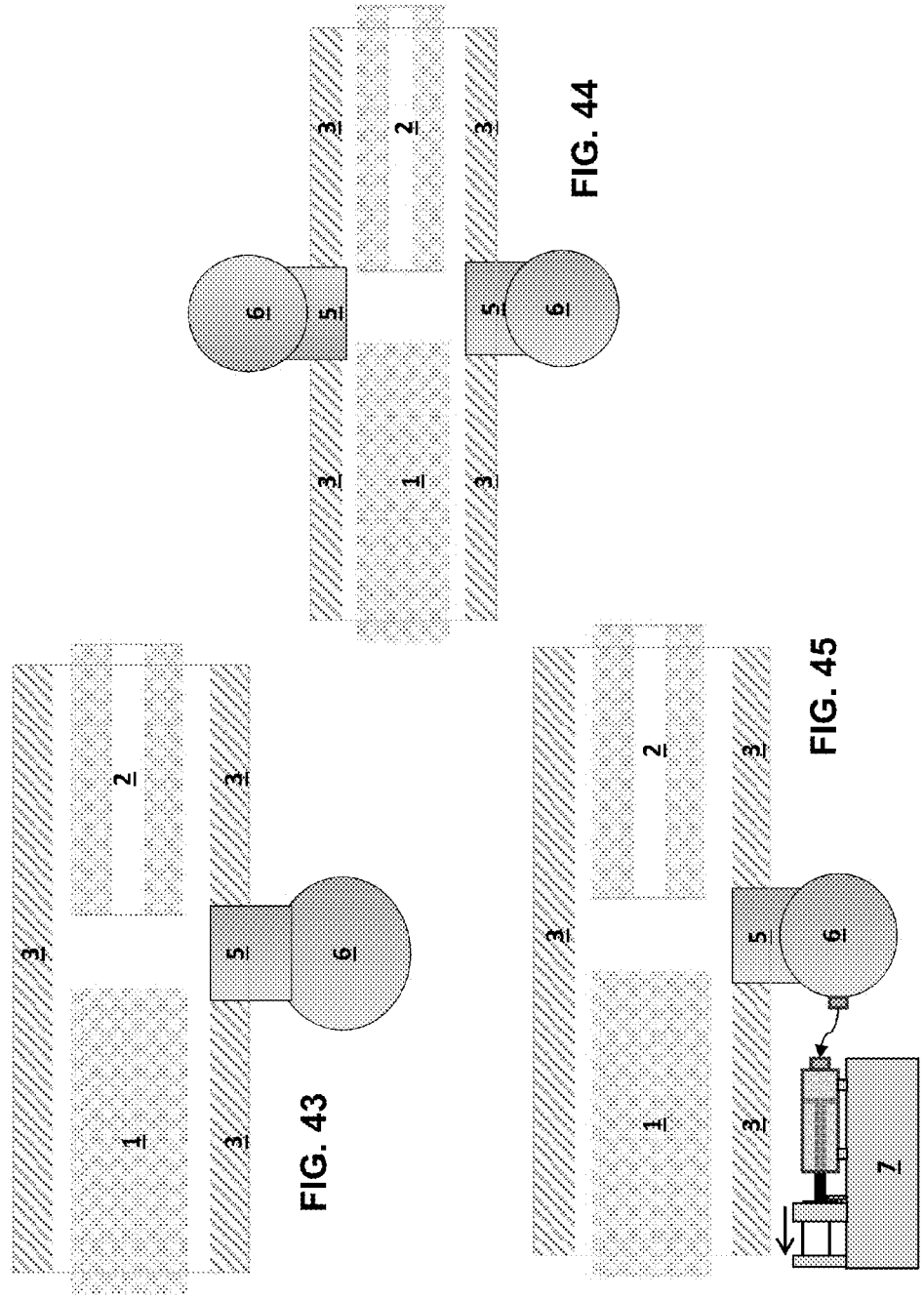

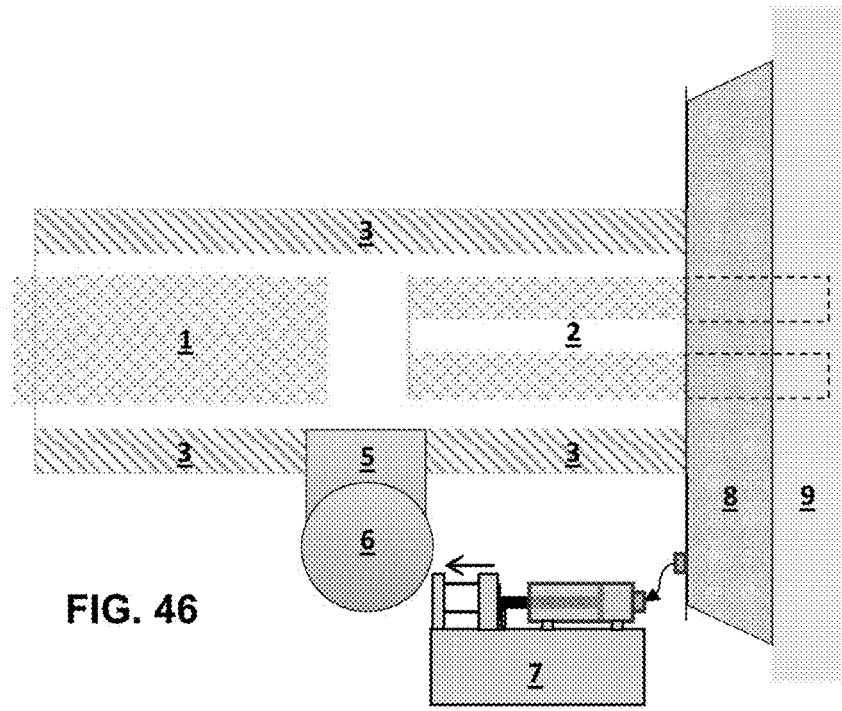
FIG. 46
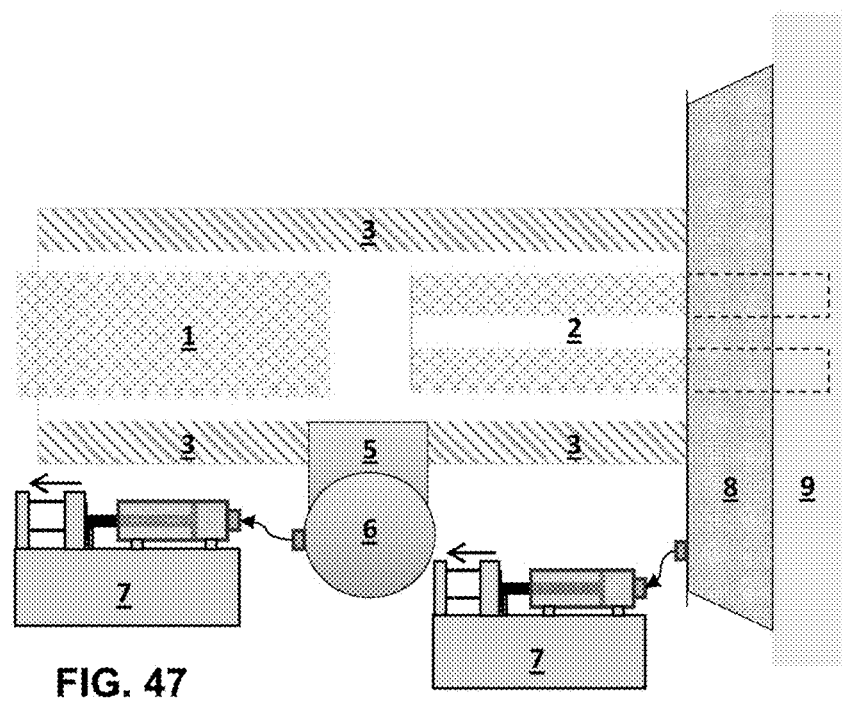
FIG. 47
FIGS. 46-47

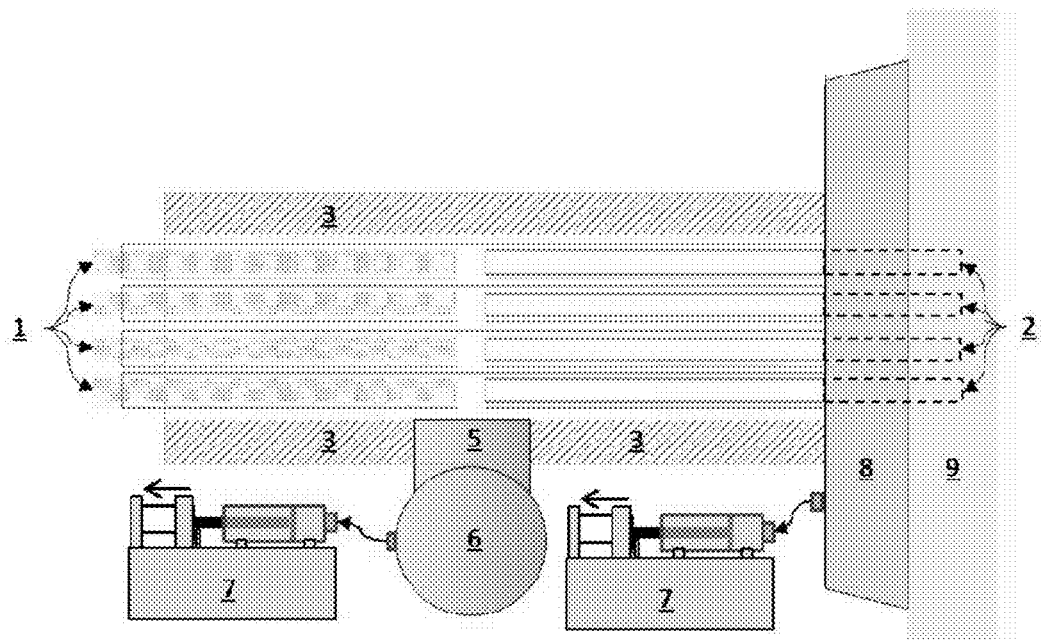
FIG. 48
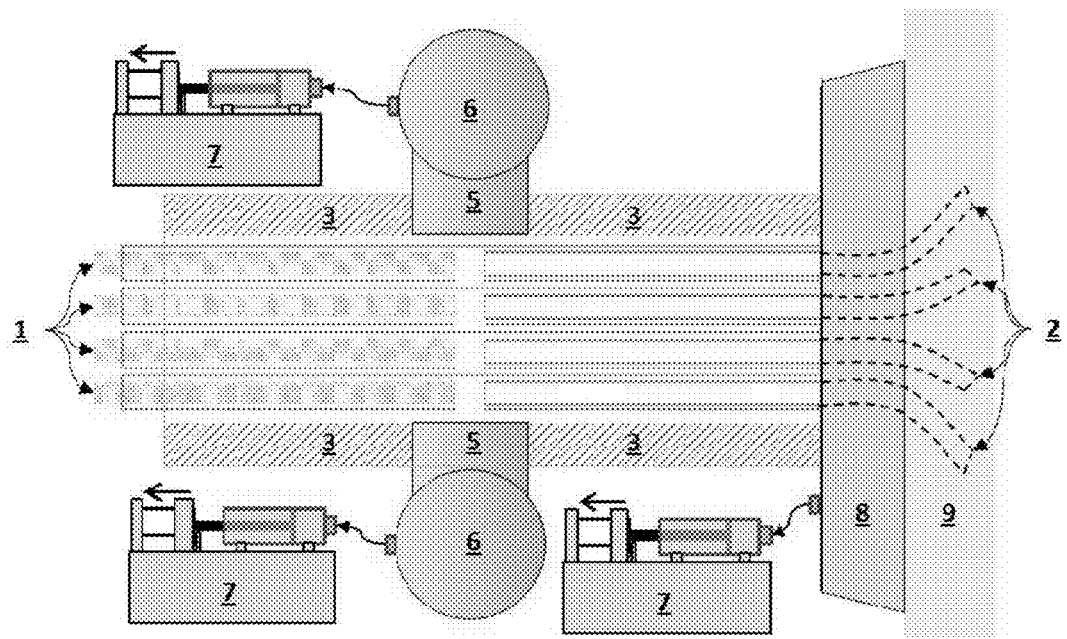
FIG. 49
FIGS. 48-49

Figure 50. Schematic illustration of the fiberoptic microneedle manufacturing process with a representative image from each step (500 mm scale bar).

Figure 51. A schematic representation of microneedle light delivery and specimen interaction experiments. a: Red light delivery/reflectance on white paper; b: 1,064 nm light delivery and photothermal response of white paper; c: 1,064 nm light delivery and structural response of adipose tissue.

FIGS. 51A-C

Figure 52. Diffuse reflectance of red light from white paper during delivery by (a) control, (b) 10-I, (c) 30-I, and (d) 50-III (500-mm scale bar).

FIGS. 52A-D

Figure 53. Temperature distribution after 15 seconds of irradiation (1,064 nm, P ¼ 1 W) for (a) control, (b) 10-I, (c) 30-I, and (d) 50-III.

FIGS. 53A-D

Figure 54. Local temperature along the axes of the microneedles and the control fiber after 15 seconds of irradiation (1,064 nm, P ¼ 1 W).

Figure 55. Images of the adipose tissue before, during, and after 1,064 nm, P ¼ 5 W irradiation for 60 seconds (a) control, (b) 10-I, (c) 30-II, (d) 50-II (500-mm scale bar).

FIBER ARRAY FOR OPTICAL IMAGING AND THERAPEUTICS

CROSS-REFERENCE TO RELATED APPLICATIONS

The present application is a National Stage application under 35 USC § 371 of Application No. PCT/US12/26968, filed Feb. 28, 2012, which application claims priority to and the benefit of the filing date of U.S. Provisional Patent Application Nos. 61/447,380, filed Feb. 28, 2011, and 61/546,090, filed Oct. 12, 2011 and is a Continuation in Part application of U.S. patent application Ser. No. 13/203,800, filed Aug. 29, 2011, which is a national stage application of International Application No. PCT/US10/25809, filed Mar. 1, 2010, which claims priority to and the benefit of the filing date of U.S. Provisional Patent Application No. 61/156,273, filed Feb. 27, 2009, the disclosures of which are hereby incorporated by reference herein in their entireties.

STATEMENT OF GOVERNMENT SUPPORT

This invention was made with government support under contract R21-CA156078 awarded by the National Institutes of Health and contract CBET-0933571 awarded by the National Science Foundation. The government has certain rights in the invention.

BACKGROUND OF THE INVENTION

Field of the Invention

The present invention relates to the field of optical imaging and therapeutics. More particularly, embodiments of the present invention provide minimally-invasive Fiberoptic Microneedle Devices (FMDs) for light-based therapeutics, which physically penetrate tissue and deliver light directly into the target area below the skin surface (FIG. 1). Embodiments of the invention enable depth-selective and deep photothermal therapeutics and include methods of treating cancer, methods of re-shaping or removing adipose tissue, and methods of delivering drugs or co-delivering drugs and energy to selected tissue.

Description of the Related Art

A major limitation for bio-imaging, including optical imaging and therapeutics (such as hair removal or optical tomography techniques, such as OCT imaging), is the shallow penetration depth of light in turbid tissue such as skin. Due to both scattering and absorption of the laser's photons by inhomogeneous tissue structures within the epidermis and dermis such as cells, collagen fibers, and aqueous ground substance, it is difficult if not impossible to maintain a focused or collimated beam past 1 mm depth into tissue. In particular, due to photon scattering around water-encapsulated and water-containing cells, focused light penetration into subcutaneous tissue is prevented, rendering the maximum typical photonic penetration depth of only a few millimeters. Enhancing photonic delivery past this current barrier would enable more selective, deeper, light-based therapeutics and diagnostics.

Currently, light-based therapeutics including oncology treatments, dermatology treatments, cosmetic surgeries, and alternative medicine protocols are limited in the results achieved and/or are not desirable by patients due to the pain typically associated with current procedures for performing these treatments. More specifically, applications that could benefit from improved light-based therapeutics (in particular, increased light penetration in skin) include a broad range of therapeutics ranging from the treatment of deep skin cancers, central nervous system cancers such as malignant gliomas (MGs), bladder cancers such as urothelial cell carcinomas (UCCs) to cosmetic procedures such as laser hair removal, especially for darker-skinned patients and targeted fat removal. By reaching targets beneath the skin surface, such as blood vessels, hair follicles, subdermal fat, and tattoo particles, to name a few, laser-based therapies and cosmetic applications including skin tightening, wrinkle removal, body contouring (fat reshaping or removal), and cellulite reduction could be substantially improved.

For example, minimally invasive laser-based hyperthermia therapy of cancers under the skin, such as melanoma, is currently not feasible due to the shallow penetration of light past the tumor surface. Such therapeutics could be feasible, however, by delivering light several millimeters deep in the tumor. By directly delivering optical radiation in near proximity to target tissue by way of minimally invasive optical fiber needles, the optical dose can be more precise, reducing unwanted collateral tissue damage and associated pain, and faster wound healing (with less scarring and bleeding) can be achieved. Increasing the amount of light penetration could also lead to the detection (and treatment) of tumors located several millimeters beneath the skin's surface through the use of laser-based methods.

Previous research has demonstrated that the light penetration problem can be overcome by using optical fibers to mechanically penetrate skin tissue for the purposes of transmitting light into desired areas. See Prudhomme, M., et al., 1996, "Interstitial Diode Laser Hyperthermia in the Treatment of Subcutaneous Tumor," Lasers in Surgery and Medicine, 19(4), pp. 445-450, the disclosure of which is incorporated by reference herein in its entirety.

Additionally, it has been known to place a silica optical fiber inside a 3.05 mm thick metal cannula with a light diffusing cap made from quartz. Robinson, D. S., et al., 1998, "Interstitial Laser Hyperthermia Model Development for Minimally Invasive Therapy of Breast Carcinoma," Journal of the American College of Surgeons, 186(3), pp. 284-292, the disclosure of which is incorporated by reference herein in its entirety. This design was used to deliver 1064 nm Nd:YAG laser light several centimeters deep into breast tumors.

Vertical cavity surface emitting lasers (VCSELs) are also known. For example, U.S. Pat. No. 7,027,478, entitled "Microneedle Array Systems," the disclosure of which is incorporated by reference herein in its entirety, discloses a device comprising an array of hollow microneedles that are 250 microns in length and have an entrance hole that is 175-200 microns in diameter and an exit hole diameter of 125 microns. Within the hollow portion of the needle (the interior channel) an optical fiber is placed for transmission of light through the needle (which is made of metal and is prepared using photolithography or laser drilling, or is made of high-temperature plastic). Such needles are large and could cause unnecessary damage if inserted into skin. Further, the disclosure does not support extending the technology to smaller needles, and is silent on using additional support means for supporting and guiding the needles during insertion into skin, due to the needles themselves being made of a material (metal or plastic) and having a configuration (large) the combination of which provides sufficient strength to the needles themselves.

Other probe designs were developed for use in diagnostic methods such as optical coherence tomography and optical spectroscopy. See Li, X. D., et al., 2000, "Imaging Needle for Optical Coherence Tomography," Optics Letters, 25(20), pp. 1520-1522; and Utzinger, U., and Richards-Kortum, R. R., 2003, "Fiber Optic Probes for Biomedical Optical Spectroscopy," Journal of Biomedical Optics, 8(1), pp. 121-147, the disclosures of both of which are incorporated by reference herein in their entireties. The fiberoptic probes used in these studies, however, are on the order of 300 μm to several millimeters in diameter. See, e.g., Robinson 1998; Prudhomme 1996; Li 2000; and Mumtaz, H., et al. 1996, "Laser Therapy for Breast Cancer Mr Imaging and Histopathologic Correlation," Radiology, 200(3), pp. 651-658, the disclosure of which is incorporated by reference herein in its entirety.

With respect to physically penetrating skin (e.g., by mechanical means), while reducing or eliminating pain typically encountered by patients undergoing these procedures, it would be desirable to follow a pain-free microneedle model provided in nature—the mosquito fascicle. A mosquito has evolved to penetrate the skin with a flexible biological needle that is extremely small and flexible, inserting it into the skin to draw a meal of blood. The subsequent irritation caused by a mosquito bite is due to the allergic reaction to the saliva that the mosquito secretes during the blood draw to prevent platelet aggregation, not due to the needle insertion itself. See, Ribeiro, J. M. C. and I. M. B. Francischetti, "Role of arthropod saliva in blood feeding: Sialome and post-sialome perspectives," Annual Review of Entomology, 2003, 48: pp. 73-88, the disclosure of which is incorporated by reference herein in its entirety.

Mosquito-performed blood extraction is done through the fascicle which is covered by an outer sheath called the labium. An SEM photograph of a fascicle tip protruding from the end of the partially retracted labium is shown in FIG. 2. See, Ramasubramanian, M. K., et al., "Mechanics of a mosquito bite with applications to microneedle design," Bioinspiration & Biomimetics, 2008, 3(4), the disclosure of which is incorporated by reference herein in its entirety. The dimensions of the mosquito fascicle are typically 1.8 mm long with a 40 μm outer diameter. The tip of the fascicle is very sharp, tapering from about 10 μm to less than 1 μm over the last 50 μm of the fascicle. The fascicle is a polymeric microneedle composed of a ductile material, chitin, with an elastic modulus between 10 and 200 GPa (Ramasubramanian 2008) (similar to the inventive silica microneedles). The critical buckling load for a typical fascicle alone is very low (~3 mN) and not sufficient to penetrate the skin (>10 mN required); however, the lateral support provided by the labium increases the critical buckling load by a factor of 5 and permits successful skin penetration.

Buckling is the most common mode of failure for slender objects forced along their axial direction. This is true for silica-fiber-based fiberoptic microneedles as well. Increasing the buckling force of light guiding needles having a length/diameter ratio of approximately 50 is a challenge. The critical buckling force of a straight cylindrical column with fixed ends can be approximated using Euler's equation. See, Wang, C. M., Wang C. Y., Reddy, J. N., "Exact Solutions for Buckling of Structural Members," CRC Series in Computational Mechanics and Applied Analysis, 2004, the disclosure of which is incorporated by reference herein in its entirety.

A microneedle 2 mm long can safely penetrate skin if its diameter is larger than about 150 μm, which is close to the size of a wood splinter or a standard optical fiber, which are both known to penetrate the skin and inflict some level of pain. As shown in FIG. 3, the critical buckling force of silica microneedles (E=73 GPa for silica) with 2 mm unsupported length is plotted vs. diameter, and, for comparison, the penetration force required for microneedle insertion into skin obtained from results by Davis et al. is also shown. See, Davis, S. P., et al., "Insertion of microneedles into skin: measurement and prediction of insertion force and needle fracture force," Journal of Biomechanics, 2004, 37(8): p. 1155-1163, the disclosure of which is incorporated by reference herein in its entirety.

In order to improve the feasibility of using much smaller, less invasive nano- and micro-needles in clinical applications, the critical buckling force of the needles must be improved. Enhancing photonic transmission depth without absorption and scattering to allow imaging and light-based therapeutics below the epidermis (top 100 μm) and dermis (1-2 mm thick below epidermis) would have important implications in basic research (individual cell imaging), tissue engineering, and tissue therapeutics.

What is needed, and what embodiments of the present invention provide, are thinner fiberoptic microneedles (140 μm or less in diameter) for substantially reducing the morbidity and associated pain caused by insertion of needles into living tissue.

In addition, malignant tumors of the central nervous system are the third leading cause of cancer-related deaths in adolescents and adults and the leading cause of death in children with a mean survival time of 15 months and a mortality rate exceeding 95%. In the past few decades, there has been a steady increase in the incidence of brain cancers and, given the aging population, brain tumors will soon be one of the most commonly encountered human neoplasms. Common approaches to the treatment of aggressive brain tumors such as MGs involve surgery, radiation therapy, and/or various chemotherapeutic regimens and combinations of these three modalities. Previous studies have shown that neither single nor multimodality treatments are curative with the combination of adjunctive therapies using radiation and the chemotherapeutic drug, temozolomide, improving survival by only a few months to a rate of 26%. See, Stupp, R., et al., *"Radiotherapy plus concomitant and adjuvant temozolomide for glioblastoma."* N Engl J Med, 2005. 352(10): p. 987-96, the disclosure of which is incorporated by reference herein in its entirety. These statistics have not changed significantly in 70 years, despite intense medical research focused on improving treatment. At present, treatment of both primary and secondary brain tumors is provided to improve or sustain neurological function of the patient, to diminish the size of the tumor growing intracranially, and to lengthen intervals between treatments. One of the reasons for poor survival is that glioma cells typically infiltrate up to 2 cm beyond the volume of visible tumor, making them difficult to detect and treat. These distant, infiltrating cells may be a key factor in tumor progression and resistance to therapy. Treatment of MGs is also limited by insufficient delivery of chemotherapy drugs due to the blood-brain-barrier.

Current treatments include, but are not limited to, convection-enhanced delivery (CED), which has emerged as a promising method for the delivery of high concentrations of macromolecules to larger regions of brain tissue. The principle of CED involves the stereotactically-guided insertion of a small-caliber catheter into the brain. Through this catheter, infusate is pumped into the brain parenchyma and is pushed primarily through the interstitial space. Infusion is continued for up to several days. In contrast to the millimeter distances obtained with simple diffusion, CED has been shown in laboratory experiments to deliver high-molecular-weight proteins 2 cm into the brain parenchyma after 2 hours of continuous infusion. See Vandergrift, W. A., et al., *"Convection-enhanced delivery of immunotoxins and radioiso-* topes for treatment of malignant gliomas." Neurosurg Focus, 2006. 20(4): p. E13, the disclosure of which is incorporated by reference herein in its entirety. This was accomplished without causing cerebral edema and was unaffected by capillary loss or metabolism of the macromolecule. Compared with other therapies, CED is advantageous by exposing regional brain tissue to high concentrations of chemotherapeutic agents while minimizing systemic and CNS toxicity. However, although CED has achieved greater efficacy than traditional systemic chemotherapy, it has yielded only minor improvements in survival for Phase III clinical trials. This can be attributed to the limited ability of CED to 1) uniformly distribute drug throughout the tumor and 2) broadly disseminate drug to the infiltrative MG cells residing in the primary tumor periphery (not detected by MRI) which correlate with tumor recurrence. The anatomical heterogeneity of the brain is a major limiting factor in perfusion by CED. Portions of the brain are inherently difficult to saturate with drugs due to variations in permeability of white and gray matter, tumor tissue, cerebrospinal fluid tracts, and anatomy of vascular beds. The high lipid content of the brain makes predictable movement of aqueous drug formulations problematic. Also, traditional catheters do not possess the arborizing capability to effectively perfuse drug target to distant infiltrative cells. See Raghavan, R., et al., "*Convection-enhanced delivery of therapeutics for brain disease, and its optimization.*" Neurosurg Focus, 2006. 20(4): p. E12, the disclosure of which is incorporated by reference herein in its entirety. CED efficacy is also limited by the inability to accurately position the catheter and dynamically monitor and control drug distribution.

Clinical and laboratory evidence has shown that hyperthermia (elevated temperature) enhances the cytotoxic effects of several chemotherapeutic drugs (thermochemotherapy) for intraperitoneal tumors. This observed enhancement may be due in part to increased tumor cell membrane permeability and greater drug metabolism by the cells. Hyperthermia may also provide a means to increase regional circulatory dilation and perfusion, which has implications for more effectively perfusing tumor tissue with CED. No studies have investigated the effect of CED perfusion of MGs with laser-induced local hyperthermia.

What is needed, and what embodiments of the present invention provide is a significantly more effective treatment for MGs in which a chemotherapeutic drug is more uniformly and broadly delivered to primary tumor and infiltrative cells (extending >2 cm) thereby diminishing the likelihood of tumor recurrence by allowing simultaneous and co-localized delivery of light and chemotherapy to targeted tissue.

Further, for example, the treatment of urinary bladder cancer is yet another specific type of cancer that may benefit from embodiments of the present invention. Urinary bladder cancer is the fourth most common non-cutaneous malignancy of humans in the United States with approximately 71,000 new cases diagnosed and 15,000 deaths in 2010. UCC, synonymous with transitional cell carcinoma, accounts for approximately 90% of all bladder cancers. Over 30% of UCCs are at an advanced clinical stage when diagnosed, with penetration of tumor cells into the muscularis propia (stages 3 and 4), serosa (stage 4 only), and metastasis to surrounding organs. Radical cystectomy of invasive UCC is the current standard treatment, but its use frequently results in significant post-operative complications. This radical treatment typically requires removal of the bladder, nearby lymph nodes, and part of the urethra in both sexes; the prostate, seminal vesicles, and vas deferens in men; and the ovaries, fallopian tubes, and part of the vagina in women, leading to poor patient quality of life.

Although patient outcomes for advanced stage, invasive bladder cancers are statistically poor, patient outcomes for early stage (stages 0-1) bladder cancers are relatively hopeful. The primary treatment for such early lesions is transurethral resection of the bladder (TURB) followed by chemotherapy. One of the original laser-based alternatives for treatment of superficial bladder tumors was Nd:YAG laser photocoagulation at a 1064 nm wavelength. Unfortunately, laser energy delivered at this wavelength can be damaging to underlying tissues. See Syed, H. A., et al., "*Holmium:YAG laser treatment of recurrent superficial bladder carcinoma: Initial clinical experience.*" Journal of Endourology, 2001. 15(6): p. 625-627, the disclosure of which is incorporated by reference herein in its entirety. Nd:YAG-based treatments were succeeded by the Ho:YAG laser (2.1 μm wavelength) for photothermal treatment of superficial bladder cancers, which has become widely utilized. Several studies have shown that treatment with the Ho:YAG laser is safe, effective, and associated with rapid patient recovery, indicating it is a viable alternative to standard TURB or electrocautery for treating early stage bladder cancer. While effective for superficial tumors, Ho:YAG laser treatment has proven ineffective for invasive, late stage bladder tumors due to insufficient light penetration into the tumor mass. See Johnson, D. E., "*Use of the Holmium-Yag (Ho Yag) Laser for Treatment of Superficial Bladder-Carcinoma.*" Lasers in Surgery and Medicine, 1994, 14(3): p. 213-218, the disclosure of which is incorporated by reference herein in its entirety. Light at a wavelength of 2.1 μm penetrates bladder tissue approximately 0.5 mm, which is insufficient to treat late-stage tumors that invade the muscular and serosal layers 2-4 mm into the bladder wall. See Hruby, G. W., et al., "*Transurethral bladder cryoablation in the porcine model.*" Journal of Urology, 2008. 179(4), the disclosure of which is incorporated by reference herein in its entirety. Inadequate delivery and heating of deep tumor volumes result in generation of poorly defined lesion boundaries and a high likelihood of tumor re-growth, recurrence, necrosis, and possible perforation of the bladder wall.

What is needed, and what embodiments of the present invention provide methods using FMD devices that are capable of penetrating the bladder mucosa and muscularis to co-deliver exogenous photoabsorbers and light interstitially, thereby increasing the spatial control of treatment.

Even further, on the cosmetic surgery front, improvements in treatment protocols especially for fat re-shaping procedures and the like are also needed. More particularly, in such treatment protocols, focused or near-collimated light only travels a few millimeters into turbid tissues, due to the combined effects of photon scattering and absorption. Many laser cosmetic procedures, such as laser lipolysis and hair removal, have limited efficacy and restricted uses, due to the short penetration depth of ht into skin and underlying tissue. Other potential applications, such as treatment/ablation of skin tumors, are similarly limited by this obstacle. Therefore, light-guiding optical fibers with flat end faces are commonly used to deliver visible and near-infrared light interstitially to deeper tissue regions, However, an optical fiber with a flat end face limits the laser power that can be delivered safely because high irradiance at the tip leads to excessive temperature elevation, causing both carbonization of the tissue and thermal damage to the fiber itself.

To deliver increased amounts of therapeutically useful energy to large tissue regions, several types of optical diffusers have been developed. Such optical diffusers provided uniform delivery of light from their surfaces for photothermal and photochemical laser therapy procedures. Even though the radiant emittance profile can be well-controlled at the surface of the diffuser, the fluence distribution inside the tissue is determined by inherent tissue optical properties, limiting the volume of tissue that can be treated with a single diffuser. Multiple diffusers have been shown to deliver effective levels of laser energy to larger tissue volumes.

Thus, what is needed and what the inventors provide, is a new microneedle design that delivers light circumferentially along a length of 3 mm, functioning as a microscale optical diffuser for laser therapy procedures.

SUMMARY OF THE INVENTION

To address some of the issues relating to light-based therapeutic and diagnostic procedures, embodiments of the present invention provide minimally invasive fiberoptic microneedles capable of physically penetrating tissue to deliver light directly to target areas below the skin surface to allow for increased spatial control of treatment.

Objects of embodiments of the present invention provide: 1) novel microneedle structures including but not limited to silica solid, hollow-core, and photonic crystal fibers; 2) methods and devices for mechanically (e.g., physically) inserting these microneedle fiber arrays into human tissue; and 3) novel biomedical applications involving light/fluid transport through these fibers and tissue for applications including: i) photo-therapy, ii) optical sensing or imaging for diagnostics, iii) fluid/drug delivery, iv) biochemical sensing/diagnostics; and v) multi-modal combinations of the aforementioned applications.

In embodiments of the invention, the fiberoptic microneedle device (FMD) bypasses the turbid skin barrier by insertion of extremely small light-delivering microneedles in proximity to the target tissue. The microneedles are mechanically stabilized to prevent buckling and are painlessly guided into a patient's skin using a novel guidance ferrule template and an elastomeric material. The FMD allows increased light penetration in skin and can substantially improve a variety of light-based therapeutic and diagnostic procedures.

Embodiments of the invention comprise a fiberoptic microneedle or an array of fiberoptic microneedles for light delivery using brightfield imaging in tissue representative phantoms. Embodiments also include a fiberoptic microneedle device (FMD) capable of penetrating skin using white light photographic imaging and thermal imaging during laser irradiation. Methods for using such fiberoptic needles and FMDs to treat a variety of conditions or diseases are also within the scope of the invention.

Fiberoptic microneedles and microneedle devices according to the present invention can comprise a support member for increasing the critical buckling force of the needle(s) to fortify the needles for insertion into skin. It has been found that if a microneedle is embedded inside an elastic medium such as a polymer, the medium will act like a series of springs that limit the lateral movement of the microneedle, increasing its critical buckling force, and enabling skin penetration similar to the mechanism used in mosquito bites.

Further, embodiments of the invention include light guiding microneedles manufactured from standard multimode silica fibers. An exemplary method for manufacturing such fiberoptic needles is by drawing silica fibers into a tapered (needle-like) shape by heating the fibers to their melting temperature and stretching them with a mechanical stage. Such a manufacturing process allows for needles with different geometries to be made, including needles having centimeter lengths and/or sub-micron tip diameters.

A range of various needle geometries have shown potential. For example, using white-light photographic imaging with a stereo microscope, FIG. 3 provides a sequence of photographic images demonstrating the feasibility of 1 mm needle penetration into ex vivo porcine skin. The needle in this example remained intact (buckling not observed) even after removal from the skin, in part due to the high taper angle of the needle. A penetration depth of up to 1 mm is sufficient to bypass the epidermal layer of the skin, which contains melanin, the matter responsible for much of the light absorption in light-based therapeutics.

Embodiments of the invention can also comprise additional mechanical support or strengthening of the needle, for providing a range of feasible microneedle variations for numerous applications. Toward this end, embodiments of devices of the invention can comprise an array of optically transparent fibers (either nano- or microscale in diameter), which are capable of being guided into a patient's skin using a guidance ferrule template and an elastomeric support material for increasing the buckling force of the needle(s).

Specific aspects of the present invention include aspect 1, a method of treating fat tissue comprising: inserting one or more fiber optic microneedles into fat tissue, which microneedle has a minimum outside diameter of about 25-150 µm, such as 30-70 µm, or 35-50 µm; and delivering light, at a wavelength in the range of 630-2100 nm, into the tissue for a time and under sufficient conditions to liquefy at least a portion of the fat tissue by delivery of the light at least in part circumferentially along a lateral aspect of the needle.

Aspect 2 includes the method of aspect 1 in which light is delivered over a surface area in the range of 0.10-0.50 $mm^2$ or over a surface area of more than 035 $mm^2$.

Aspect 3 is the method of aspect 1 or 2 comprising aspirating the liquefied fat by suction. Even further, aspect 4 includes the method of aspect 3, wherein one or more of the microneedles is hollow and fat is aspirated through one or more hollow microneedle. Aspect 5 is the method of any of aspects 1-4 comprising heating the fat during aspiration.

Aspect 6 can include the method of any of aspects 1-5, wherein the light has a wavelength of 630-650 nm, such as 640 nm; or wherein the light is near infrared and has a wavelength of 750-1400 nm, such as 915-980 nm, such as 915 nm, 920 nm, 924 nm, 924-970 nm, or 980 nm; or wherein the light has a wavelength of 1064 nm; or wherein the light has a wavelength of 1210 nm; or wherein the light has a wavelength of 1308 nm, 1320 nm, or 1440 nm or a combination thereof, or a wavelength alternating between 1308 nm, 1320 nm, or 1440 nm; or wherein 1064 nm and 1440 nm light is delivered for fat liquefaction and 1064 nm and 1320 nm light is delivered for collagen stimulation and blood vessel coagulation; or wherein 1440 nm, 1064 nm, and 1320 nm of light is delivered.

Aspect 7 is a method of any of aspects 1-6 comprising an array of microneedles.

Aspect 8 is a method of any of aspects 1-7, wherein one or more of the microneedles has a length from base to tip of about 3 mm.

Aspect 9 includes a method of any of aspects: 1-8 comprising a microneedle support ferrule.

Aspect 10 is a method of any of aspects 1-9 comprising no carbonization of tissue and the local temperature of the needle and tissue is below about 100° C.

Aspect 11 includes a method of any of aspects 1-10, wherein the optical fiber is multi-modal.

Further, aspect 12 can comprise a method of any of aspects 1-11 comprising temperature monitoring.

In embodiments, aspect 13 includes a method of any of aspects 1-12 comprising irradiating the fat tissue by delivering 1064 nm of light for at least 60 seconds. Any length of time can be used in any of the methods according to the invention. Preferred protocols include delivering light for up to 5 minutes, for example, for up to 1, 2, 3, 4, or 5 minutes. The light need not be delivered at a constant wavelength and multiple wavelengths can be administered. Pulsing protocols are also within the scope of the invention where pulses of a specified wavelength are administered for up to 5 minutes, or pulses of one wavelength are administered/delivered for 1 minute, then pulses or a constant intensity of a different wavelength of light can be administered for up to 1 minute, and the sequence repeated until a desired total amount of exposure of tissue to light has been achieved.

Aspect 14 is a method of any of aspects 1-13, wherein the optical fiber is a hollow cylindrical optical fiber having: (i) a base with a maximum outer diameter of about 50 μm to several millimeters; and (ii) a hypodermic tip extending from the base into a tip end.

Aspect 15 is a microneedle device or system for implementing any one of the methods described in aspects 1-14.

Aspect 16 is a method of treating a tumor comprising: inserting a hollow core fiber optic microneedle into tissue; delivering photoabsorbers into the tissue through the hollow core fiber; and delivering a selected amount of light energy into the photoabsorbers for a time and under sufficient conditions to induce a desired amount of selective photothermal or photochemical damage in the tissue.

Aspect 17 is a method of aspect 16, wherein the tissue is a bladder tumor.

Aspect 18 is a method of aspect 16, wherein the photoabsorbers are chromophores such as nanomaterials or porphyrins. Further, aspect 19 is a method of aspect 16, wherein the photoabsorbers are light absorbing dyes. Likewise, in aspect 20, a method of any one of aspects 16-19 can comprise photoabsorbers which are nanomaterials, such as single walled carbon nanohorns (SWNH).

Aspect 21 includes a method of any of aspects 16-20, wherein the photoabsorbers are SWNH nanoparticles encapsulated with imaging or treatment agents, such as gadolinium or quantum dots on the surface and/or interior pores of the SWNHs, for diagnostic imaging.

Aspect 22 is a method of any of aspects 16-21, wherein light is delivered at a wavelength of 630-2100 nm, such as 1064 nm.

Aspect 23 includes a method of any of aspects 16-22, wherein the hollow core fiber optic microneedle comprises an outer diameter of 200-500 μm, an inner diameter of 50-450 μm, and a sharp beveled tip, such as having a 365 μm or 250 μm outer diameter and a 150 μm inner diameter.

Aspect 24 is a method of any of aspects 16-23, wherein the light is delivered using one or more hollow core fiber optic microneedle. Aspect 25 is method of any of aspects 16-23 comprising one or more solid fiber optic microneedle coupled with a light source for delivering the light. In all embodiments of the methods, devices, and systems according to the invention, to deliver light through the microneedle, a light source such as a laser can be coupled with the optical fiber(s). In preferred embodiments, the light source is in operable communication with an end of the fiber(s) and if more than one fiber is used the fibers are disposed end to end. There is no requirement that the fibers be touching one another in order to transmit light from one to another and indeed in some embodiments it may be preferred to have some spacing between fibers to allow for the passage of materials such as liquids between the fibers.

Aspect 26 can include a method of aspect 25, wherein the solid fiber optic microneedle has an outer diameter of from 25-150 μm and an inner core diameter of from 5-125 μm, such as an outer diameter of 80 μm and an inner core diameter of 50 μm.

Aspect 27 includes a fiber optic microneedle device or system comprising such a microneedle or an array of microneedles for performing any method of aspects 1-24.

Aspect 28 is a fiber optic microneedle system for performing a method according to aspect 25 or 26.

Aspect 29 is a light arborizing catheter comprising: a guide tube for supporting a bundle of fiber optic microneedles; a bundle of fiber optic microneedles arranged lengthwise within the guide tube; and one or more deflectors for guiding the light from each microneedle at a desired angle.

Aspect 30 is the catheter of aspect 29 comprising seven fiber optic microneedles, wherein six microneedles are disposed circumferentially around one microneedle. Any number of microneedles can be used in the bundle and the microneedles can be arranged in any relationship to one another. In preferred embodiments, the microneedles are disposed lengthwise within the guide tube and in a manner (e.g., cladding or a separate channel within the guide tube) that prevents light from one of the fibers from passing into the other fibers.

Aspect 31 is a catheter of aspect 29 or 30 comprising a separate channel along the length of the guide tube for each microneedle in the bundle of microneedles.

Aspect 32 is a catheter of any of aspects 29-31, wherein one or more of the microneedles is a solid fiber optic microneedle. Similarly, aspect 33 is a catheter of any of aspects 29-32, wherein one or more of the microneedles is a hollow fiber optic microneedle.

Aspect 34 can comprise a catheter of any of aspects 29-33, wherein one or more of the microneedles has an outer diameter ranging from about 100-500 μm and an inner diameter ranging from about 50-365 μm, such as a 365 μm or 250 μm O.D. and a 150 μm I.D.

Aspect 35 includes a catheter of any of aspects 29-34 comprising means for inserting the microneedles into tissue up to about 10 cm, such as up to about 5 cm.

Aspect 36 is a catheter of any of aspects 29-35 for treating brain tissue.

Aspect 37 is a catheter of any of aspects 29-36, wherein one or more of the microneedles is configured to deliver chemotherapeutic agents, such as carboplatin.

Aspect 38 is a method of treating brain cancer comprising inserting one or more microneedles into a brain tumor using a catheter of any of aspects 29-37 and delivering a selected amount of light energy into the tumor for a time and under sufficient conditions to damage the tumor.

Aspect 39 is a light guiding microneedle device comprising: an elongated outer sheath defining a passageway therethrough; one or more light guiding microneedle disposed lengthwise within the sheath; and a channel for the transport of liquid through the sheath.

Aspect 40 can comprise a microneedle device of aspect 39 comprising at least one hollow microneedle and at least one solid core microneedle disposed to allow light to pass from one to the other.

Aspect 41 is a microneedle device of aspect 39 or 40 comprising an outlet in the sheath for removing liquid from the sheath.

Aspect 42 is a microneedle device of any of aspects 39-41 comprising multiple hollow and solid core microneedles. More particularly, in aspect 43, the microneedle device of any of aspects 39-42 can comprise one or more microneedle(s) having a minimum outside diameter of about 25-150 µm, such as 30-70 µm, or 35-50 µm.

Aspect 44 includes a system for removing liquefied fat from a body comprising a microneedle device of any of aspects 39-43 with means for suctioning liquefied fat from a body and means for imposing positive or negative pressure on the body to facilitate fat removal.

Aspect 45 is a fiber optic needle, or an array of fiber optic needles, wherein one or more comprises a hollow cylindrical optical fiber having: (i) a minimum outside diameter of about 25-150 µm, such as 30-70 µm, or 35-50 µm; (ii) a length of 3 mm or more; and (iii) embedded in PDMS.

Aspect 46 includes the fiber optic needle of aspect 45, which is hollow.

These aspects of embodiments of the invention have been provided to give general guidance about specific features of the invention. Other features and advantages of the present invention will be apparent to those skilled in the art. While numerous changes may be made by those skilled in the art, such changes are within the spirit of the invention. For example, any one or more of the elements described for methods, devices, and systems in this specification can be combined with other embodiments described herein. Similarly, one or more elements of these methods, systems, and devices can be optional. One of skill in the art will know when it is appropriate to add to, subtract from, or combine in different orders one or more of these elements. More detail is provided below regarding the functional features of the methods, systems, and devices disclosed herein.

BRIEF DESCRIPTION OF THE DRAWINGS

These drawings illustrate certain aspects of some of the embodiments of the present invention, and should not be used to limit or define the invention.

FIGS. 29A-C are schematics of FMD co-delivery couple design showing in FIG. 29A a cut-away of the co-delivery couple showing the alignment of the light conducting fibers and position of the fluid input; in FIG. 29B a cross-section of the input of the couple, exhibiting the position of the light and fluid inputs; and in FIG. 29C a cross-section of the output of the couple, exhibiting the position of the co-delivery HCF.

FIGS. 30A-D are images depicting SWNH infusion through HCF into an ex vivo porcine bladder wall, where FIG. 30A is at t=0, area=0; FIG. 30B is at t=4 min, area=1.5 cm$^2$; FIG. 30C is at t=8 min, area=2.6 cm$^2$; and FIG. 30D is at t=12 min, 3.2 cm$^2$.

FIG. 33A is an image of a gross section fixed bladder wall following 5 minute infusion into thicker region of uninflated bladder.

FIG. 33B is an image of a histological section cut directly from the gross section from FIG. 33A.

FIG. 33C is an image of a gross section of fixed bladder wall following 10 minute infusion into inflated bladder.

FIG. 33D is an image showing a close view of the stained section (location denoted by black boxes in FIGS. 33A and 33B showing expansion of the loose connective tissue in the mucosal layer from fluid expansion caused by SWNH infusion.

FIGS. 34A and 34B depict thermographs of laser heating perfused bladder tissue in regions FIG. 34A without SWNHs and FIG. 34B with SWNHs, with the color scale showing temperature in degrees Celsius.

FIGS. 36A, B and C shows irradiation from light-guiding, hollow-core microneedle after delivering SWNHs into the inflated bladder wall, wherein FIG. 36A is a photograph showing microneedle position (Note: the red guide laser is visible), FIG. 36B is a thermograph of non-infused control, and FIG. 36C is a thermograph of SWNH perfused tissue. Color scale is in Celsius, white lines denote fiber path.

FIG. 37 is a schematic diagram showing a side cross-sectional view of the device illustrating one embodiment of the invention, where laser light can be conducted from left to right from the (1) solid core fiber to the (2) hollow core fiber, and liquefied fat can be conducted from the right through the HCF and out the (4) side port in the (3) sheath.

FIG. 38 is a schematic diagram showing a side cross-sectional view of a device illustrating one embodiment of the invention, where laser light can be conducted from left to right from the (2) HCF to a second (2) HCF, and liquefied fat be can be conducted from the right through the hollow core fiber and out the (4) side port through the (3) sheath.

FIG. 39 is a schematic diagram showing a side cross-sectional view of the device illustrating one embodiment of the invention, where laser light can be conducted from left to right from the (1) solid core fiber to the (1) solid core fiber, and liquefied fat can be conducted from the right around the solid core fiber and out the (4) side port through the (3) sheath.

FIG. 40 is a schematic diagram showing a side cross-sectional view of the device illustrating one embodiment of the invention, where laser light can be conducted from left to right through the (2) hollow core fiber, and liquefied fat can be conducted from the right through the hollow core fiber (HCF) and out the left side of the (3) sheath.

FIG. 41 is a schematic diagram showing a side cross-sectional view of the device illustrating one embodiment of the invention, where laser light can be conducted from left to right through the (1) solid core fiber, and liquefied fat can be conducted from the right around the solid core fiber and out the left side of the (3) sheath.

FIG. 42 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out the one of the two (4) side ports through the (3) sheath.

FIG. 43 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out the (5) modified side port through the (3) sheath which guides the fat into a (6) reservoir/bladder.

FIG. 44 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out one of the (5) modified side ports through the (3) sheath which guides the fat into (6) reservoirs/bladders.

FIG. 45 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out the (5) modified side port through the (3) sheath which guides the fat into a (6) reservoir/bladder. In this embodiment, it is demonstrated that movement of the liquefied fat can be aided by negative pressure provided by the (7) syringe pump to the reservoir space.

FIG. 46 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out the (5) modified side port through the (3) sheath which guides the fat into a (6) reservoir/bladder. Movement of the liquefied fat can be aided by a (8) suction cup and (7) syringe pump providing positive pressure to the (9) local tissue.

FIG. 47 is a schematic diagram showing a side cross-sectional view of the device illustrating one embodiment of the invention, where laser light can be conducted from left to right through the (1) solid core fiber to the (2) hollow core fiber, and liquefied fat can be conducted from the right through the hollow core fiber and out the (5) modified side port through the (3) sheath which guides the fat into a (6) reservoir/bladder. Movement of the liquefied fat can be aided by a (8) suction cup and (7) syringe pump providing positive pressure to the (9) local tissue and negative pressure provided by a (7) syringe pump to the reservoir space (6).

FIG. 48 is a schematic diagram showing a side cross-sectional view of the device illustrating one embodiment of the invention, where laser light can be conducted from left to right through an array of (1) solid core fiber(s) to the (2) hollow core fiber(s), and liquefied fat can be conducted from the right through the hollow core fiber(s) and out the (5) modified side ports through the (3) sheath which guides the fat into a (6) reservoir(s)/bladder(s). Movement of the liquefied fat can be aided by a (8) suction cup and (7) syringe pump providing positive pressure to (9) local tissue and negative pressure provided by one or more (7) syringe pump(s) to the reservoir space(s).

FIG. 49 is a schematic diagram showing a side cross-sectional view of the device illustrating one embodiment of the invention, where laser light can be conducted from left to right through an array of (1) solid core fiber(s) to the (2) hollow core fiber(s), and liquefied fat can be conducted from the right through the arborizing hollow core fiber(s) and out the (5) modified side ports through the (3) sheath which guides the fat into a (6) reservoir(s)/bladder(s). Movement of the liquefied fat can be aided by a (8) suction cup and (7) syringe pump providing positive pressure to the (9) local tissue and negative pressure provided by one or more (7) syringe pump(s) to the reservoir space(s).

FIG. 55A is the control; FIG. 55B is 10-I; FIG. 55C is 30-II; and FIG. 55D is 50-II (500-μm scale bar).

DETAILED DESCRIPTION OF VARIOUS EMBODIMENTS OF THE INVENTION

Figure 1:
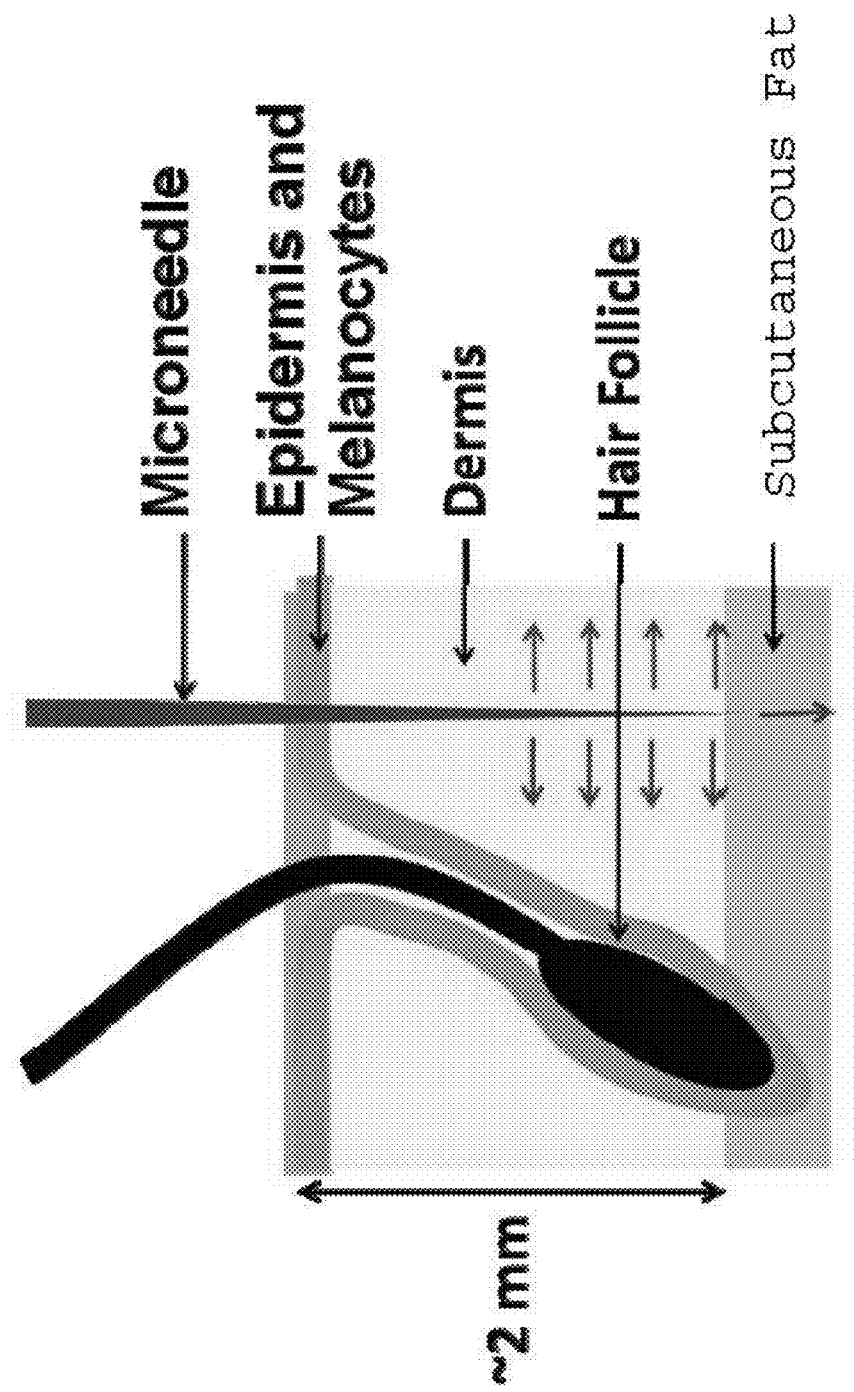
FIG. 1 is a schematic diagram showing a fiberoptic microneedle according to the invention inserted to a depth (approx. 2 mm) below the surface of the skin, to place the needle in a position for delivering light to a target (e.g., hair follicle) of a light-based therapy.

Reference will now be made in detail to various exemplary embodiments of the invention. The following detailed description is presented for the purpose of describing certain embodiments in detail and is, thus, not to be considered as limiting the invention to the embodiments described. Rather, the true scope of the invention is defined by the claims.

Embodiments of the invention provide a non-metal needle comprising structure for transmitting light, which is capable of piercing human tissue, and has a maximum diameter in the range of about 100-300 micron. Also included are needles comprising a base having an outer diameter in the range of about 100-300 micron and a tip having an outer diameter in the range of about 5-50 micron. Further provided are needles comprising a base having an outer diameter in the range of about 100-200 micron and a tip having an outer diameter in the range of about 5-40 micron. Other embodiments provide needles comprising a base having an outer diameter in the range of about 100-150 micron and a tip having an outer diameter in the range of about 5-20 micron. Certain embodiments provide needles comprising a base having an outer diameter in the range of about 100-125 micron and a tip having an outer diameter in the range of about 5-10 micron.

A non-metal material or "non-metal" as used in this disclosure refers to any material that is a poor conductor of heat and electricity. Non-metals in accordance with the present invention can also include materials having a thermal conductivity (at about 25° C.) of about 5 k (W/mK) or less, such as about 2-4 k, or such as about 1 k or less. Silica or silica-based materials or fibers, even though they may contain metals in their compositions are non-metals according to the invention. Ceramics, quartz, plastics, and polymers are also non-metals according to the invention, including many other materials having similar properties. In contrast, aluminum, copper, iron, alloys, brass, nickel, silver, gold, lead, molybdenum, zinc, magnesium, stainless steel, etc. for example are exemplary metals.

Certain embodiments provide needles of comprising a hollow core having an inner diameter in the range of about 1-8 micron. Other embodiments provide a needle having a length of about 0.5-6 mm. Embodiments of the present invention provide the needle having a length of about 1-3 mm. Some embodiments provide a needle comprising a hollow core having an inner diameter in the range of about 1-5 micron.

Certain embodiments provide a needle wherein the light-transmitting material is silica. Other embodiments provide a needle comprising multi-mode silica fiber or single-mode silica fiber, and any combination thereof. Embodiments of the present invention provide a needle comprising a flat or non-tapered tip, a tapered tip end, wherein the needle has a first taper defined by an outer diameter that becomes increasingly smaller along a length of the needle toward the tip end and a second taper defined by an outer diameter that becomes increasingly smaller within 10-20% of the tip end based on overall needle length, and any combination thereof.

Certain embodiments of the present invention provide a needle comprising a light-blocking coating. In some embodiments the needle structure is formed from heating and stretching a silica-based fiber cylinder or rod, having a first average outer diameter along the length of the fiber, until a second outer diameter smaller than the first is obtained in a region of the fiber and breaking the fiber at a point in the second smaller diameter region. In embodiments, due to variations in diameter along the length of the fiber, it may be appropriate to refer to the needles as having a minimum outer diameter of a selected dimension. In some embodiments, the breaking of the fiber involves stopping the heating and stretching of the fiber, cooling the fiber, and mechanically breaking the fiber in the needle. Other embodiments provide a needle, wherein breaking of the fiber involves direct laser heating at a point in the second smaller diameter region combined with stretching of the fiber at a rate sufficient to obtain a third outer diameter smaller than the second and sufficient to break the fiber at a point in the third smaller diameter region to form a tapered tip.

Also included in embodiments of the invention is a fiberoptic microneedle device comprising: (a) one or more needles of any of claims 1-18; (b) a support member to which the needles are secured; and (c) a ferrule comprising one or more holes for each of the needles, wherein the ferrule is operably configured to provide mechanical support to each needle at all or some portion of the length of the needle. Further included in some embodiments is a fiberoptic microneedle device comprising: (a) one or more silica-based needles capable of guiding light and comprising a length of about 0.5-6 mm, a base having an outer diameter in the range of about 100-150 micron, and a tip having an outer diameter in the range of about 5-20 micron; (b) a support member to which the needles are secured; and (c) a ferrule comprising one or more holes for each of the needles, wherein the ferrule is operably configured to provide mechanical support to each needle at all or some portion of the length of the needle.

Certain embodiments provide a device comprising an array of needles.

In such embodiments the device comprises a ferrule wherein the ferrule is made of flexible materials or rigid materials, or any combination thereof.

Embodiments of the invention include a device comprising an electrical, mechanical, pneumatic, or hydraulic actuation source for inserting the needles into the ferrule, moving the needles within the ferrule, or causing protrusion of a portion of the needles from the ferrule. Further, certain embodiments include a device comprising means for compressing the flexible ferrule or flexible portion of the ferrule against a surface to cause the needles to protrude from the ferrule into the surface. In embodiments, there is the device which can be used with human skin.

Certain embodiments provide a needle or a device comprising a light source operably connected with the needles to transmit light through the needles. Embodiments provide a needle or device, wherein the light source is a laser. Embodiments further provide a device comprising a control system with feedback capabilities to monitor and control power and duration of light delivery from the needles; or monitor and control pressure, volume, and rate of flow of fluids or particles through the needles; or monitor and control depth of protrusion of the needles from the ferrule.

Certain embodiments comprise a device comprising means for applying positive or negative vacuum pressure for temporarily securing the ferrule to a surface and stabilizing the device for insertion of the needles into the surface from and through the ferrule.

Also included in embodiments of the invention are methods of performing photothermal, photochemical, or photomechanical therapy in tissue comprising delivering light on a tissue surface, in a tissue surface, or below a tissue surface using any needle or microneedle device disclosed herein. Embodiments provide a method of detecting disease in tissue comprising delivering light on a tissue surface, in a tissue surface, or below a tissue surface using any needle disclosed herein to collect data about the tissue. Other embodiments provide a method comprising delivering light below a surface. The surface in such embodiments may be human skin surface.

Embodiments of the invention provide methods of performing photothermal, photochemical, or photomechanical therapy in tissue or of detecting disease in tissue comprising delivering light on, in, or below a tissue surface using one or more needles or needle devices disclosed in this specification and targeting one or more of cancer, blood vessels, hair follicles, subdermal fat, tattoo particles, or skin.

Devices and methods according to embodiments of the invention can include a non-metal needle comprising: a hollow cylindrical optical fiber with: (i) a base with a maximum outer diameter of about 50 μm to several millimeters; (ii) a hypodermic tip extending from the base into a tip end; wherein the needle has a lower force of insertion than a needle having the same base but no hypodermic tip.

Further included in methods and devices of the present invention is a fiberoptic microneedle device comprising: one or more non-metal needle formed from a hollow cylindrical optical fiber and comprising (i) a base with an outer diameter of about 50 μm to several millimeters; (ii) a hypodermic tip extending from the base into a tip end, wherein the needle has a lower force of insertion than a needle having the same base but no hypodermic tip; a support member to which the needles are secured; and a ferrule comprising one or more holes for each of the needles, wherein the ferrule is operably configured to provide mechanical support to each needle at all or some portion of the length of the needle.

Representative embodiments of the present invention are described in greater detail below. For convenience, Table 1 below provides a list of terms used in this disclosure and their corresponding definitions.

TABLE 1

| | List of Terms |
|---|---|
| $\alpha_T$: | Taper angle of flat microneedles |
| $\alpha_{T1}$: | First taper angle of sharp microneedles |
| $\alpha_{T2}$: | Second taper angle of sharp microneedles |
| $\lambda$: | Wavelength of light |
| $CO_2$: | Carbon dioxide |
| CCD: | Charge-coupled device |
| $d_{AVG}$: | Average diameter of a microneedle |
| $d_{AVG,FLAT}$: | Average diameter of a flat microneedle |
| $d_{AVG,SHARP}$: | Average diameter of a sharp microneedle |
| $d_{BASE}$: | Base diameter of a microneedle |
| $d_{INF}$: | Diameter at inflection point for sharp microneedles |
| $d_{TIP}$: | Tip diameter of a microneedle |
| E: | Elastic modulus of silica |
| F1-8: | Flat microneedles |
| L: | Unsupported length |

TABLE 1-continued

List of Terms

| | |
|---|---|
| $L_{TIP}$: | Tip length, length of the second taper |
| $F_{CR}$: | Critical buckling force of a microneedle |
| $F_{INS}$: | Skin insertion force |
| Nd:YAG: | Neodymium-doped Yttrium Aluminium Garnet |
| S1-12: | Sharp microneedles |

Needles according to embodiments of the invention, or used with device embodiments of the invention, can comprise any length, diameter, tapering characteristics, material, wall thickness, etc. desirable or needed for a particular application. For example, the microneedles of the invention can range from 1 mm to 5 mm in length. Due to the nature of the technology, the length of the needle can also include any length of fiber leading from the light source to the tip of the needle. In such cases, the length of the needle or fiber, which may be used interchangeably, can be 100 cm long, for example. A preferred length of microneedle (selected to satisfy the light penetration depth needed for skin carcinoma applications) is at least a 3 mm long microneedle. Such microneedles can be used to physically penetrate skin and deliver light into subdermal locations.

Any length needle can be used in accordance with the present invention, including needles that are at least 0.5 mm, 1 mm, 1.5 mm, 2 mm, 2.5 mm, 3.5 mm, 4 mm, 4.5 mm, 5 mm, 5.5 mm, 6 mm, and so on in overall length. As used in this specification, the length of the needle or fiber can refer to a measurement from the base of the needle to the tip of the needle, or can refer to the length of the portion of the needle intended to be inserted into skin, or can refer to the overall length of the fiber leading from the light source.

Likewise, any diameter needle can also be used in accordance with the present invention, including needles that are 300 microns or less in diameter at any point on the needle. Preferred needle embodiments have a base diameter ranging from about 50 microns to about 500 microns and any diameter in that range. More specifically, preferred needle embodiments of the invention have a base diameter of about 100 microns to 200 microns, such as from about 140 microns to 175 microns, and such as from about 150-170 microns. Tip diameters of the needles of the invention can range from about 1 micron to 50 micron, such as from about 2-20 micron, such as from about 5-15 micron, or from about 3-12 micron, or any diameter in that range. If the needle has a hollow core (or liquid-filled core), then these diameter ranges are also applicable to the inside diameter of the core.

Preferred microneedles according to the invention include needles having a length ranging from about 500 to 1000 µm and a tip diameter ranging from about 5 to 10 µm, and longer microneedles (about 2 to 4 mm) with smaller tip diameters (about 2-8 µm). Specific needle embodiments of the invention comprise fiberoptic microneedles with 125 µm root diameter and 2-8 µm tip diameter.

The needles can be solid throughout or comprise a hollow core. When referring to diameters in this disclosure, it is typically intended to refer to outer diameters of the needles, whether measured at the base or tip of the needle. In some cases a diameter mentioned may refer to the inner diameter of the hollow core of the needle.

The microneedles of the invention also comprise a range of acceptable aspect ratios. As used in this disclosure, an aspect ratio refers to the unsupported length of the needle divided by the average cross-sectional diameter of the needle. Another way of determining the aspect ratio for a needle according to embodiments of the invention is to use the minimum outer diameter of the needle in combination with the unsupported length of the needle. Preferred aspect ratios of microneedles, e.g., fiberoptic microneedles, of the invention range from about 21 to 85. Using these high aspect ratio microneedles to penetrate skin is a challenge due to possible failure by buckling under the skin's resistance. However, earlier studies have found that the skin insertion force ($F_{INS}$), the force which the microneedle is subjected to during insertion into the skin, varies linearly with the cross-sectional area of the tip. See, Davis, S. P., et al., 2004 "Insertion of Microneedles into Skin: Measurement and Prediction of Insertion Force and Needle Fracture Force," Journal of Biomechanics, 37(8), pp. 1155-1163, the disclosure of which is incorporated by reference herein in its entirety.

Figures 3, 3A, 3B, 3C:
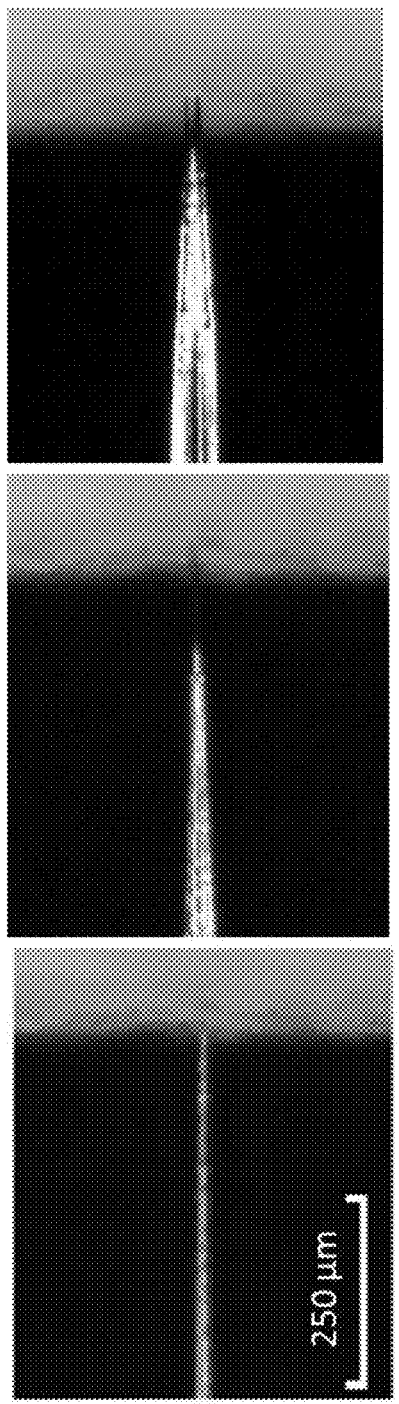
FIGS. 3A-C are a series of photographic images of a microneedle according to the invention that is inserted into skin at 0 mm, 0.5 mm, and 1 mm depths.

Microneedles were tested for their ability to penetrate mediums with different hardness. Needle penetration into skin was performed with porcine skin obtained from a local butchery. The microneedle used was able to penetrate the skin up to a 1 mm depth without breaking, which is a sufficient depth to bypass the epidermal layer of the skin, which scatters the most light. FIGS. 3A-C show photographic images of needle penetration into skin at 0 mm, 0.5 mm, and 1 mm, respectively.

Figure 4:
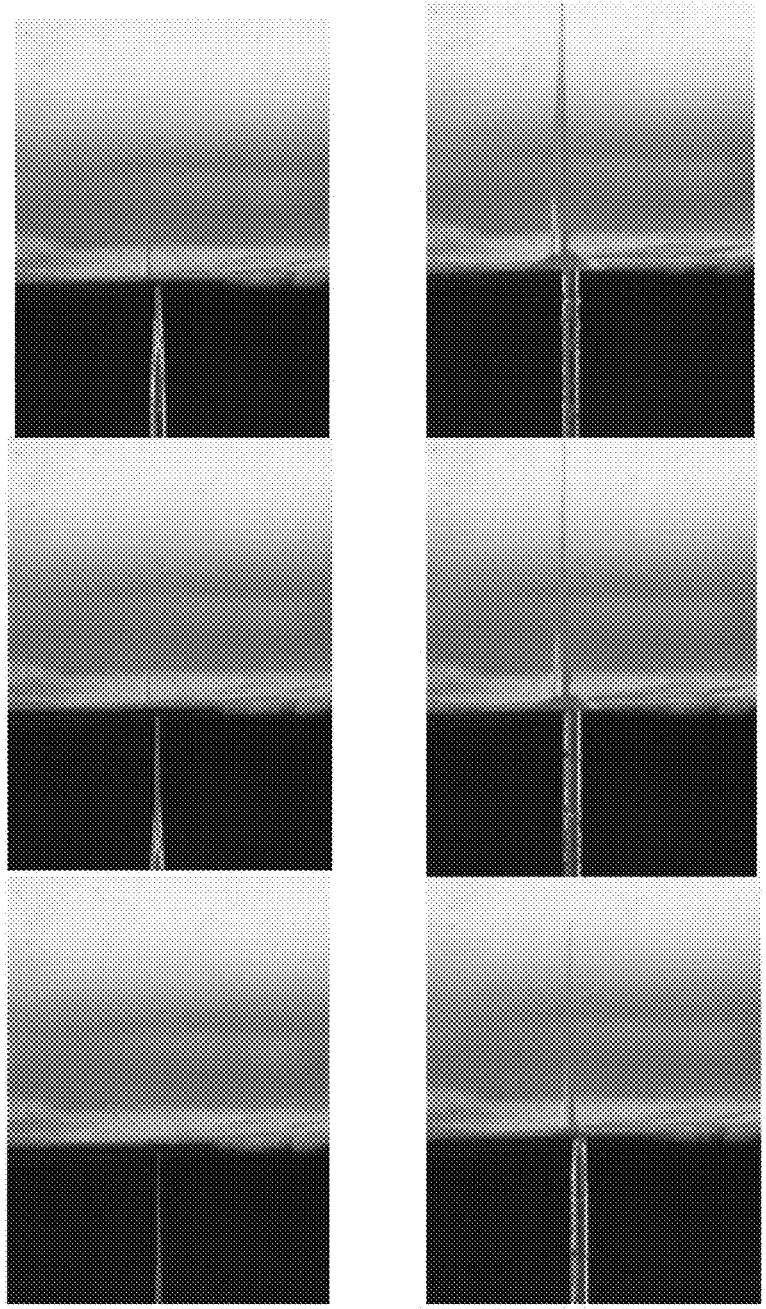
FIG. 4 provides a series of photographic images of a microneedle according to the invention inserted into skin at various intervals.

Additionally, a microneedle was placed on a micrometer translational stage, and it was manually inserted into a slice of store bought flavorless gelatin. FIG. 4 shows insertion of the microneedle into the medium at snapshots taken with 500 µm intervals. The needle was inserted into 2.5 mm depth without bending or any kind of skewing and remained intact even after withdrawal from the gelatin, which demonstrates that these light guiding microneedles are capable of penetrating into soft material.

Modifying the tip of the optical fiber to resemble a sharp needle would reduce the skin insertion force $F_{INS}$ while the critical buckling force ($F_{CR}$) would remain roughly the same. Through this method, skin penetration performance of hollow silicon microneedles has been improved by incorporating ultra-sharp tips with diameters of less than 1 µm. See, Roxhed, N., et al., 2007, "Penetration-Enhanced Ultrasharp Microneedles and Prediction on Skin Interaction for Efficient Transdermal Drug Delivery," Journal of Microelectromechanical Systems, 16(6), pp. 1429-1440, the disclosure of which is incorporated by reference herein in its entirety. In addition to decreasing $F_{INS}$, a sharp tip also modifies the forcing conditions on a microneedle during insertion.

In a recent study, a comparison of the penetration of ex vivo human skin by flat versus sharp-tipped punches was presented. See, Shergold, O. A., and Fleck, N. A., 2005, "Experimental Investigation into the Deep Penetration of Soft Solids by Sharp and Blunt Punches, with Application to the Piercing of Skin," Journal of Biomechanical Engineering-Transactions of the Asme, 127(5), pp. 838-848, the disclosure of which is incorporated by reference herein in its entirety. The flat punches were made from 300 and 500 µm thick stainless steel wires while 300 and 600 µm thick hypodermic needles were used as sharp punches. The results showed that penetration by sharp punches was accompanied by a growing mode I planar crack which caused a steady increase in the force. In contrast, the resistive force on the flat punches showed a rapid increase followed by an instant drop as the punch penetrated through the different skin layers due to the formation of a mode II ring crack. Considering the lower $F_{INS}$ and steadier force increase on sharp microneedles, sharp tips would make thinner, less invasive microneedles mechanically practical for penetrating skin.

Needle geometry can be varied to achieve particular desired effects and/or results. For example, the leakage length of fiberoptic microneedles (the axial length of the microneedle, along which the laser light leaks out of the microneedle and into the surrounding medium) can vary according to the taper length of the needle.

Figure 5:
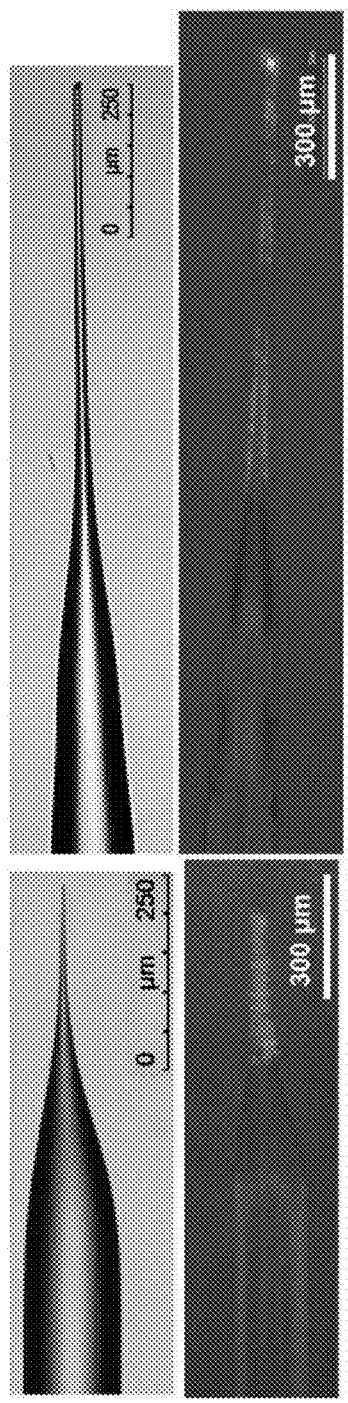
FIG. 5 provides brightfield microscopy images of two microneedles according to the invention having different taper lengths and color microscopy images of those needles delivering red laser light in air, demonstrating different leakage lengths for the needles.

The leakage length of several fiberoptic microneedles in air was measured in order to evaluate the importance of the microneedle geometry. In particular, various fiberoptic microneedles with differing taper lengths were used to deliver red laser light in air (FIG. 5). More particularly, FIG. 5 provides brightfield microscopy images of two microneedles according to the invention having different taper lengths and color microscopy images of those needles delivering red laser light in air. As shown, different needle geometries can provide different leakage lengths for the needles.

Table 2 lists values for taper and leakage lengths of various microneedles according to embodiments of the invention:

TABLE 2

Taper Lengths and Leakage Lengths for Various Microneedles

| Microneedle | Taper Length [µm] | Leakage Length [µm] |
|---|---|---|
| 1 | 380 | 177 |
| 2 | 1550 | 950 |
| 3 | 460 | 204 |
| 4 | 410 | 319 |
| 5 | 387 | 227 |
| 6 | 431 | 224 |
| 7 | 457 | 154 |
| 8 | 396 | 193 |
| 9 | 929 | 490 |
| 10 | 398 | 190 |

Figure 20:
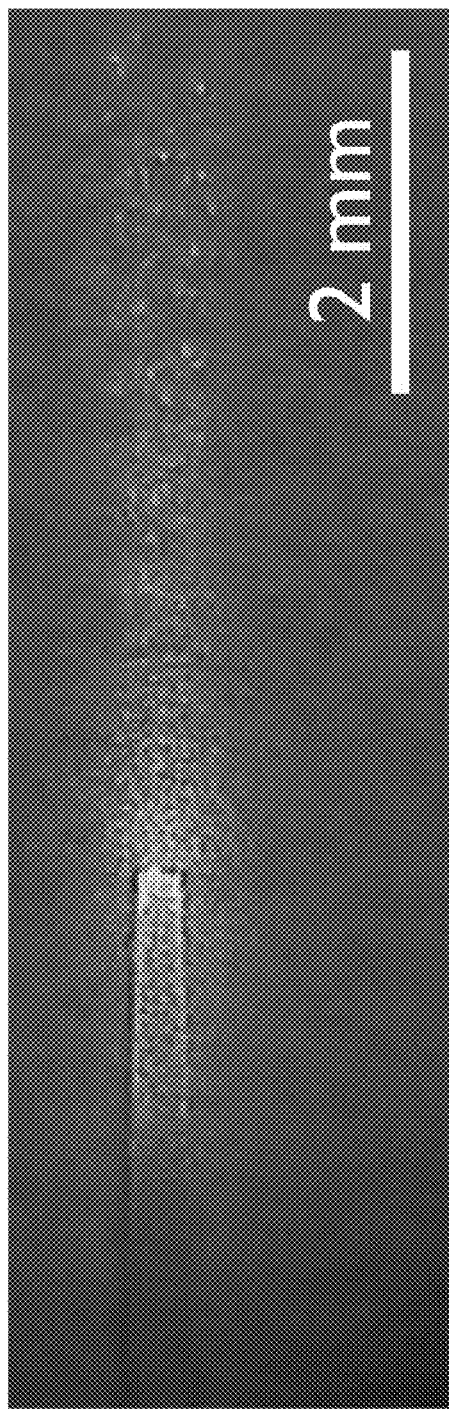
FIG. 20 is a photographic image of a light leaking microneedle.
Figure 21:
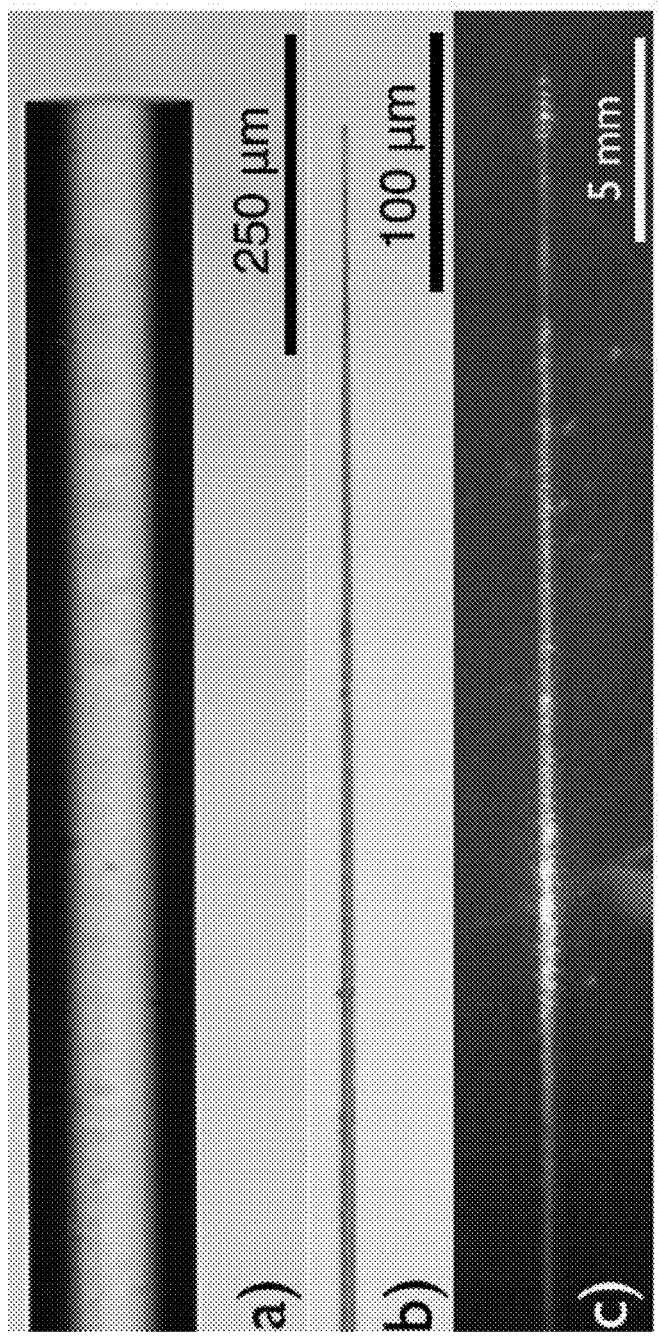
FIGS. 21A, 21B, and 21C are brightfield microscopy images showing the control of microneedle leakage length by removing the fiber cladding by HF etching.

Leakage length of fiberoptic microneedles varied according to their taper length. Longer tapers resulted in longer leakage lengths. Leakage length can be controlled by removing the fiber cladding by polishing. Fibers with larger core/cladding ratio and larger taper angles produce a longer leakage length. Leakage area of light can be controlled by changing the geometry of the fiberoptic microneedle. For example, a longer leakage length can be useful for delivering laser light along the shaft of a hair follicle while shorter leakage length limits the loss of light and provides deeper light penetration. Said another way, for certain therapeutic applications such as fat removal, a shorter leakage length causing a more forward-focused beam from the needle may be desirable, however, for hair removal applications, a more uniformly diffuse optical delivery to heat the vertical sides of the hair follicles is preferred and therefore longer leakage length needles may be desirable. Controlling the leakage length by removing the fiber cladding by polishing. As shown in FIG. 20, light leaking microneedles were manufactured by polishing the sides of a multimode optical fiber and removing the cladding. As shown in FIGS. 21A, B, and C, leakage length can be controlled by removing the fiber cladding by HF etching. In particular, a light leaking microneedle was manufactured by dipping a multimode optical fiber into a %48-50 HF solution for about an hour.

In embodiments, etching of the optical fiber can be desirable for the dual effect it provides, namely, a sharp needle tip and removal of light blocking material from the outside of the needle. A sharp tip provides for increased penetration into tissue, while removal of light blocking material from the needle allows light to diffuse circumferentially from the needle. In certain applications, especially where less carbonization of tissue is desired, a more diffuse light irradiating from portions of the axial length of the needle may be desired instead of all or most of the light irradiating from the end of the needle.

Any optical fiber can be used to make needle embodiments of the invention. It is not critical that the core or cladding material be of any particular material or configuration. For example, the core and cladding typically comprise materials with different refractive index characteristics to trap all or most of the light within the area bounded by the cladding and to ensure transmission of light through the core of the needle. Depending on the cladding material and/or whether the needle is coated with a light blocking material, some light may escape resulting in leakage horizontally through the needle instead of mostly vertically through the tip of the needle. In some applications horizontal leakage may be desired.

Light guiding microneedles were manufactured from optical fibers with 8 µm diameter silica core and 125 µm diameter silica cladding. These optical fibers were drawn down into a tapered (needle-like) shape by simultaneously heating the fiber to its melting temperature and stretching it with a mechanical stage. Heating of the optical fiber was done by two different methods, thereby producing microneedles with different geometries. Needles can be prepared in other ways as well, including physically sharpening the end of the optical fiber until a desired tip is formed. Likewise, the end of the fiber can be chemically etched to remove a portion of the fiber material from the needle, for example, by reducing the outside diameter of the needle by acid etching. The needles can also be prepared by heating the tip of the needle to a degree sufficient to allow bending of the needle into a desired angular position.

Figure 6:
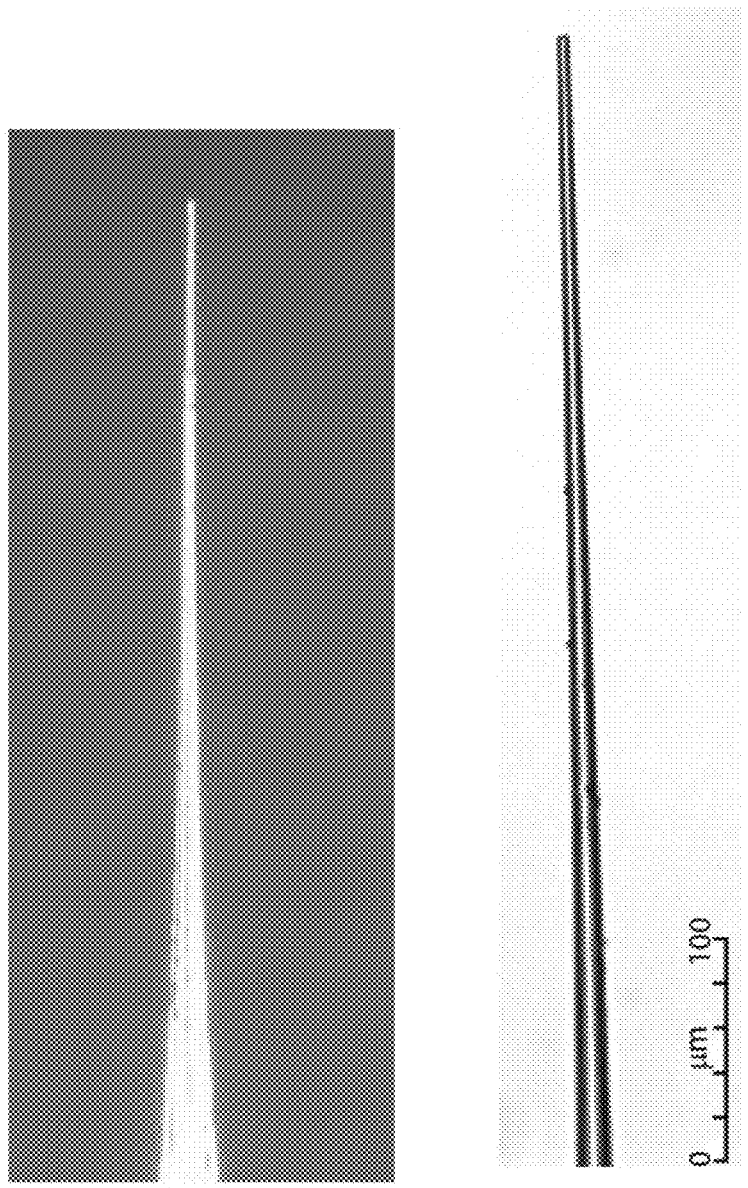
FIG. 6 shows photographic images of an embodiment of the inventive light guiding microneedles according to the invention.

Some microneedles were manufactured by heating the fiber by focusing the beam of a $CO_2$ laser on the fiber. As shown in FIG. 6, this method produced microneedles with lengths ranging from 500 to 1000 µm and with tip diameters of 5 to 10 µm. Longer microneedles (2 to 4 mm) with smaller tip diameters (2-8 µm) were obtained by placing half of a sapphire tube underneath the fiber and heating the tube with a propane-oxygen torch. The heat radiating from the tube softened the fiber slowly and made it possible to manufacture longer microneedles with smaller taper angles and smaller tip diameters.

In order to increase the effective deployment angle of arborizing fiberoptic microneedle devices while staying within the generally accepted maximum cannulus diameter of 3 mm, a curved needle is preferred. Heat treatment has been shown to achieve suitable curvature in the polyimide jacketed, hollow-core, optically transparent silica fibers.

In order to impart the desired coil shape on the fiber, one or more lengths are fed into a thin copper tube (⅛" OD, ¼ ID), which is then tightly coiled around a steel rod. This assemblage is then placed on a hot plate preheated to 400° C. The copper tubing and steel rod can also be covered in aluminum foil to serve as insulation. A second layer of aluminum foil is then molded to the coil and surrounding plate, making a small pocket which sits over the assembly. This is removed from the hot-plate after 50 minutes and allowed to cool to approximately room temperature (~25° C.) before the copper tube is uncoiled. If an insufficient length of fiber is extending beyond the end of the copper tube to allow removal by pulling, a short length of the tubing is removed with a pipe-cutter, and the fiber is carefully removed, cut to length, and polished for use.

The polyimide jacketing begins to degrade at ~500° C. The time heated and hot plate temperature have been chosen as they have consistently yielded fiber with a significant curvature. It is currently unknown whether the imparted curvature is due to plastic deformation in the silica fiber, polyimide jacket, or a combination thereof. However, the current hypothesis is that melting/softening of the polyimide jacket while curved followed by re-hardening is causing the relaxed state curvature. The fiber's overall curvature is a function of the combination of heating temperature, heating time, and fixation radius.

Fiberoptics.

A method with which to increase the arborization angle of either solid or hollow core fiberoptics with a polyimide jacket is through creating innate curvature. This can be accomplished through heat treatment while being bent to a desired angle. Heating from 300-400° C. for a period of time from a few minutes to hours can cause the fibers to a reach varying degrees of a curved relaxed state. This curvature allows the fibers to be more easily extruded and retracted at a desired angle from the central sheath. Additionally, the curvature allows a shorter length to be extruded from the sheath to reach a desired tip to tip spread between the arborizing fibers.

Figure 59:
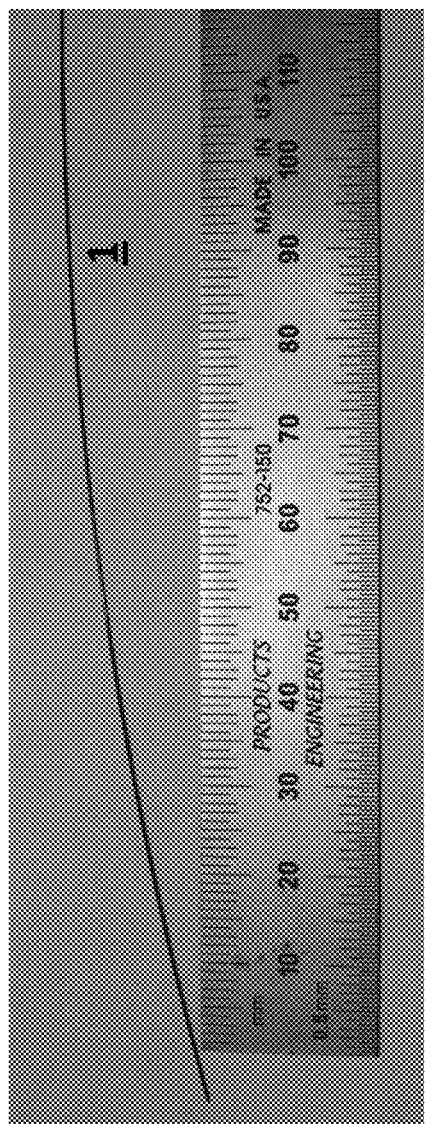
FIG. 59 is a photograph showing a fiber curved by heat-treatment.

FIG. 59 shows a fiber curved by heat-treatment. The fiber was heated at 400° C. for 50 minutes. As discussed above, any amount of heat can be used so long as it is sufficient to render the needle material bendable and so long as it does not lead to degradation of the material. It is within the skill of the art to heat the material for a time sufficient to achieve the desired amount of bending. Further, all or part of the fiber can be bent with heating and the bend can be imposed gradually along the length of the needle or abruptly at a certain point.

Figure 60:
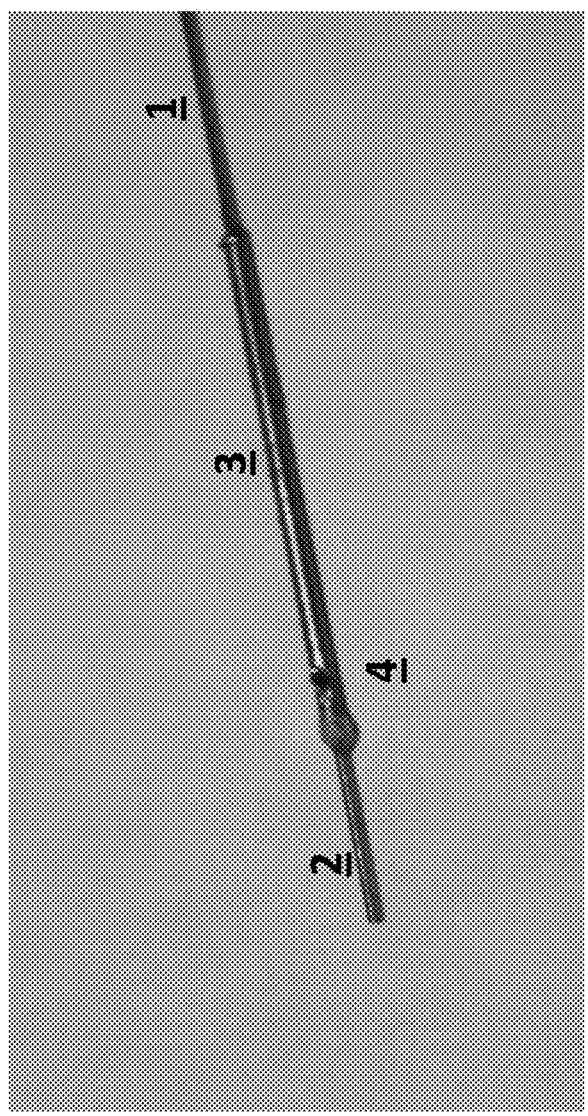
FIG. 60 is a photograph showing an embodiment of an FMD for removing fat.

FIG. 60 shows an embodiment of an FMD for removing fat. Light is brought into the sheath (3) by the solid core fiber (1) at the right and meets the hollow core microneedle (2) directly over the sideport (4). The hollow core microneedle can be inserted into fatty tissue. Following liquefaction, fat enters the needle at the left side and exits the sideport in the sheath.

Fiberoptic microneedles can be prepared from any material capable of transmitting light, with silica-based optical fibers being a preferred starting material. Light-guiding fiberoptic microneedles were manufactured from two kinds of commercially available, silica based, step-index optical fibers. The optical fibers were drawn into thinner fibers by simultaneously heating them to the melting temperature of silica (1650±75° C.) and stretching them with two mechanical stages (0.2-0.36 mm/sec drawing speed). Heating was provided by a heat-radiating sapphire tube, which was carefully placed around the fiber without any contact. The dimensions of the sapphire tube were 4 mm inner diameter, 6 mm outer diameter, and 8 mm length. A propane-oxygen torch was used to heat the sapphire tube. At this point in the process (Step I), the optical fiber had a thinner section toward the middle of the fiber, whereby the overall shape of the fiber resembled an hourglass shape. Depending on the duration of the tapering process, this thinner section varied between 6-8 mm in length. If the stretching and heating of the fiber was continued until the fiber broke apart at its thinnest cross-section, then two microneedles were produced with flat tips (referred to as flat microneedles).

To obtain lower $F_{INS}$ and steadier increase in the peak force, microneedles with sharp tips were manufactured. In order to produce microneedles with sharper tips, the heating and stretching of the fiber was halted before breaking the fiber. An additional step was then performed (Step II), a $CO_2$ laser ($\lambda$=10 µm) was focused onto the center of the narrow section of the fiber before continuing to stretch the optical fiber at a velocity of 0.05-0.1 mm/sec. Such rapid and focused heating produced a second taper, resulting in a sharper tip ($d_{TIP} \leq 8$ µm). The sapphire rod heated the optical fibers over a length of 8 mm while the $CO_2$ laser had a spot size of 400 µm in diameter.

Figure 7:
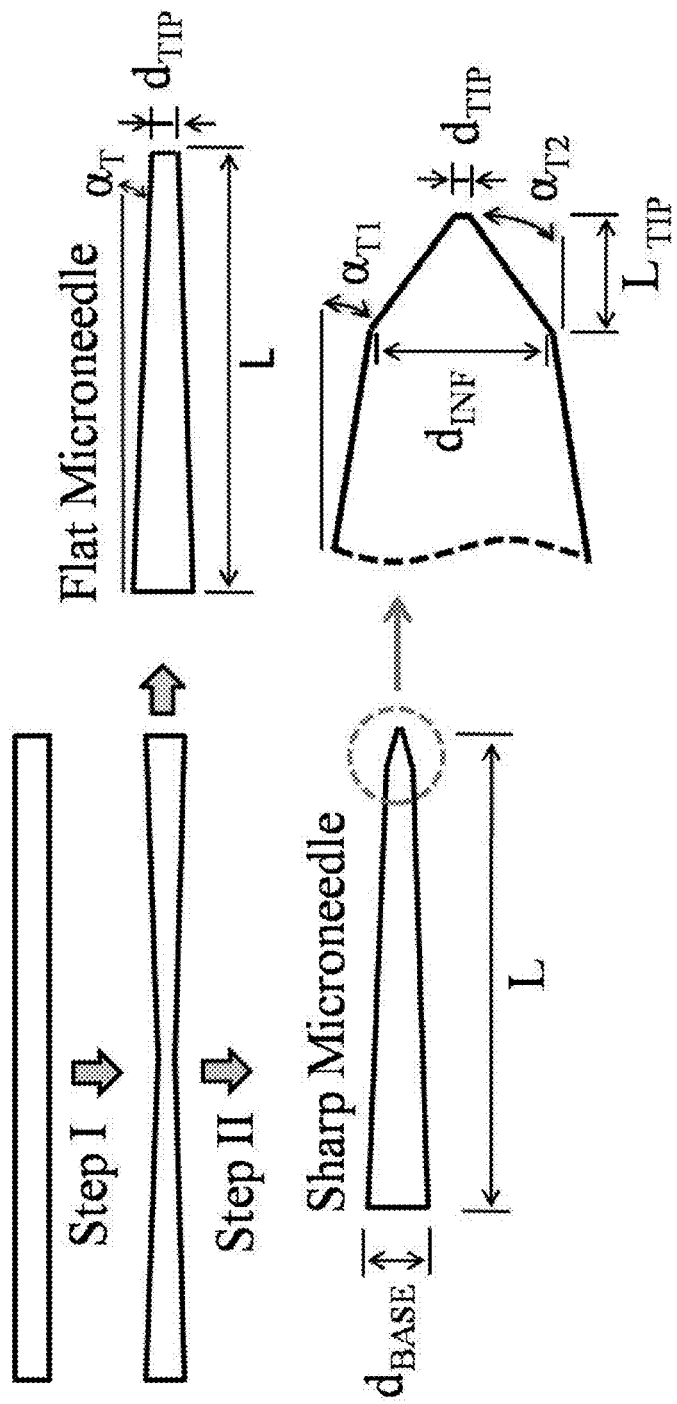
FIG. 7 is a schematic diagram of a manufacturing process for microneedles according to exemplary embodiments of the invention.

FIG. 7 shows a schematic of a manufacturing process for fiberoptic microneedles according to the invention and geometric parameters of both kinds of microneedles, i.e., flat-tip and sharp-tip needles. As shown, the fiber optic material is heated and stretched (Step I), which results in an overall hourglass shape in the material. For a flat tip, the hourglass shaped material is caused to break forming two flat-tip microneedles. For a sharp tip (Step II), the material is stretched and heated and focused heat is applied at a point in the material where it is desired to have a tip, typically at a mid point of the material during stretching. The heat can be provided by a $CO_2$ laser ($\lambda$=10 µm) and is applied with continued stretching of the material at a desired rate to cause the optical fiber to break while forming a second taper at the tip of the microneedle, which is referred to as a sharp tip due to the additional taper.

Figure 8:
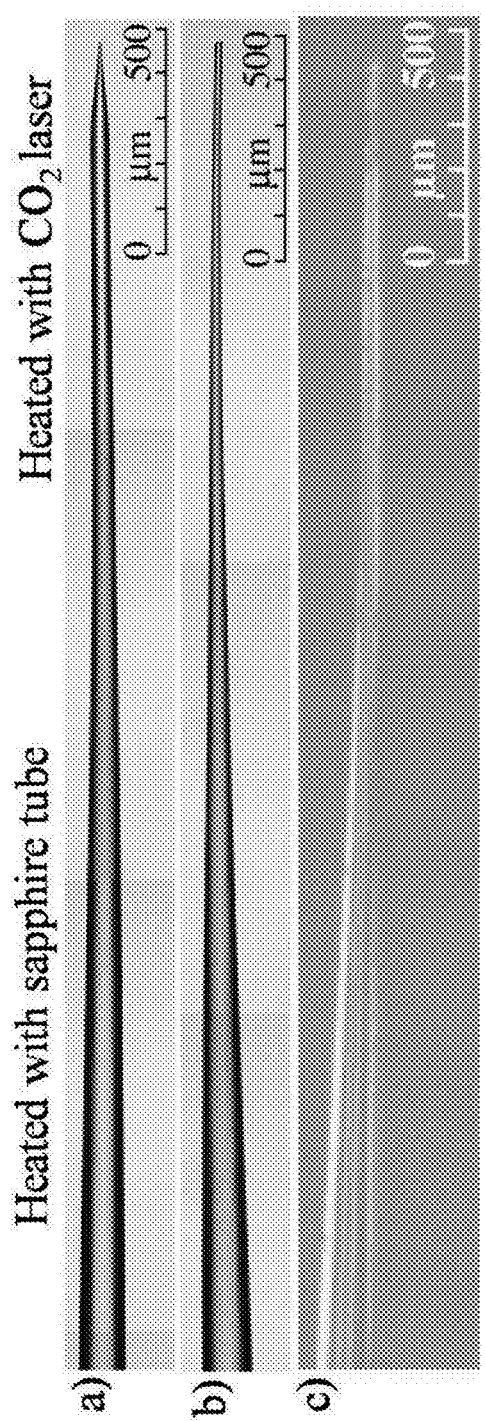
FIGS. 8A and 8B are, respectfully, brightfield images of a sharp and a flat microneedle prepared according to processes of the invention.
FIG. 8C is a color microscope image of a sharp microneedle of an embodiment of the invention, shown delivering red laser light.

FIGS. 8A and 8B are brightfield images of a sharp and a flat microneedle prepared according to processes of the invention, respectively. FIG. 8C is a color microscope image of a sharp microneedle delivering red laser light near the tip ($\lambda$=633 nm).

Eight flat microneedles (F1-F8) and twelve sharp microneedles (S1-S12) were manufactured. Microneedles F1 through F4 were manufactured as explained in Step I of the above-described process. Microneedles F5 through F8 were manufactured by flat-cleaving optical fibers and had no melt-drawing applied. Microneedles S1 through S10 were manufactured by the two-step melt-drawing process (Step I and II) described above. Microneedles S11 and S12 were manufactured using only $CO_2$ laser heating (Step II) as described above. Microneedles S11, S12, and F5, were made from single-mode fiber (8±0.7 µm core/125±0.7 µm cladding), while all other microneedles were manufactured from multi-mode optical fiber (125±5 µm silica core/140+2/-5 µm silica cladding).

For flat microneedles with linearly varying cross-sectional diameters, an average diameter ($d_{AVG,FLAT}$) can be defined by Eq. (1):

$$d_{AVG,FLAT} = \frac{d_{BASE} + d_{TIP}}{2} \qquad (1)$$

In Eq. (1), the base diameter ($d_{BASE}$) is the thickness of the microneedle 3 mm from its tip. The tip diameter ($d_{TIP}$) is the diameter of the tip. The taper angle of the flat microneedles is calculated by Eq. (2):

$$\alpha_T = \tan^{-1}\left(\frac{d_{BASE} - d_{TIP}}{2L}\right) \qquad (2)$$

In Eq. (2), L is the unsupported length and was equal to 3 mm (±0.1 mm uncertainty) for all microneedles.

For sharp microneedles, the two taper angles are given in Eq. (3) and Eq. (4):

$$\alpha_{T1} = \tan^{-1}\left(\frac{d_{BASE} - d_{INF}}{2(L - L_{TIP})}\right) \quad (3)$$

$$\alpha_{T2} = \tan^{-1}\left(\frac{d_{INF} - d_{TIP}}{2L_{TIP}}\right) \quad (4)$$

The inflection diameter ($d_{INF}$) is the thickness of the microneedle at the junction of the first and second taper. Tip length ($L_{TIP}$) is the length of the second taper for sharp microneedles. In the second taper section of the microneedle, the taper angle ($\alpha_{T2}$) increases. The distance from the base to the junction point of two different tapers ($L-L_{TIP}$) equaled 88% to 94% of the full length of the microneedle.

For the sharp microneedles, $d_{AVG,SHARP}$ was defined as in Eq. (5):

$$d_{AVG,SHARP} = \frac{d_{BASE} + d_{INF}}{2} \quad (5)$$

For calculation of sharp microneedle average diameter, $d_{TIP}$ is replaced by $d_{INF}$ because the first taper section ($L-L_{TIP}$) is much larger than the second taper section ($L_{TIP}$).

Tables 3 and 4 include the values for geometric parameters of some exemplary microneedles (F1-F8 and S1-S12) according to the invention. For microneedles S11 and S12, $\alpha_{T2}$ provided an equivalent average value for taper angle. The actual taper angle varied along the length of the second taper due to the non-linear behavior of the decrease in diameter.

TABLE 3

Geometric Parameters of Flat Microneedles

| Microneedle | Base Diameter $d_{BASE}$ [μm] | Average Diameter, $d_{AVG}$ [μm] | Tip Diameter, $d_{TIP}$ [μm] | Taper Angle $\alpha_T$ [°] |
|---|---|---|---|---|
| F1 | 61 | 35 | 9 | 0.5 |
| F2 | 103 | 60 | 17 | 0.8 |
| F3 | 113 | 65 | 18 | 0.9 |
| F4 | 132 | 75 | 18 | 1.1 |
| F5 | 125 | 125 | 125 | 0 |
| F6 | 136 | 136 | 136 | 0 |
| F7 | 136 | 136 | 136 | 0 |
| F8 | 139 | 139 | 139 | 0 |

TABLE 4

Geometric Parameters of Sharp Microneedles

| Microneedle | Base Diameter $d_{BASE}$ [μm] | Inflection Diameter $d_{INF}$ [μm] | Average Diameter, $d_{AVG}$ [μm] | Tip Length $L_{TIP}$ [μm] | Tip Diameter, $d_{TIP}$ [μm] | First Taper Angle, | Second Taper Angle, |
|---|---|---|---|---|---|---|---|
| S1 | 63 | 24 | 44 | 207 | 3 | 0.4 | 2.9 |
| S2 | 88 | 22 | 55 | 189 | 5 | 0.7 | 2.7 |
| S3 | 105 | 22 | 63 | 164 | 4 | 0.8 | 3.1 |
| S4 | 120 | 14 | 67 | 221 | 4 | 1.1 | 1.4 |
| S5 | 120 | 14 | 67 | 201 | 4 | 1.1 | 1.5 |
| S6 | 119 | 22 | 70 | 190 | 4 | 1.0 | 2.7 |
| S7 | 125 | 15 | 50 | 221 | 4 | 1.1 | 1.4 |
| S8 | 104 | 41 | 73 | 175 | 8 | 0.6 | 5.4 |
| S9 | 119 | 27 | 73 | 211 | 4 | 0.9 | 3.2 |
| S10 | 121 | 56 | 89 | 262 | 2 | 0.7 | 5.9 |
| S11 | 125 | 125 | 125 | 308 | 8 | 0.0 | 10.7 |
| S12 | 125 | 125 | 125 | 365 | 6 | 0.0 | 9.3 |

Figure 22:
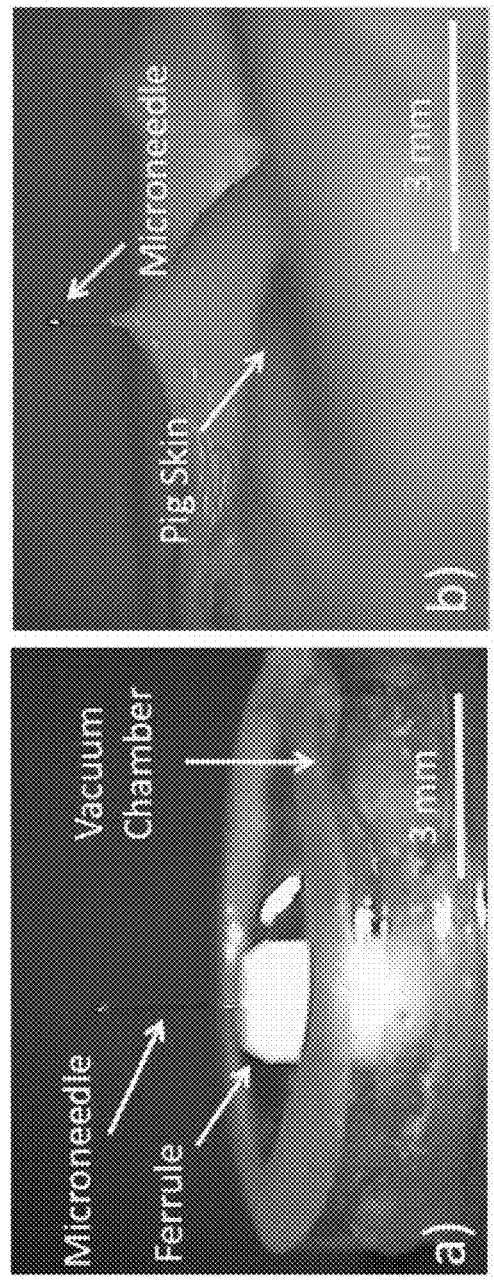
FIGS. 22A and 22B are photographic images of a) Vacuum chamber, ferrule, and the fiberoptic microneedle; b) Fiberoptic microneedle penetrating 2 mm thick pig skin.

The 20 microneedles were tested for skin penetration capability by inserting the needles through skin samples that were fixed above a U-Channel. All of these microneedles had the same unsupported length of 3 mm (i.e., the microneedles were fixed inside a steel tube with a 3±0.1 mm unsupported length by application of adhesive on their base). The microneedles were positioned 1 mm or less away from the surface of the skin and then translated into the skin with a velocity of 0.5 mm/sec until penetration or buckling occurred. Microneedle displacement and penetration force were measured during insertion into the pig skin samples using a BOSE™ Electroforce™ 3100 mechanical testing instrument. This instrument has 1.5 μm displacement resolution over its 5 mm range. FIGS. 22A and B are photographic images of a) Vacuum chamber, ferrule, and a fiberoptic microneedle; b) Fiberoptic microneedle penetrating 2 mm thick pig skin.

Flat microneedles F5 through F8 and sharp microneedles S8 through S12 were able to penetrate pig skin. For sharp microneedles ($d_{TIP}$=2-8 μm), successful penetration was achieved by microneedles with $d_{AVG}$=73-125 μm, or said another way, a minimum average diameter of 73 micron and a maximum tip diameter of 8 micron. Further, for example, the microneedles of embodiments of the invention can have a minimum outer diameter of about 25-150 μm, such as 30-70 μm, or 35-50 μm, for example, at regions of the fiber other than the tip. Flat microneedles prepared by the flat-cleaving process also successfully penetrated skin with $d_{AVG}$ between 125 to 139 μm. Flat microneedles, which had larger tip diameters, required a minimum average diameter of 125 micron in order to penetrate through pig skin samples. Flat microneedles that were able to penetrate were larger in average diameter (125 to 139 μm) in comparison to sharp microneedles (73 to 125 μm).

The taper angle of the microneedles was low ($\alpha_{T1}$=0-1.1°). Thus, the critical buckling force, $F_{CR}$ of the microneedle can be approximated by Euler's buckling formula for a cylindrical column with one fixed end and one free end, which is given in Eq. (6);

$$F_{CR} = \frac{E\pi^3 d_{AVG}^4}{256\, L^2} \quad (6)$$

In Eq. (6), E is the elastic modulus of silica. This formula indicates that $F_{CR}$ is dependent to the fourth order on $d_{AVG}$.

Thus, a 50 percent reduction in the thickness to produce less invasive microneedles limits the mechanical strength by a factor of 16.

Two attributes were likely to contribute to the success of the sharper yet thinner microneedles. First, the range of peak forces that occurred during penetration of sharp microneedles (234±110 mN to 646±6 mN) was much less than the range for flat microneedles (692±6 mN to 1350±110 mN). Second, the change in the force during penetration was steadier for sharp microneedles compared to the flat microneedles.

This is because sharp microneedles likely penetrated through the skin by forming a planar mode I crack as explained in the literature. See Shergold 2005. During insertion of microneedles S8, S10, S11, and S12, the force increased and decreased without any sudden drops. Flat microneedles likely penetrated the skin by forming a mode II ring crack, and the microneedles penetrated through the skin with jerky movements which caused sudden drops in the force. See Shergold 2005. Thus, our experiments showed that the change in penetration mechanics is evident even though the diameters of the microneedles used in this paper (ranging from about 73 to 139 μm) were much smaller than the punches (300 to 600 μm) used in the Shergold experiments.

For clinical applications, other considerations are instructive. Besides discomfort and bleeding, another harmful side effect might be caused by small silica particles that break off from the microneedles inside or underneath the patient's skin. To ascertain the possibility of microneedle breakage, images of microneedles before and after insertion were recorded and compared. Flat microneedles that successfully penetrated pig skin samples sustained no visible microscopic damage. Sharp microneedles S9, S10, and S12 with smaller tips ($d_{TIP}$=2-6 μm) were damaged along their tips. In contrast, microneedles S8 and S11, which had relatively larger tip diameters ($d_{TIP}$=8 μm), remained intact during and after penetration of skin. Accordingly, the geometry of S8 and S11 may be preferred for optimizing the shape of the fiberoptic microneedles for safe clinical use.

Embodiments of the present invention comprise a microneedle and a device for supporting the microneedle during use to facilitate penetration of the needle into skin and without breakage (or other failure) of the needle during use, otherwise referred to as a hand-held microneedle injection device. More than one needle can be supported by the tool, however, a preferred embodiment comprises a single needle approach.

Figure 2:
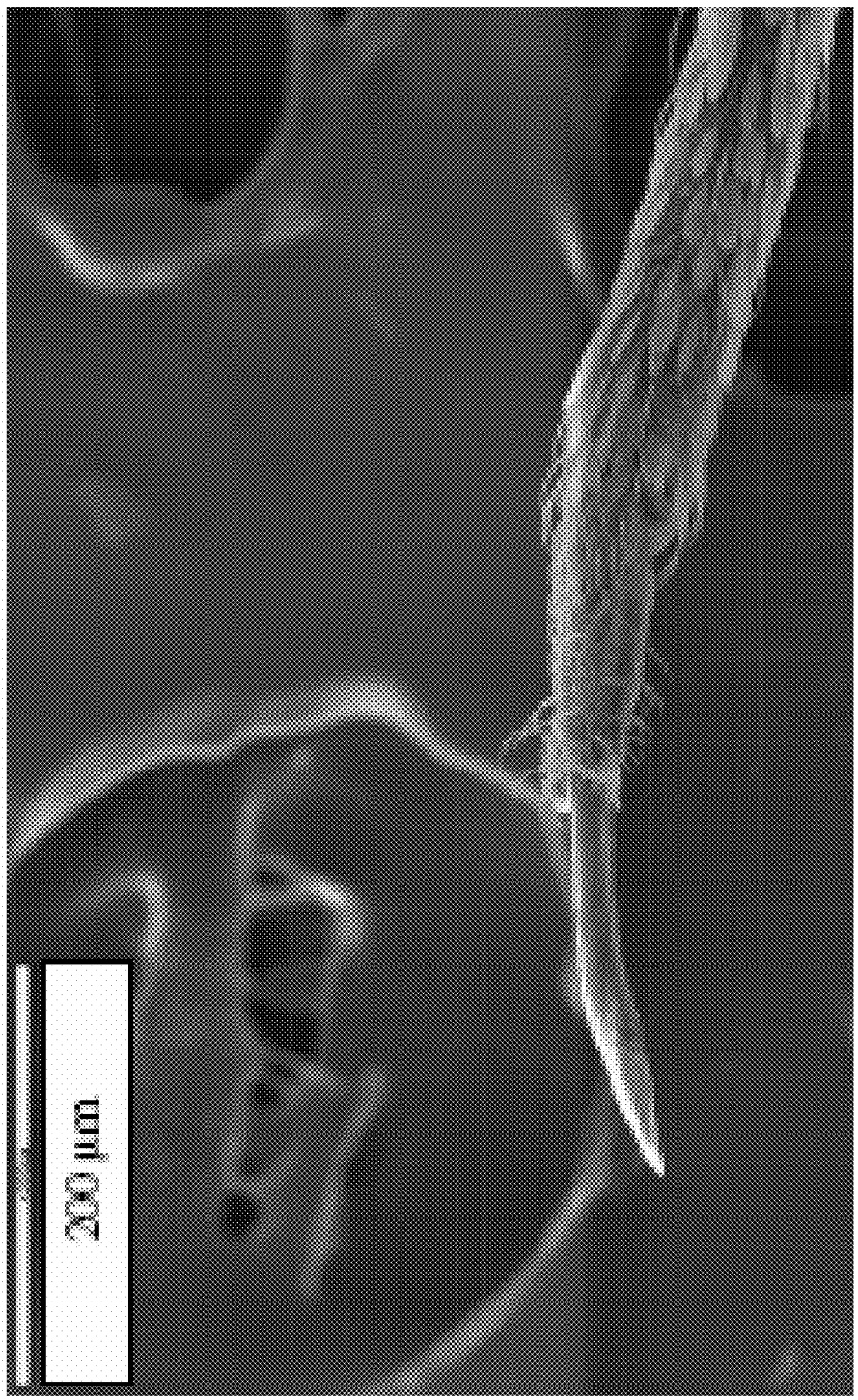
FIG. 2 is a photographic image of a mosquito fascicle and supporting labium.
Figure 9:
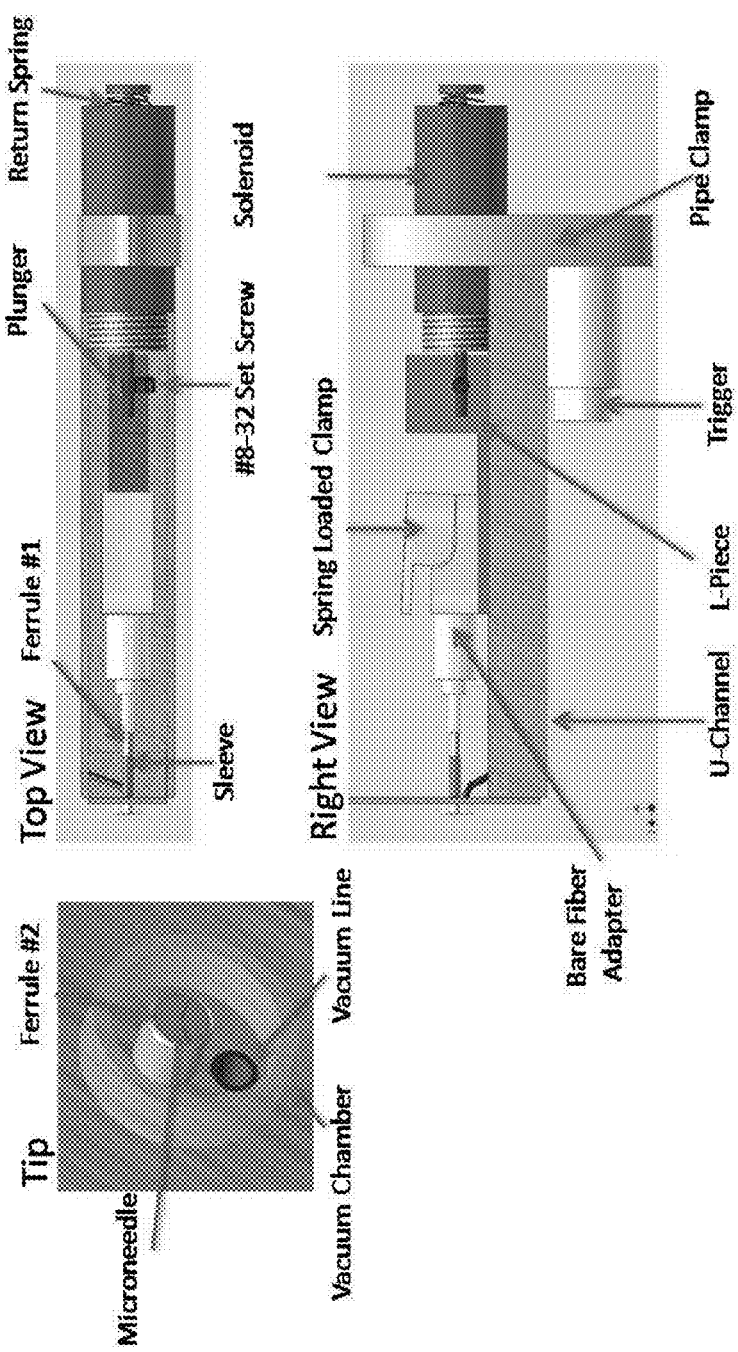
FIG. 9 is a schematic diagram of a hand-held microneedle insertion device according to an embodiment of the invention.
Figure 18:
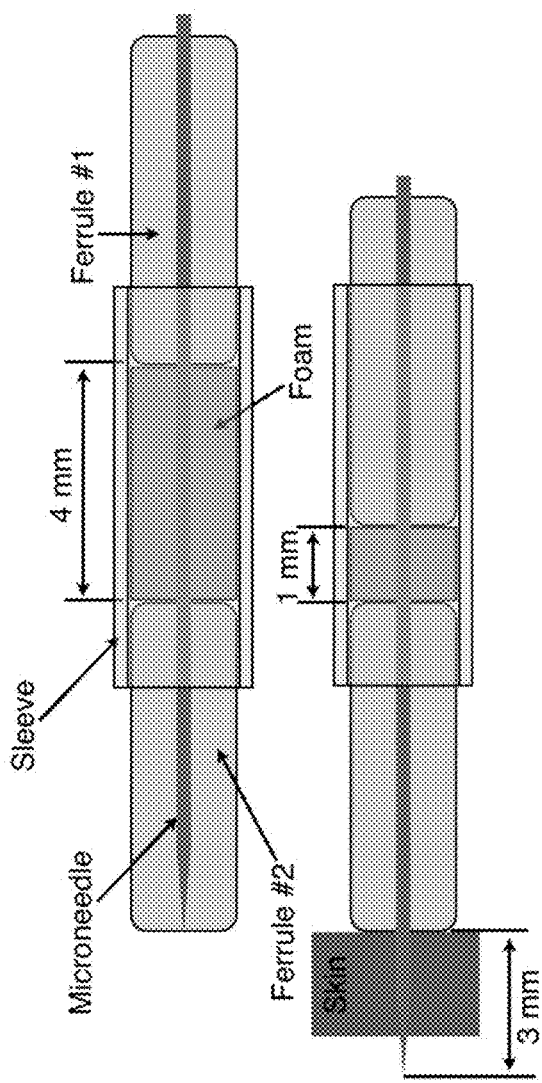
FIG. 18 is a schematic diagram showing an embodiment of the invention which provides a microneedle device (e.g., a fiberoptic microneedle device or FMD).
Figure 19:
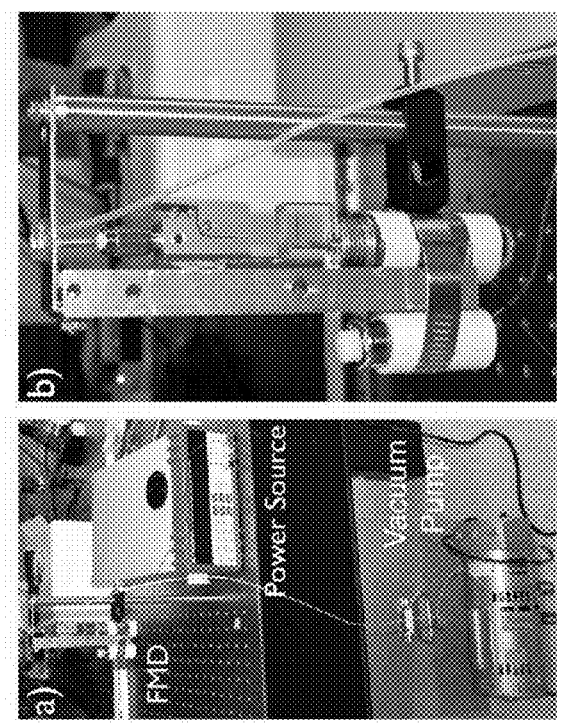
FIGS. 19A and 19B are photographic images showing a) Overview of an FMD setup and b) Close-up image of an embodiment of the device.

More particularly, FIG. 18 shows an embodiment of the invention which provides a microneedle device (e.g., a fiberoptic microneedle device or FMD) having a push type, spring return solenoid for pushing the microneedle into skin. A magnetic coil inside this solenoid translates a circular pin called the plunger towards the skin when a 12V 3 A DC current is applied. The plunger stops moving when the return spring on the proximal end of the solenoid is compressed. An L-shaped piece connects a bare fiber adaptor to the solenoid. A bare fiber adaptor is a special optical device that is usually used to connect an uncoated and unjacketed optical fiber to an optical system. In embodiments, the bare fiber adaptor is used to hose the optical fiber with the microneedle on its tip. The proximal end of the adaptor is consisted of a zirconia optical ferrule (Ferrule #1) with a 125.5 mm inner diameter and 2.5 mm outer diameter. This ferrule is inserted inside a fiberoptic sleeve from the proximal side. Ferrule #1 slides inside this sleeve freely when the adaptor is moved. Another ferrule (Ferrule #2) is inserted into the sleeve from the distal side of the fiberoptic sleeve. Fiberoptic sleeve aligns the two ferrules in the device to be coaxial. When the solenoid is activated, the fiberoptic ferrule 1 moves closer to the fiberoptic ferrule 2, and the fiber slides through both of them. The tip of the fiber extends away from the distal end of ferrule #2 exposing 3 mm of optical fiber including the microneedle on the tip of the fiber. A cylindrical piece of foam is placed inside the fiberoptic sleeve in order to provide the mechanical strengthening effect. An illustration of the mechanism is given in FIG. 2. A plastic brim was placed around the ferrule in order to produce a vacuum chamber. A schematic diagram of another single needle guide and supporting device is shown in FIG. 9. Further, FIGS. 19A and B provide photographic images showing a) Overview of an FMD setup and b) Close-up image of an embodiment of the device.

To verify the efficacy of the hand-held FMD, microneedles supported by the FMD were inserted into skin samples. More particularly, skin samples 2 mm thick were prepared from the fresh ex vivo abdominal pig skin which was provided by the Virginia-Maryland Regional College of Veterinary Medicine. These skin samples were either clamped around the vacuum chamber of the FMD or just laid loosely on top. A vacuum was applied for 8 seconds which caused the skin to fold into the chamber and stretch over the optical ferrule. The microneedle was pushed against the skin by actuating the solenoid.

The FMD successfully injected the microneedles through the pig skin samples 10 out of 10 times, when the skin was fixed around the vacuum chamber using clamps prior to application of the vacuum. Further, the FMD injected the microneedles through the skin 8 out of 20 times when the skin was loose or not fixed, with the microneedles either buckling or pushing the skin away from the vacuum chamber without penetration through the skin samples in the remaining 12 out of 20 times.

Figure 10:
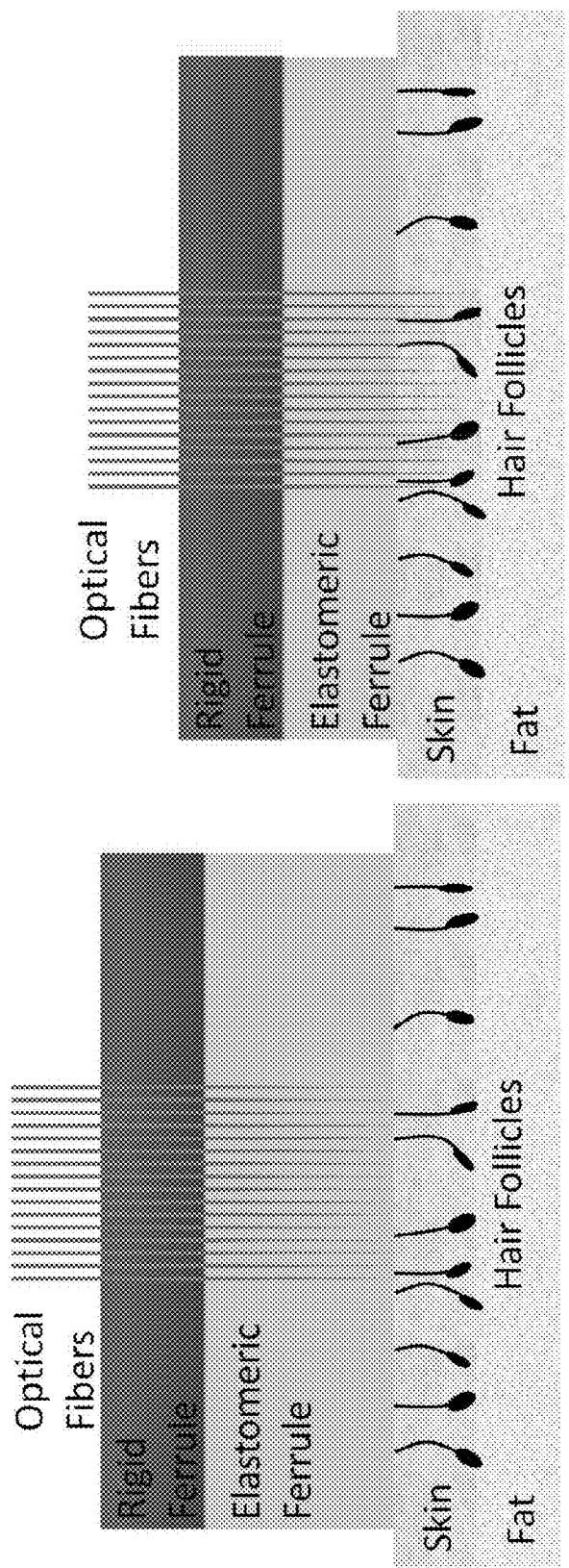
FIG. 10 is a schematic diagram of a microneedle insertion device according to embodiments of the invention.

As shown in the schematic diagram of FIG. 10, other devices for supporting one or more microneedles according to the invention during insertion into skin are also included within the scope of the invention. For example, an array of needles can be used to allow greatly increased light penetration in skin to enable a new regime of deep-tissue light-based therapeutic procedures. In embodiments, a device comprises an array of optically transparent fibers (about 40 microns in outer diameter at the tip) which are guided into a patient's tissue by an elastomeric support ferrule (bushing).

It is known that a mechanical strengthening mechanism for microneedles can be achieved by limiting their lateral movement. See, Khumpuang, S., R. Maeda, and S. Sugiyama, "Design and fabrication of a coupled microneedle array and insertion guide array for safe penetration through skin," in Micromechatronics and Human Science, 2003, MHS 2003: Proceedings of 2003 International Symposium, the disclosure of which is incorporated by reference herein in its entirety. Surrounding the microneedles with an elastic medium such as a polymer may be effective in preventing the microneedles from breaking while being forced into the skin tissue. The positive effect of this mechanism was calculated theoretically. The elastomeric ferrule can optionally be used in conjunction with a rigid ferrule and/or sandwiched between two or more rigid ferrules. The rigid ferrule need not be of a certain rigidity, so long as it is more rigid than the elastomeric portion of the device.

Critical buckling force is the limiting factor for the mechanical strength of these needles because it is the most common mode of failure for long and slender objects under axial stress, such as these microneedles when they are being forced into in vivo tissues. For the simplicity of calculations, the microneedles will be modeled as straight cylindrical columns. The critical buckling force for a straight Euler column is given by formula (7) below:

$$P_{CR} = \frac{C\pi EI}{l^2} \quad (7)$$

where $P_{CR}$ is the critical buckling force, E=50 GPa is the elastic modulus of the microneedle material (Silica in our case) and I is the inertial moment of the cross section. C is a constant that changes between 0.25 and 4 and is determined by the end conditions of the column. If one end of the needle is fixed to the rest of the fiber which is held tightly inside a fiber chuck and the other end is free as it is being injected to the skin, then C can be 0.25.

In embodiments of the invention, surrounding the microneedle, or microneedles in an array of microneedles, with an elastic medium such as a polymer will increase the critical buckling force by limiting the lateral movement of the microneedle. It is assumed here that the elastic medium will act similar to a series of springs with a spring constant that equals the elastic modulus of the material.

The buckling equation for a straight Euler column with a continuous elastic restraint is given in formula (8) below as (See, Wang, C. M., Wang C. Y., Reddy, J. N., "Exact Solutions for Buckling of Structural Members," 2004 CRC Series in Computational Mechanics and Applied Analysis, the disclosure of which is incorporated by reference herein in its entirety):

$$\frac{d^4w}{dx^4} + a\frac{d^2w}{dx^2} + \xi w = 0 \quad (8)$$

where x and w are the non-dimensionalized variables $$x=\bar{x}/L \text{ and } w=\bar{w}/L \quad (9)$$

where L=3 mm is the length of the needle, $\bar{x}$ is the vertical distance from the base, and $\bar{w}$ is the transverse displacement perpendicular to the axis. The buckling force is calculated from the critical load parameter, which is given as;

$$\alpha = P_{CR}L^2/EI \quad (10)$$

The restraint stiffness is calculated as $$\xi = cL^4/EI \quad (11)$$

The value c=2 GPa is the elastic modulus of the surrounding medium, which is a type of polyester, e.g., Nylon.

The range of forces that is needed to penetrate the skin with microneedles has been reported. See, Davis, S. P., et al., "Insertion of microneedles into skin: measurement and prediction of insertion force and needle fracture force," Journal of Biomechanics, 2004, 37(8): pp. 1155-1163, the disclosure of which is incorporated by reference herein in its entirety.

Figure 11:
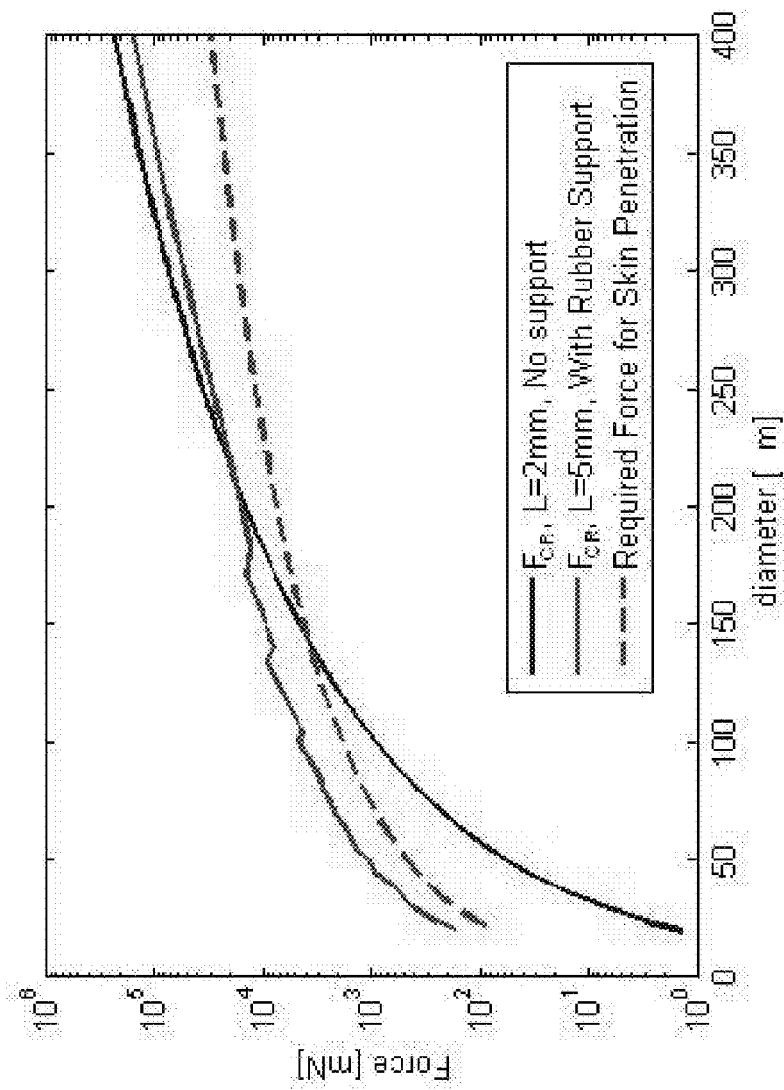
FIG. 11 is a graph of the critical buckling force of microneedles according to the invention of 2 mm and 5 mm in length (with and without additional support means) and the range of forces needed for inserting various diameter needles into skin.

FIG. 11 is a graph showing the minimum and maximum forces that might be needed to penetrate skin, the critical force for buckling of a straight Euler column (without support), and the critical force for buckling of a straight Euler column with a continuous elastic restraint (additional external support means). These forces were calculated for different diameters of microneedles and nanoneedles.

For the case of a straight needle with no elastic restraint, the critical force is quite small. For a 1 μm diameter needle, the critical buckling force is three orders of magnitude smaller than the force needed to penetrate skin. It can be seen from FIG. 11 that a perfectly straight needle made from silica has to be around 100 μm in diameter to be able to penetrate skin. This is the same size as a small optical fiber or small wood splinter, which are known to penetrate skin easily and inflict pain. But the desired condition for the needle is to not induce pain to the patient during insertion, so the diameter of the needle has to be much smaller.

The mechanical strength (critical buckling force) of high aspect ratio (length to diameter) microneedles can be a potential problem in certain applications. Embedding the microneedles in an elastomeric support medium may increase microneedle critical buckling force. For example, to provide a pain-free needle and avoid exceeding the critical buckling force, the needle can be supported by an elastic medium as it is being injected to the skin. This can be achieved in many ways, such as deposition of a liquid polymer around the needles or using a polymer template with small holes of precise dimensions.

The theoretical advantage of such an application is demonstrated by the increased critical stress due to the elastic restraint. The critical force for buckling exceeds the force needed for penetration, even for a 100 nm diameter. A simulation was performed to estimate the critical buckling force of a 5 mm long microneedle inside an elastic support medium ($E_S$=10 MPa) which is reasonably obtained with a soft rubber. For diameters under 200 μm, the critical buckling force of the longer (5 mm) supported microneedle is greater than the buckling force for a shorter (2 mm) unsupported needle. The elastic medium is much softer than the actual needle, but owing to the small diameter of the needle, the surrounding medium acts very stiff relative to the needle, and it is possible to increase the critical buckling force by more than 10× at 40 μm diameter. Additionally, the critical force for buckling of the supported microneedle exceeds the force needed for skin penetration by a factor of ~3× for all diameters used in the simulation. Thus, small and densely packed sub-micron needles with an elastic support can have sufficient strength to penetrate skin without fracture or other failure.

Figure 12:
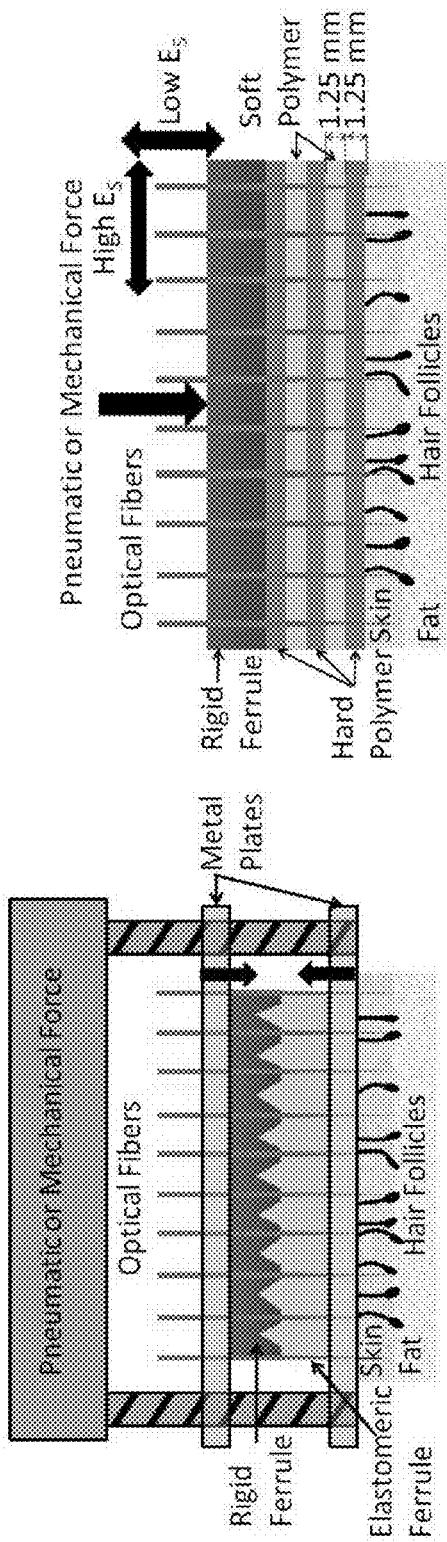
FIG. 12 provides schematic diagrams showing embodiments of the invention that comprise an array of microneedles supported along their length by rigid and soft ferrules during insertion of the needles into skin.

Once the microneedle system is fabricated, the clinician places the elastomeric guidance ferrule in contact with the patient's skin. Mechanical compression induced by the clinician or an automatic control system (e.g., vacuum pump with adjustable pressure/force) will cause the elastomeric ferrule to compress or collapse and pull the rigid ferrule (and fibers) toward the skin. As shown in FIGS. 10 and 12, the distal (usually tapered, but not required) ends of the fibers will penetrate into the skin guided by the elastomeric ferrule.

To maximize the smoothness of the operation and treatment efficacy, a feedback and control mechanism with stress/strain sensors can be applied to monitor penetration depth and force. When the pressure/vacuum/displacement sensor detects a critical threshold value, the laser source can be turned on and energy provided to the fibers and delivered into the skin for a given amount of time to provide an appropriate radiative dose.

In embodiments of systems of the invention, one or more microneedles are fixed to a rigid ferrule (straight bushing) and extend unfixed throughout the full-thickness of an adjacent elastomeric ferrule. As the elastomeric ferrule is compressed between the rigid ferrule and a tissue surface, such as skin, microneedle tips exit the elastomeric ferrule and penetrate into adjacent tissue. The elastomeric ferrule provides lateral support for the microneedles, increasing the critical buckling force, similar to mosquito bite mechanics.

The rigid ferrule may be forced toward the tissue surface directly using human-applied force or with an alternative mechanism such as vacuum force. If the elastomeric ferrule is fabricated with a porous, open-celled elastomer such as foam, vacuum pressure can be used to collapse the pores, inducing needle insertion into skin. Additionally, vacuum pressure may help seal the skin surface against the elastomer, minimizing shear stress at this interface.

The force exerted on skin by the microneedles is negligible; however, the force needed to compress the elastomeric ferrule against tissue must be below skin pain and damage thresholds. FMD designs capable of preventing excess force on the subject include the two designs shown in FIG. 12. The schematic diagram at the left of FIG. 12 provides the elastomeric ferrule between two rigid metal plates, which is compressed during use of the device. In embodiments, the force needed to deform the elastomeric ferrule is not be applied on the skin but rather on the metal plates using a pneumatic or screw-driven linear actuator attached to opposite sides of the square plates. Alternatively, embodiments can comprise as the material for the elastomeric ferrule one with directionally dependent elastic moduli, preferably a high elastic modulus in the lateral direction E>100 MPa, but a much smaller elastic modulus E<1 MPa in the vertical direction. Such a material can be achieved by composite (layered) manufacturing as shown in the schematic diagram shown on right in FIG. 12.

In a specific embodiment of FMD, which is especially useful for hair removal applications, the needles cover approximately a 1 cm$^2$ surface area, the needles are configured to be capable of attaining a 2 mm needle insertion depth, and comprise about 30 needles/cm$^2$ based on hair follicle length and density. The device optionally comprises a rigid ferrule, which can be made of machined aluminum (5 mm thick) and an elastomeric ferrule which can be comprised of rubber or foam (1-20 mm thick). Precision drilled holes are made through both materials to hold the optical fibers. Fibers are manually inserted into holes, positioned with our stereo microscope, and fixed to the rigid ferrule with epoxy. A pneumatic chamber can be used to cause FMD compression against the skin surface.

For dermatological applications, the devices may be placed against a patient's skin. Mechanical compression causes the fiber needles to slide through the ferrule and painlessly penetrate the skin, similar to the dynamics of a mosquito bite. The fiber tips may be positioned at desirable target positions (potentially >2 mm deep) within tissue. Subsequent application of laser energy into the proximal end of fibers will be transmitted efficiently to the target tissue surrounding the fiber tips, thereby inducing desirable photothermal, photomechanical, or photochemical damage to the intended target.

In preferred embodiments, the clinician places the ferrule in contact with the patient's skin and the distal end of the fibers slide through the ferrule, elastomeric material, and into the skin. A feedback and control mechanism monitors treatment for penetration depth and force using a complementary series of stress/strain sensors. Diffuse optical tomography (DOT) may then be used to optically identify and characterize tissue structures beneath the epidermis layer, such as cancerous cells, hair follicles, freckles, tattoo particles, blood vessels, epidermal/dermal junctions, and dermal/adipose junctions.

$F_{CR}$ of microneedles can be increased substantially by embedding them inside an elastomeric medium during insertion. As is explained in more detail below, an increased buckling strength obtained from the elastomeric support allowed extremely slender microneedles of 55 μm diameter and 3 mm length to penetrate ex vivo porcine skin.

The critical buckling force of silica microneedles with 55, 70, and 110 μm diameters and 3 mm lengths were measured with and without a surrounding elastomeric support (PDMS, polydimethylsiloxane). Use of the PDMS support increased critical buckling force by an average of 610%, 290%, and 33%, respectively. Thus, it has been shown that the critical buckling force of microneedles can be increased substantially to allow extremely high aspect ratio microneedles, 55-110 μm in diameter and 3 mm in length, to penetrate ex vivo porcine skin. By this strengthening method, the safety and reliability of microneedles in potential clinical applications can be considerably enhanced.

By providing microneedles with an elastomeric (an elastic polymer) lateral support, an increase in mechanical strength and a reduction of the threshold microneedle diameter necessary to penetrate skin can be attained. To this end, a method of embedding silica microneedles in polydimethylsiloxane (PDMS, Sylgard® 184, Dow Corning, Midland, Mich.) is provided by the invention. The elastomeric material used in preferred embodiments comprises a Shore A hardness (ASTM D2240) ranging from about 30-70, such as 40-60, or even 50; a tensile strength (ASTM D412) ranging from about 5-10 MPa, such as about 6-8 MPa, such as about 7.1 MPa; an elongation at break (ASTM D412) of about 100-200%, such as about 110-190%, such as about 120-180%, such as about 130-170%, such as about 140-160%, such as about 150%; and a tear strength—die B—(ASTM D624) of about 1.5-3.5 kN/m, such as about 2-2.5 kN/m, such as about 2.6 kN/m.

More particularly, fiberoptic microneedles were manufactured from multimode silica optical fibers with core/cladding diameters of: 50/55, 50/70, and 100/110 μm (FVP050055065, FIP050070085, and FIP100110125 Polymicro, Phoenix, Ariz.). To manufacture the microneedles used in the buckling experiments, one end of an optical fiber was flat-polished. The polished fiber was adhesively bonded inside a metal tube (127 μm inner diameter, 236 μm outer diameter) with 3+/−0.1 mm length extending beyond the tube ending with the flat-polished surface. Microneedles used in the skin penetration experiments were manufactured using the same method, but the fibers were angle-polished at a 25 to 30° angle using an Ultrapol fiber lensing machine (Ultratec, Santa Ana, Calif.) instead of being flat-polished.

A BOSE™ Electroforce™ 3100 mechanical testing stage was utilized to record the axial force and displacement during failure testing of fiberoptic microneedles. This instrument has a 1.5 μm displacement resolution over its 5 mm range. The accuracy of the force cell was +/−55 mN for measurements conducted with 110 μm diameter microneedles. A different force cell with a higher accuracy of +/−6 mN was used for measurements with 55 and 70 μm diameter microneedles. Microneedles of each diameter were tested with both: unsupported and supported conditions (3 mm length). Each experiment was repeated for N=5. For supported experiments, the microneedles were embedded inside a 2.5 mm deep layer of PDMS. Any similar type of material can be used, which has one or more of the same or similar properties as PDMS. Also it is not critical the depth of elastomeric material used, so long as a sufficient portion of the microneedle is supported along its length by the elastomeric material.

Figure 56:
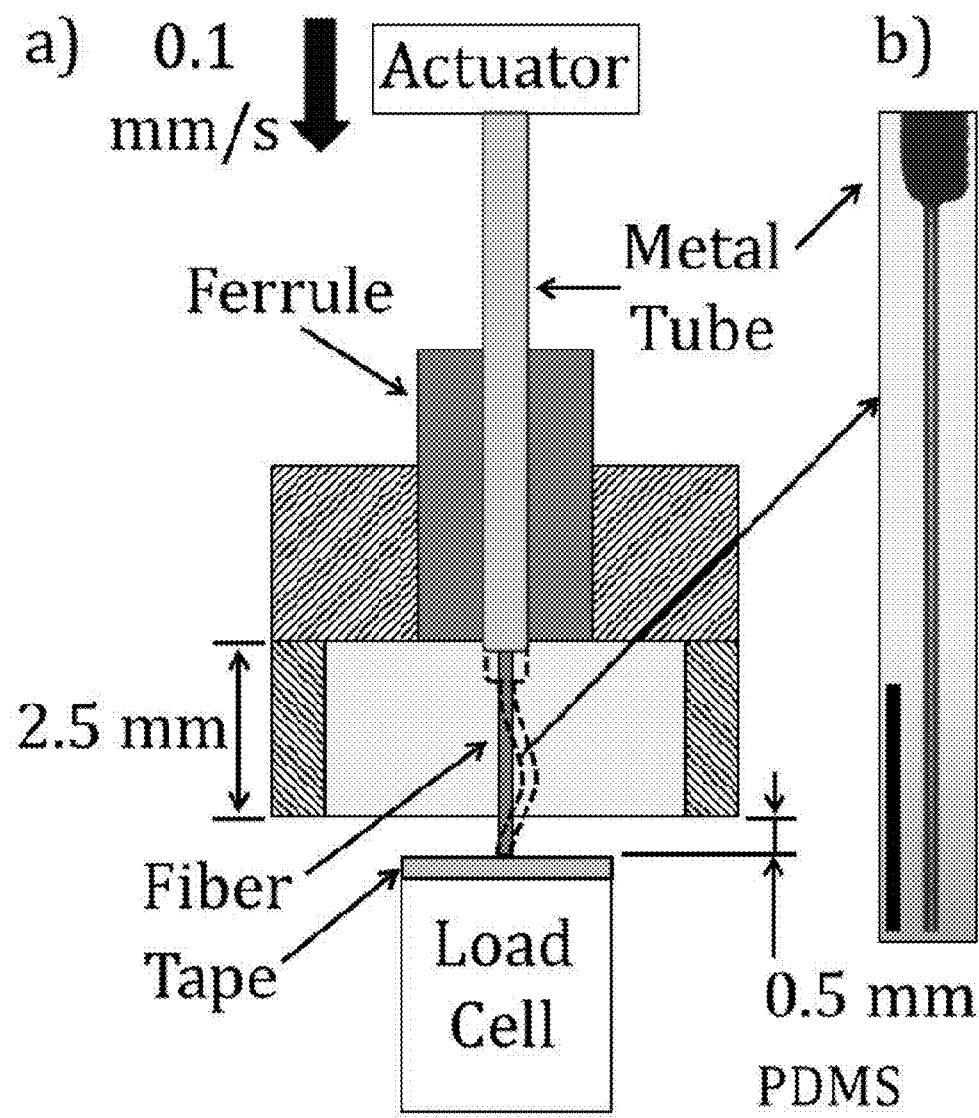
FIG. 56A-B is a schematic drawing of a representative microneedle device according to the invention using a PDMS supporting ferrule.

To manufacture embedded microneedles, liquid PDMS composed of a monomer and a hardener with 10:1 weight ratio was poured into a 10 mm diameter mold around the microneedles. PDMS was hardened at 150° C. for 15 minutes. The experimental setup for buckling experiments with support is shown in FIG. 56A. For experiments without support, the setup was identical but without PDMS. A bright field microscopy image of a representative microneedle used in buckling experiments is shown in FIG. 56B (Leica DM IL LED, Leica Microsystems, Buffalo Grove, Ill.). The metal tube was guided by a zirconia ferrule with 250 µm inner diameter. For the supported experiments, the metal tube was pushed through the PDMS by the linear actuator of the testing stage with a velocity of 0.1 mm/s. Thus, the microneedles, adhesively bonded to the tube, were pressed against the hard surface of the load cell. Double-sided tape was placed on the load cell surface to prevent the microneedles from sliding. As the actuator moved the tube, the microneedles shortened, deflected laterally (demonstrated by the dashed lines), and finally buckled. Force and displacement data was recorded throughout microneedle contact with the load cell, during bending, and following buckling failure of the microneedle.

Figure 57:
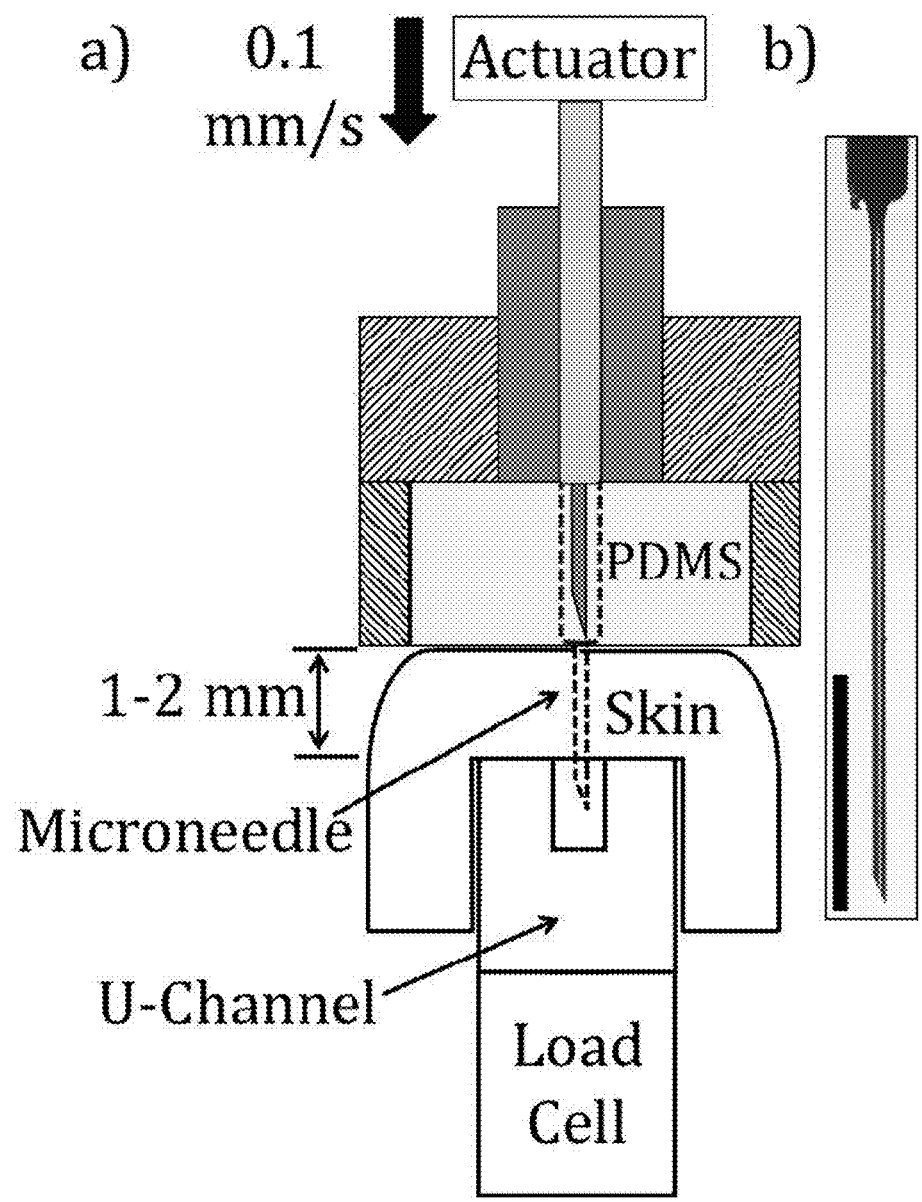
FIG. 57A-B is a schematic drawing of a representative microneedle device according to the invention with the microneedle embedded in PDMS for support.
Figure 58:
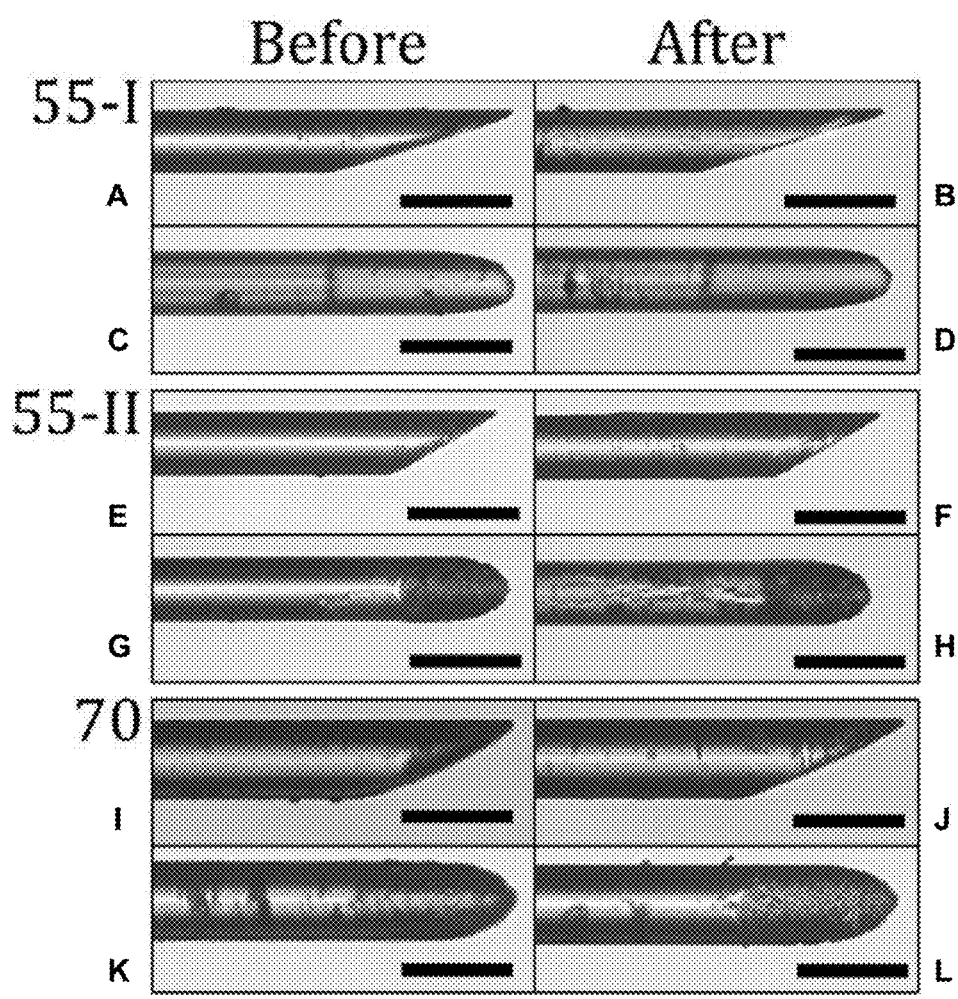
FIGS. 58A-L are photographs of microneedles of varying aspect ratios which were used to penetrate skin, the images showing no damage to the tips after use.

Penetrating Ex Vivo Porcine Skin with Microneedles. Ex vivo abdominal pig skin was acquired from a local abattoir. Specimens were cut to 1-2 mm thickness, including both the epidermal and dermal layers. In order to maintain hydration until the experiments were conducted, dissected skin was placed inside a plastic bag between paper cloths saturated with isotonic saline and maintained at 4° C. The high accuracy load cell was used for force (load) measurements with 55 and 70 µm diameter microneedles with and without the elastic support. Skin penetration experiments with microneedles having diameters equal or larger than 73 µm have been previously demonstrated to penetrate skin. Kosoglu M A, Hood R L, Chen Y, Xu Y, Rylander M N, Rylander C G, "Fiber Optic Microneedles for Transdermal Light Delivery: Ex Vivo Porcine Skin Penetration Experiments," J. Biomech. Engr. 2010; 132(9):091014. A schematic representation of the skin penetration experiments is given in FIG. 57A. A bright field microscopy image of a representative microneedle used in the skin penetration experiments is shown in FIG. 57B.

Prior to experiments, the microneedles were positioned less than 1 mm away from the surface of the ex vivo porcine skin stretched over a U-channel. During the experiments, microneedles were displaced toward the skin's surface with a velocity of 0.1 mm/s. The penetration experiment was finalized when the microneedle either buckled or penetrated through the skin. Buckling was observed by the instantaneous drop in the force on the microneedle and an audible report. Successful penetration was observed by seeing the tip of the microneedle penetrate through the entire 1-2 mm thickness of the skin. Following the sequence of penetration experiments, each microneedle was removed from the skin, and examined for damage using both a surgical microscope (Seiler Revelation, St. Louis, Mo.) and the bright field microscope.

Elastically supported 55 and 70 µm diameter microneedles were able to penetrate the ex vivo porcine skin. A 70 µm diameter microneedle penetrated the skin 5 times without buckling. Three 55 µm diameter microneedles were tested. The first two 55 µm diameter microneedles penetrated twice each, and before buckling during the third attempt. The experiment was finalized after obtaining another successful penetration with the third microneedle (total of 5 successful penetrations out of 7 attempts with three 55 µm diameter microneedles). Bright field microscopy images of two 55 µm diameter microneedles and a 70 µm diameter microneedle that successfully penetrated skin indicated no damage.

Accordingly, microneedle $F_{CR}$ may be increased if microneedles are embedded in an elastomeric support medium. In addition to their application specific design requirements, microneedles should possess the required critical buckling force to be inserted into tissue. Slender microneedles can be made stronger by being embedded within an elastomer in a configuration that allows the forward movement of the microneedles during insertion. Buckling experiments with unsupported and supported microneedles were conducted to show the effect of mechanical strengthening on $F_{CR}$. The amount of strengthening that was achieved increased significantly as the microneedle diameter decreased. There was uncertainty in the supported length 2.25 mm+/−0.25 mm due to the manual pouring of the liquid PDMS. The $F_{CR}$ of supported microneedles varied over a wider range than the unsupported microneedles. This variation in $F_{CR}$ might have also been caused by the uncertainty in the supported length mentioned earlier.

Lowering the diameter threshold for penetrating skin with fiberoptic microneedles is challenging, as $F_{CR}$ is directly proportional to the fourth order of the microneedle diameter. For example, $F_{CR}$ of a 73 µm diameter microneedle is 210% and 18% greater than 55 and 70 µm diameter microneedles respectively. Thinner microneedles could penetrate into the skin, because mechanical strengthening by the PDMS compensated for the loss in mechanical strength. Average $F_{INS}$ observed during insertion of 55 and 70 µm diameter microneedles was 128 and 179 mN, respectively. Microneedles that were not supported with PDMS did not possess the required buckling strength to penetrate skin, as the $F_{CR}$ of unsupported 55 and 70 µm diameter microneedles was 66 and 143 mN, respectively. This lack of buckling strength resulted in the mechanical failure of all unsupported microneedles that were tested for penetrating skin.

Thinner microneedles are not only preferable for decreasing invasiveness, but also possess superior light delivery properties. Fiberoptic microneedles of 33 to 72 µm diameter (3 mm length) produced a more uniform intensity and temperature distribution compared to microneedles with 97 to 99 µm diameter and standard multimode optical fiber with 125 µm diameter. See Kosoglu M A, Hood R L, Rossmeisl J H, Grant D C, Xu Y, Robertson J L, Rylander M N, Rylander C G, Fiberoptic Microneedles: Novel Optical Diffusers for Interstitial Delivery of Therapeutic Light, Laser Surg Med 2011; 43(9):914-920. Through mechanical strengthening, as outlined in this study, these thinner, diffusing microneedles may become practical to penetrate skin and deliver light directly into sub-dermal regions.

Microneedles with sharper tips ($d_{TIP}$=2-6 µm) enhance the penetration characteristics of the fiberoptic microneedles, however, these ultra-sharp tips can be more susceptible to tip damage, which can cause medical complications. In contrast, mechanical strengthening with an elastomeric ferrule can allow the use of blunt, angle-polished microneedles to penetrate skin.

The mechanical strengthening methods outlined in this specification can be used for other types of microneedles, such as hollow microneedles for drug delivery. Microneedles with thinner walls can be used to lower viscous losses and increase drug delivery flow rate without increasing outer diameters and therefore invasiveness. See Hood R L, Kosoglu M A, Parker M, Rylander C G, Effects of Microneedle Design Parameters on Hydraulic Resistance, J. Med Devices 2011; 5(3). Microneedles with smaller diameters can reduce blood vessel trauma and pain due to the stimulation of peripheral nerves. With the effect of mechanical strengthening, longer microneedles can be used to possibly reach deeper tissue regions in the skin or in other soft tissues. Mechanical strengthening can increase the safety and reliability of microneedles, thus enabling future clinical applications.

Indeed, embodiments of the invention can be coupled with any optical imaging system for diagnostic or therapeutic use. Sub-dermal targets can be identified using any optical molecular imaging technique, such as OMT, OCT (Optical Coherence Tomography), bioluminescence imaging, Diffuse Optical Tomography (DOT), and fluorescence tomography to name a few.

Additionally, light can be introduced to certain fibers and detected by others, with the process implemented sequentially and/or in parallel as a function of wavelength. Moreover, laser therapeutics is thus further enabled with the proposed device in that laser irradiation can be directed into the proximal end of selected individual fibers to induce photothermal, photomechanical, or photochemical damage to target tissue structures identified using DOT. In concert with DOT, treatment can thus be more specified to the target area, therefore dramatically reducing collateral damage and enabling reduced pain during treatment and faster wound healing. See, Kaushik, S., et al., "Lack of pain associated with microfabricated microneedles," Anesthesia and Analgesia, 2001, 92(2): p. 502-504, the disclosure of which is incorporated by reference herein in its entirety. Embodiments of the invention have potential market implications in cosmetic surgeries, oncology treatments, dermatology treatments, and alternative medicine protocols.

The microneedles, with or without a skin insertion tool, and the microneedle systems of embodiments of the invention can be used for numerous clinical applications.

Figure 13:
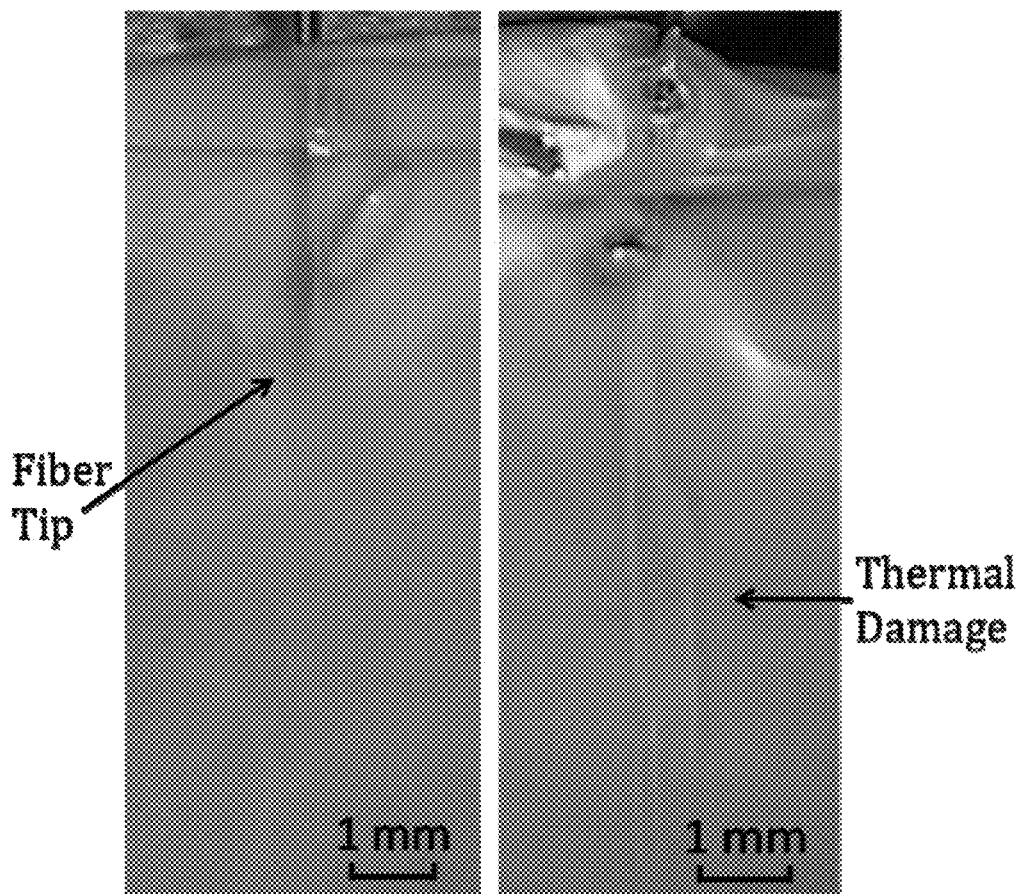
FIG. 13 are photographic images showing photothermal-induced denaturation in gelatin tissue phantoms using a microneedle light delivery system according to the invention.

FIG. 13 shows photothermal-induced denaturation in gelatin tissue phantoms using a microneedle light delivery system. The microneedle was inserted into the gelatin and a 1064 nm wavelength laser (~0.1 W continuous wave) was focused into the core of the proximal end of the fiber. Due to absorption of photons by the water in the phantom along the direction of the light propagation, heat was generated which melted and denatured the gelatin to a depth of approximately 5 mm.

More specifically, the microneedles were used to ablate the tissue phantom (gelatin) with a focused high power laser. The microneedles were inserted into gelatin and a 5 W fiber laser with a wavelength of 1064 nm was focused into the core of the optical fiber at its other end, which was straight cleaved. The needle at the tip increased the light intensity per area and the intense laser light tunneled through the gelatin. The microneedle is located at the left side of the images in FIG. 13. It is embedded inside a cube of gelatin that is placed between two glass cover slides in order to minimize spurious reflection. The top image shows the start of the experiment. When the laser is activated, heat emanating from the tip of the needle melts the gelatin along the direction of the needle axis. The resulting shape of gelatin is shown in the bottom image. The red light inside the optical fiber is a guide laser, which makes it possible to see the location of the infrared beam.

Laser therapeutics can be used to direct laser irradiation into the proximal end of selected individual fibers to induce photothermal, photomechanical, or photochemical damage to targeted tissue structures identified using DOT. Light can be delivered to deeper targets because of the insertion of the fibers into skin. Specificity of the treatment can be enhanced using DOT imaging and less collateral damage potentially means less pain during treatment and faster wound healing process. Further, DOT may provide feedback on success of the treatment.

In photothermal therapeutics, successful treatment outcome often depends on a desired temperature increase in selected tissue regions resulting in destruction of targeted chromophores or regions, while maintaining temperature below the damage threshold in non-targeted tissue regions, a process called selective photothermolysis. See, Anderson, R. R. and J. A. Parrish, "Selective Photothermolysis—Precise Microsurgery by Selective Absorption of Pulsed Radiation," Science, 1983, 220(4596): p. 524-527, the disclosure of which is incorporated by reference herein in its entirety.

Laser-based hair removal, for example, benefits from selective heating of melanin in hair follicles, while minimizing heating in surrounding skin. Selective thermal damage of pigmented target structures occurs when sufficient fluence is delivered during a time equal to or less than the thermal relaxation time $\tau_r$ of the target, where $\sigma_r$ is defined as the time required for the central temperature of the target to decrease by 50%. For long pulses (duration $\gg \tau_r$) non-specific damage will result due to significant heat transfer during the pulse.

Rate of temperature increase dT(r,z)/dt in tissue at position (r,z) due to light absorption is given by, $$\frac{dT(r,z)}{dt} = \frac{\mu_a \Phi}{\rho c} \quad (1)$$

and is dependent on local tissue absorption coefficient ($\mu_a$), local optical fluence ($\Phi$), tissue density ($\rho$), and specific heat capacity (c).

Local fluence in tissue may be approximated by:

$$\Phi(z) = \Phi_0 e^{-\mu_{eff} z} \quad (2)$$

where $\Phi_0$ is the irradiance on the surface, z is tissue depth, and $\mu_{eff}$ is effective attenuation coefficient which depends on tissue optical properties. The optical penetration depth, defined as $1/\mu_{eff}$, is the tissue depth at which fluence has exponentially decayed to 37% of the incident surface irradiance, and is approximately 750 µm in skin at a wavelength of 700 nm. See, Anderson, R. R. and J. A. Parrish, "The Optics of Human-Skin," Journal of Investigative Dermatology, 1981, 77(1): p. 13-19, the disclosure of which is incorporated by reference herein in its entirety.

Figure 14:
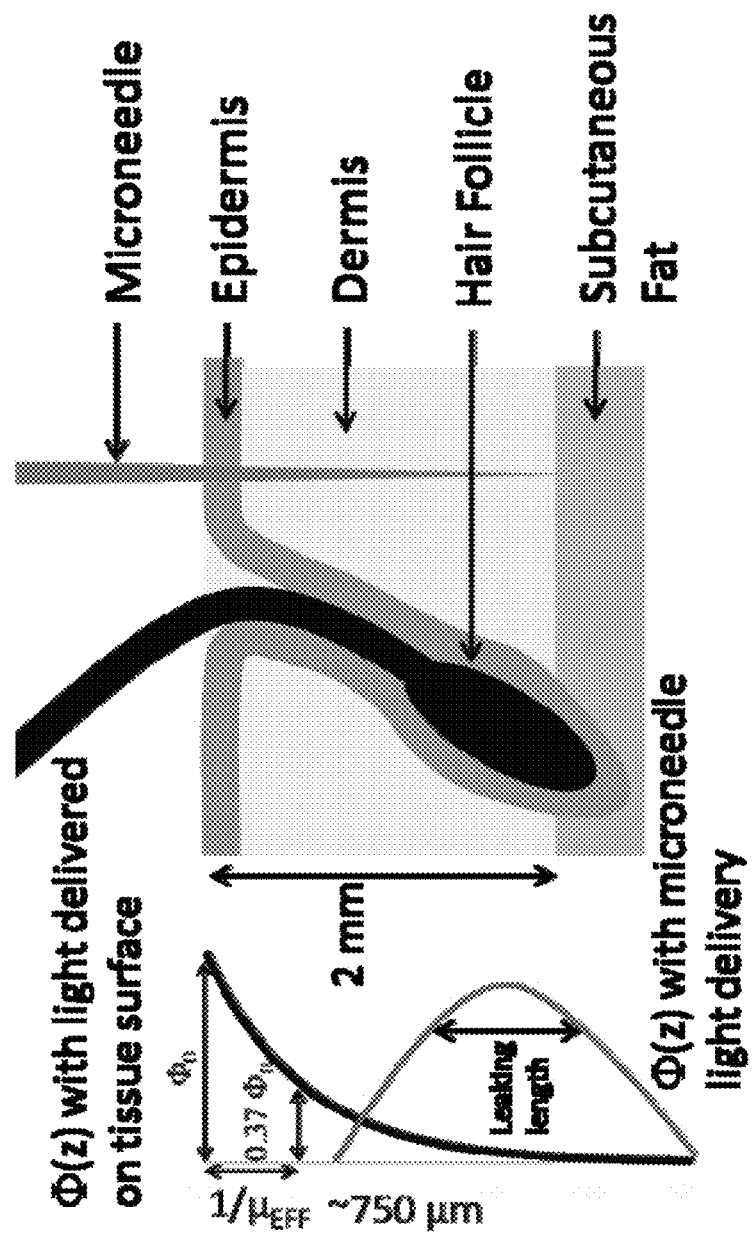
FIG. 14 is a graphical illustration of $\Phi(z)$ and optical penetration depth in skin using current commercial laser treatment procedures (beam directly delivered to skin surface).

FIG. 14 (left) provides a graphical illustration of $\Phi(z)$ and optical penetration depth in skin using current commercial laser treatment procedures (beam directly delivered to skin surface). As shown in the graph, very little light reaches the deep portions of the hair follicle where light is needed most.

One example of the application of the invention is for laser-based hair removal. Laser-based hair removal has recently received attention because of its noninvasive nature, fast results, and potential for permanence. Long term results have been described with Alexandrite lasers (755 nm) which use melanin in the hair follicle as a chromophore for selective photothermolysis. See, Nanni, C. A. and T. S. Alster, "Long-pulsed alexandrite laser-assisted hair removal at 5, 10, and 20 millisecond pulse durations," Lasers in Surgery and Medicine, 1999, 24(5): p. 332-337, the disclosure of which is incorporated by reference herein in its entirety.

Skin anatomy and tissue optics are such that it is difficult to achieve the light levels needed for selective photothermolysis of the deep portions of hair follicles which can be greater than 2 mm under the skin surface. The epidermis contains additional melanin through which light must pass to reach the follicle. Ideally follicles should be damaged without much epidermal injury. Approximating hair follicles as a cylinder, their thermal relaxation times are in the range of about 10-100 msec for diameters between about 100-300 µm. See, Campos, V. B., et al., "Ruby laser hair removal: Evaluation of long-term efficacy and side effects. Lasers in Surgery and Medicine," 2000, 26(2): p. 177-185, the disclosure of which is incorporated by reference herein in its entirety.

However the thermal relaxation for the epidermal melanin layer (~50 um thickness) is approximately 3-10 msec. See, Grossman, M. C., et al., "Damage to hair follicles by normal-mode ruby laser pulses," Journal of the American Academy of Dermatology, 1996, 35(6): p. 889-894, the disclosure of which is incorporated by reference herein in its entirety. Consequently, laser pulse duration for hair removal treatments is limited in order to prevent undesirable excessive heating and damage in the epidermal layer. Techniques which provide skin surface cooling during laser treatment are able to partially mitigate the undesirable epidermal heating.

In practice, the ideal patient for laser hair removal has dark hair and fair, untanned skin. Such patients are usually best treated with high fluences (>39 J/cm$^2$) and almost always achieve reduction of hair to a sparse amount in 3-6 treatments, with minimal or no side effects. Darker skin types with dark hair have a higher incidence of side effects such as epidermal damage. To limit epidermal damage in dark skin types, treatment fluence below 40 J/cm$^2$ is often used, which also reduces efficacy and requires a higher number of treatments.

The following example is a demonstration of the invention using porcine skin to validate the effects of the device on hair removal.

Design of Individual Microneedle Fiber Tapers.

Light guiding microneedles are manufactured from large-core multimode silica fibers. These optical fibers are drawn into a tapered (needle-like) shape. The geometry in this example (~2 mm length, 40 µm average diameter, submicron tip) is based on the ~2 mm depth of human and porcine hair follicles as well as the painless microneedle design demonstrated by the mosquito. See, Meyer, W., R. Schwarz, and K. Neurand, "The skin of domestic mammals as a model for the human skin, with special reference to the domestic pig," Curr Probl Dermatol, 1978, 7: p. 39-52, the disclosure of which is incorporated by reference herein in its entirety.

Free-Space Laser Beam is Coupled into Fiber Bundle.

To effectively couple light from a free-space source, such as a laser, into the fiber microneedles, multimode fibers (MMF) with a large core diameter and high numerical aperture can be used. MMF with a core diameter of 125 µm, a cladding diameter of 140 µm, and a large numerical aperture of 0.37 are commercially available. Such fibers can be packed together tightly into a simple fiber bundle, and the end of the fiber bundle is polished flat. A simple 2-element relay lens system takes the free-space collimated beam from the laser source and focuses it into the fiber bundle with more than 50% efficiency. The maximum fluence transmitted within each needle is about ~100 kJ/cm$^2$, and is well within safe limits for standard silica optical fibers. See, Yamaguchi, S., et al., "Efficient Nd:YAG laser end pumped by a high-power multistripe laser-diode bar with multiprism array coupling.," Applied Optics, 1996, 35(9): p. 1430-1435, the disclosure of which is incorporated by reference herein in its entirety.

Light Delivery Performance in Tissue Phantoms.

Tissue-representative gelatin phantoms with dimensions ~2×10×10 mm$^3$ can be used to optimize light delivery. The scattering coefficient of the phantoms can be adjusted to mimic that of human tissues by adding IntraLipid solution (similar to dairy milk) to the gelatin solution before curing. Individual fiber microneedles are inserted into the thin side of the phantom to couple red (650 nm) light from a CW diode laser source into the fibers and capture the light scattering pattern within the phantom using a stereo microscope and CCD camera. A microneedle is optimized by quantifying the leakage length and the spatial distribution of optical fluence in turbid phantoms directly from the recorded 2D images and using these data to guide the redesign process.

Measuring the Light Delivery Performance of FMD in Tissue Phantoms and Ex Vivo Porcine Skin Using Thermal Imaging During Laser Irradiation.

The performance of the FMD using quantitative thermal imaging during light delivery can be measured with 5 W 1064 nm continuous wave laser source. Temperature images of 2×3 cm$^2$ ex vivo porcine skin specimens are measured with 100 µm spatial resolution and 16 ms temporal resolution (FLIR Thermovision A40M). The FMD can be applied to the epidermal surface of the specimens, light delivery proceeds for 2-10 s, and the thermal camera records the temperature elevation of the subdermal surface. By varying the tissue specimen thickness and microneedle insertion depth, the skin temperature profile can be mathematically reconstructed in three dimensional space and time to verify performance of the FMD.

FMD vs. Conventional Laser Hair Removal Treatment Using Histological Analysis and Hair Counting of In Vivo Porcine Model.

Typically, a total of nine farm pigs with pigmented skin, approximately 25 kg in weight, are used. Three animals are assigned to each group, with group one evaluated one week after treatment, group two evaluated one month after treatment, and group three evaluated three months after treatment. Animals are anesthetized using 2% isofluorane gas for tattooing and laser application. On each lateral side of the dorsum, 2 cm lateral to the spine, areas 1 cm in diameter are marked to denote location for hair removal analysis. Each side of the dorsum is used experimentally to obtain duplicate measurements for each animal. High resolution photographs of the areas are taken for counting the number of hairs initially. Animals are tattooed to permanently mark treatment sites, and the skin heals for two weeks prior to light treatment application. Nine areas for evaluation of hair removal along the dorsum, parallel to the spine, allow for 2 cm spaces between each treated area.

FMD results can be compared with a conventional laser procedure which uses surface cooling to protect the epidermis. The experimental parameters to evaluate are radiative dose, and pulse duration. A Candela Gentle YAG laser can be used at 1064 nm, 8-40 J/cm$^2$. Three pulse times for light application can be used: 3, 10, and 20 ms. Light is applied once for each experimental configuration. The skin is evaluated at three ending time points for number of hairs per area, and appearance of epidermal damage. At the ending time points, animals are euthanized by injection of a lethal dose of pentobarbital. Photographs of each treatment area are taken, and the treatment areas are excised and prepared for histological evaluation. Skin is sectioned, stained, and observed by light microscopy for the number of hairs in an area, any necrotic areas of tissue, or any other abnormal dermal features. Areas treated with conventional light application can be compared to areas treated with the FMD statistically by number of hairs per area.

Typically, hair removal effectiveness is substantially improved using the FMD-assisted laser procedure as compared to the conventional procedure without the FMD. The margin of improvement with FMD is greatest for higher radiative doses and longer pulse durations, where treatment effectiveness is known to be poor in pigmented tissue.

Because the devices according to embodiments of the invention can be manufactured for low cost (typically under $10), and because the needles penetrate skin, it is preferred that the device be discarded after a single-patient treatment. By improving treatment efficacy, reduction in number of treatment sessions can be achieved, saving time for patients and clinicians, and lowering the total price of healthcare. By providing a source of treatment-derived revenue (disposable FMD) the laser manufactures can also benefit.

Figure 15:
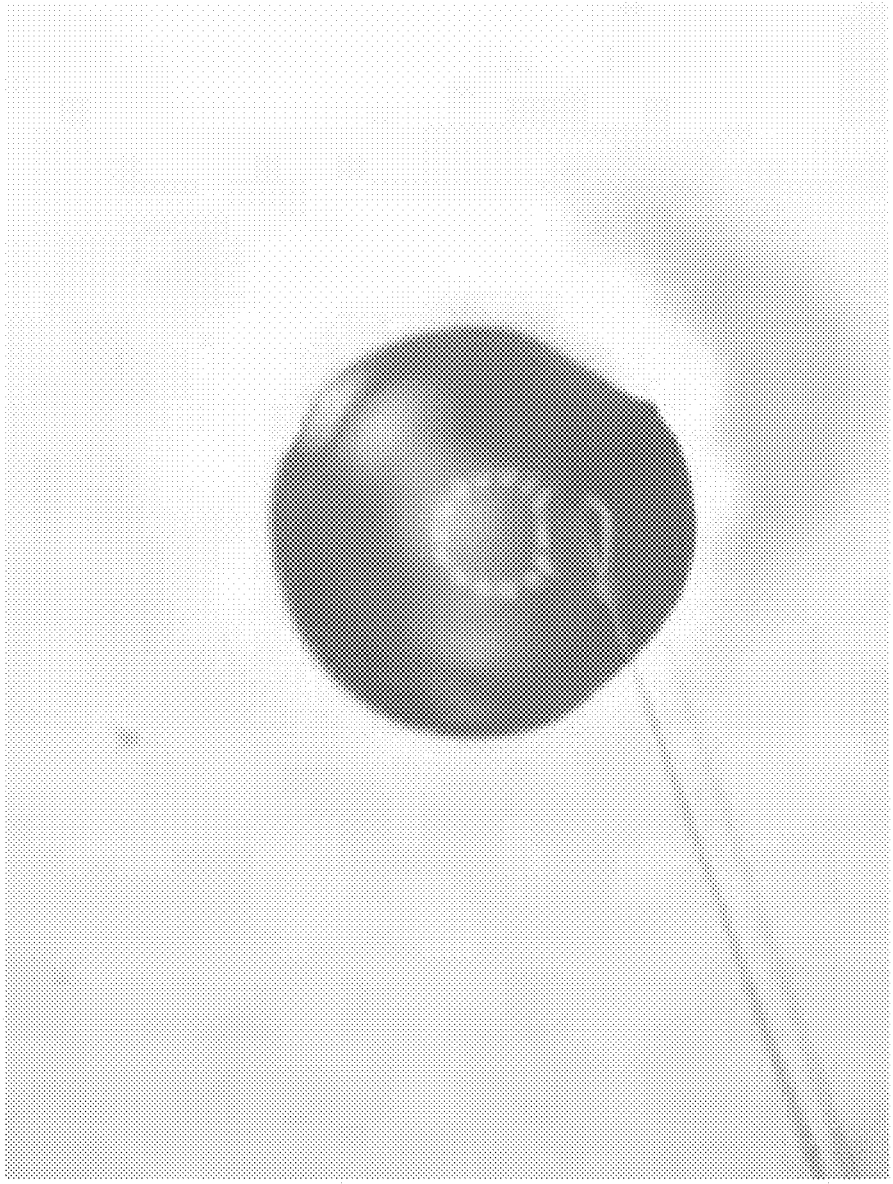
FIG. 15 is a photographic image demonstrating delivery of fluid by way of a microneedle according to the invention.

Needles of the present invention can be used for applications not requiring transmission of light and thus need not be prepared from fiberoptic material. For example, whether or not the microneedles are constructed of a material capable of transmitting light (such as silica), the microneedles can be used to deliver fluids and/or particulate matter into tissue. FIG. 15 demonstrates that embodiments of the invention can include hollow microneedles capable of permitting delivery of small volumes of fluid and particulates into tissue. Needles capable of delivering combinations of light, fluids, and/or particles are also feasible and within embodiments of the present invention. More particularly, FIG. 15 shows water delivery through a hollow silica fiber microneedle. The Fiber tip (about 20 micron outer diameter and about 10 micron inner (hole) diameter) was prepared by tapering a hollow-core silica fiber (125 micron outer diameter, 104 micron inner diameter) using a propane torch technique. Pressurized $CO_2$ (840 psi) forced water through the needle.

Figure 16:
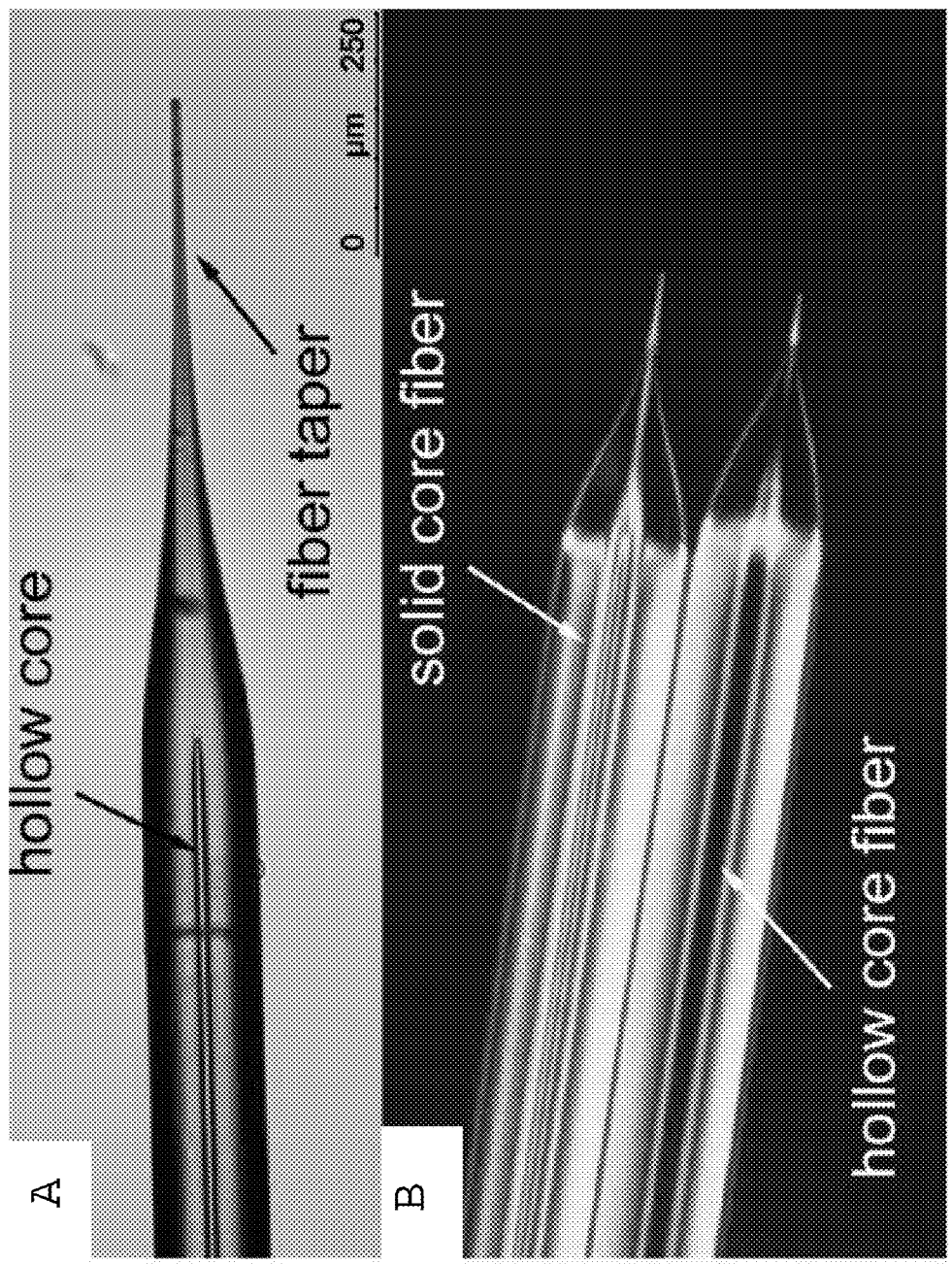
FIGS. 16A-B are optical microscope images of microneedles of the invention.
Figure 17:
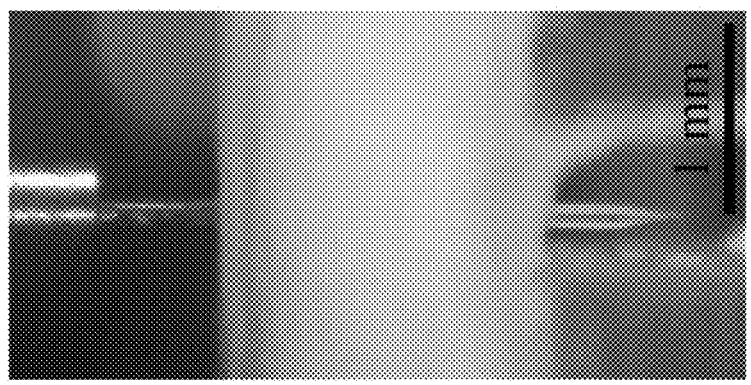
FIG. 17 is a photographic image of a microneedle penetrating skin.

Needles of embodiments of the invention can be solid core, hollow core, or even liquid core. Core and cladding materials, as well as diameters, are chosen for their ability to propagate light through the needle according to a desired application. Various needles can be combined to achieve a desired effect, for example, combining (by fusion or other means) solid core needles with hollow core needles, which are capable of transmitting light at different rates and/or wavelengths (e.g., single mode and multi-mode fibers can be combined). FIG. 16 shows optical microscope images of a hollow core fiber taper (top) and the combination of a hollow core fiber taper fused with a solid core fiber taper (bottom).

The needles, systems, and methods of embodiments of the invention can be adapted for use with any laser-based treatment or diagnostic in which light is used to detect or treat targets under or on the skin surface. Targets include, but are not limited to, blood vessels (e.g., treatment of varicose veins), skin (e.g., skin reshaping), hair follicles (e.g., unwanted hair removal), subdermal fat (e.g., liposuction and fat reshaping), tattoo particles (e.g., tattoo removal), and port wine stain removal. Indeed any treatment including oncology treatments, dermatology treatments, cosmetic surgeries and procedures, alternative medicine protocols (e.g., acupuncture), treatment of central nervous system cancers, treatment of bladder cancer, and treatment of deep skin cancers (e.g., by way of minimally invasive laser-based hyperthermia therapy of cancers under the skin, such as melanoma) can be improved by reducing patient pain and/or recovery time and skin damage.

Fiberoptic Microneedle Device for Convection-Enhanced Thermochemotherapy of Malignant Glioma.

Figure 23:
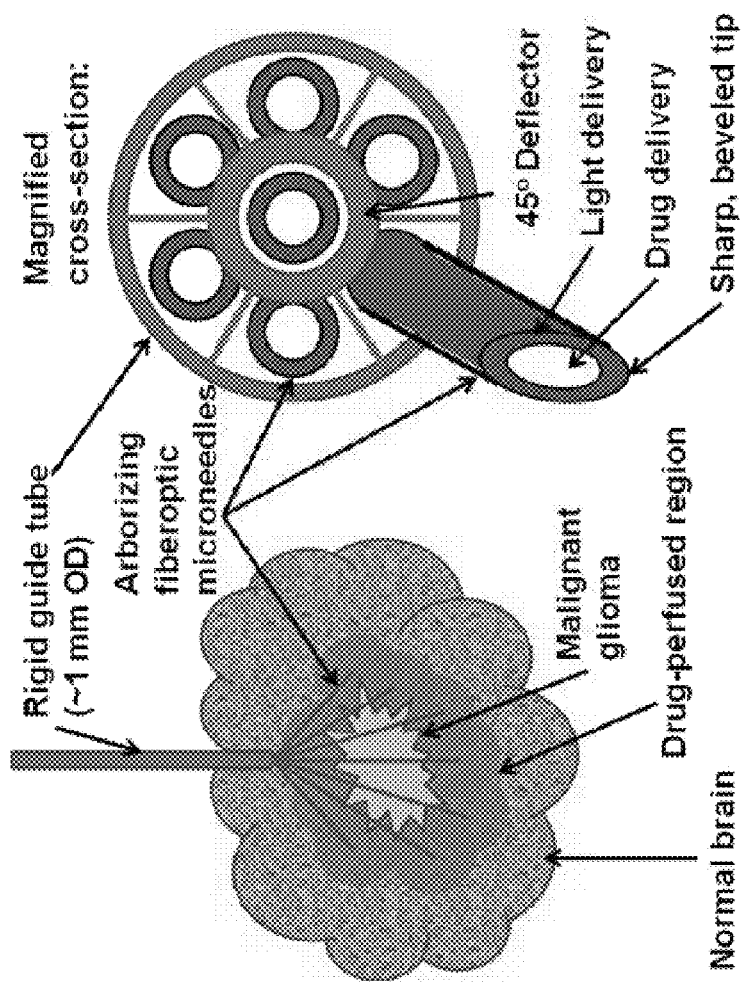
FIG. 23 is a schematic of the fiberoptic microneedle device with multifunctional arborizing, light guiding, and drug delivery fibers for treatment of MGs.

In embodiments where the microneedles of the present invention are used to treat central nervous system cancers and more specifically malignant gliomas (MGs), a device comprising a bundle of fiberoptic microneedles is disclosed. Embodiments of the invention include a device which is comprised of a bundle of fiberoptic microneedles (e.g., diameter 365 µm OD; 150 µm ID). Indeed, any microneedle structure described in this specification can be used for this particular treatment application. In preferred embodiments, the microneedles may be passed through a rigid stereotatically guided tube and then arborized (branched). Fiber tips may be precisely positioned to enhance drug delivery to desirable margins surrounding MGs (See FIG. 23). The unique arborizing, multi-fiber catheter feature of the FMD may be well-suited to deliver chemotherapeutic drugs locally to the tumor site and large surrounding margins to reach infiltrative cells. The surrounding margins may be greater than about 2 cm to reach infiltrative cells. Because such embodiments are providing direct, local delivery to the brain, it is not necessary to destabilize the blood brain barrier (BBB) and deliver high systemic doses of drugs to achieve desired concentrations of drug in the brain. Innovative microneedle fabrication techniques are also included in the scope of this invention.

Representative devices and methods of the invention include obtaining a desired number of microneedles to bundle for the administration of the branched lights. In this embodiment, seven light guiding microneedles can be manufactured from multimode hollow silica fibers (diameter 365 µm OD; 150 µm ID) commercially available from Polymicro Technologies. Any number of fibers in a bundle can be used, for example, ranging from 1-10 fibers in a bundle. The fibers can be arranged in any manner as well other than in a circular arrangement as shown in the figures. For example, the fibers can be bundled linearly in a single row of fibers, or the fibers can be bundled linearly in two or more rows of fibers with the fibers stacked immediately one above the other or offset from one another and stacked. Said another way, a fiber on the interior of the bundle can be disposed near four other fibers or six other fibers depending on the type of configuration selected. Even further, the ends of the needles can be heat treated to bend the tip of the needle to any desired position relative to the base. More specifically, the fiber can be exposed to a heat source capable of heating the fiber material to a temperature sufficient to bend the needle into the desired angle. These optical fibers can be polished at a 60° angle (or any angle sufficient to accomplish this purpose) to achieve a sharp tip conducive to mechanical penetration through brain and MG tissue similar to a hypodermic needle. Based on the infiltrative nature of MGs and Phase II CED studies which correlated longer survival times with larger drug distribution, the microneedles can be configured with a length capable to penetrate tumor and ~2 cm surrounding margins. Further, a deflection plate at the tip of the guide tube can be used to permit microneedles to arborize (branch out) at an angle of approximately 45°. Any angle can be used and is selected according to a particular application. Indeed, in embodiments, the light from each microneedle in the bundle can be guided at an angle independent of the other microneedles, if desired. A linear actuator (e.g., Thomson Electrak Pro) can be integrated into the system with the FMD to control microneedle displacement (penetration length) into the brain up to 5 cm with 100 µm resolution. This actuator for example can have a force-feedback sensor to guarantee full insertion of microneedles into the tumor tissue, while preventing breakage. A microperfusion pump (Harvard apparatus) can also be included in the system to permit total flow rate (all 7 microneedles) up to 100 μL/min.

Figure 24:
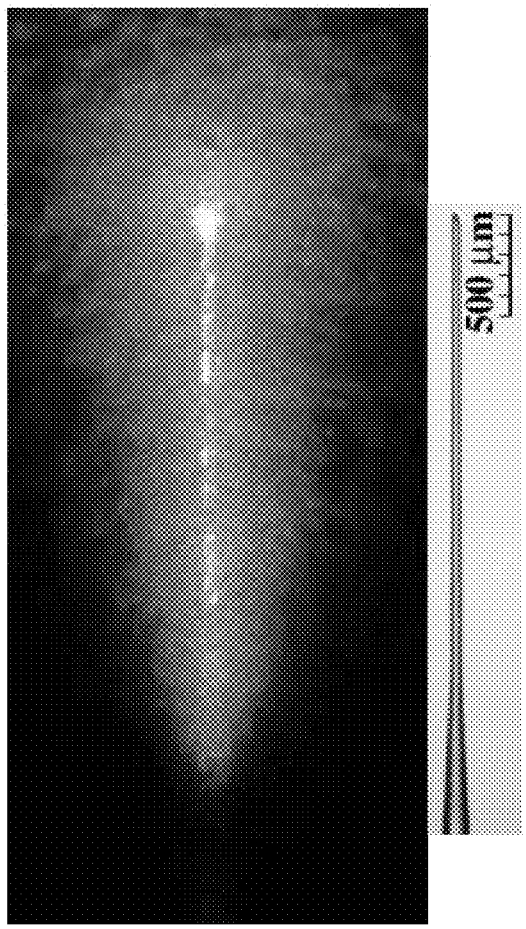
FIG. 24 is an image depicting light delivery through a customizable microneedle surface according to embodiments of the invention.

In some embodiments, the microneedle surface can be customized through acid etching to effectively distribute the photothermal dose to prevent thermal injury. Due to intrinsically higher absorption of optical energy by the gray matter and tumor tissue, the temperature increase (and permeability increase) may be desirably greater in these targets. The ability to customize light-delivery properties of microneedles is shown in FIG. 24.

Figure 25:
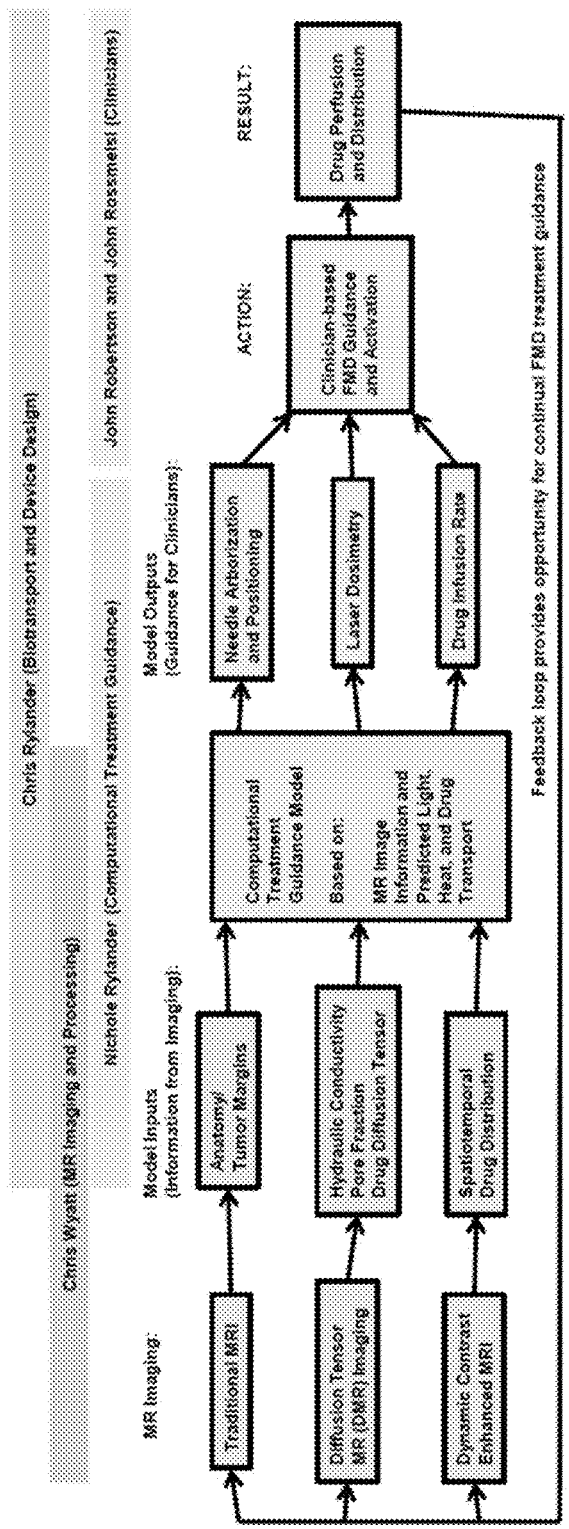
FIG. 25 is a schematic diagram showing a representative treatment planning/guidance strategy for clinicians.

Certain embodiments of the present invention provide a novel FMD guidance system comprising a novel computational model based on biotransport phenomenon (integrated light, heat, and drug transport) and MR image information as shown in FIG. 25. In such embodiments, the treatment guidance model will output recommendations for appropriate catheter positioning, laser dosimetry (i.e., irradiance and duration), and drug infusion rate. A person of ordinary skill in the art, with the benefit of this disclosure, will be able to implement the guidance system recommendations and permit FMD to achieve broad and uniform drug saturation of target tissue. In certain embodiments, such a system may improve MG therapy, leading to increased survival times and lower mortality rates. Treatment of infiltrating cells extending beyond MR-imaged tumor borders may be enabled for the first time with broad and uniform dispersion of drugs through arborizing fibers. Risk of complications may be reduced because individual fibers are ~10-fold smaller than conventional catheters causing much less mechanical trauma, bleeding, risk of stroke, and cerebral edema. Procedure time may be significantly reduced owing to: 1) multiple fibers delivering drug simultaneously and 2) micro-photothermal zones at the fiber tips which increase tissue permeability and perfusion uniformity. Clinical use may be facilitated through computer-assisted control of FMD functions: penetration of the arborizing fibers, photothermal dosing, and chemotherapeutic perfusion during MRI surveillance. In preferred embodiments, chemotherapeutic drugs that do not penetrate the BBB may be used. In some embodiments, the drug delivered may be carboplatin.

The following example is a demonstration of the invention using agarose brain phantoms, which mimic the brain's mechanical and fluid conduction properties.

Agarose brain phantoms were constructed from 0.6 wt % Agarose in aqueous solution. The FMDs were constructed by flat polishing the tip of a hollow-core fiberoptic (150 um ID, 363 um OD, Polymicro, Inc.) and a solid light-guiding fiberoptic (105/125 um core/cladding, polymicro) and embedding it into a stainless steel sheath. It is noted that any of the microneedle dimensions specified in this specification are also applicable to the microneedles used for treatment of brain cancers.

Continuous-wave 1064 nm light was coupled into the solid fiberoptic providing emission powers of 0.5-1.0 W. FD&C Blue #2 (5%) dye was infused thorough the hollow-core fiberoptic with flow rates from 0.5-2.5 uL/min to serve as a phantom drug. During FMD light and dye delivery, an approximately 10° C. increase in temperature was measured at the brain phantom surface using infrared thermography. Dye dispersal was measured by a shadowgraphy setup, assuming rotational symmetry. The dominance of convection based delivery was clearly noticeable for 2.5 uL/min flowrates. Fluid distribution was more spherical and uniform in FMD laser-irradiated samples compared to the controls (same FMD but without irradiation). FMDs used in this example demonstrated that co-delivery of light with dye increases the spatial uniformity of dye dispersal in agarose brain phantoms. Laser irradiation enables co-localized heating in the region of dye injection into the phantom. FMDs may enable a more uniform distribution of chemotherapeutic agents during CED therapy of brain cancer.

Treatment of Bladder Cancer using Selective Disposition of Photoabsorbers and Selective Delivery of Light for Targeted Treatment.

In embodiments where the microneedles of the present invention are used to treat bladder cancers and more specifically UCCs (urothelial cell carcinomas), methods of treating and a device that allows significantly enhanced laser light penetration to desired target tissue depths and selective amplification of thermal dose through introduction of exogenous photoabsorbers such as nanoparticles are disclosed herein. Representative FMDs can comprise one or more, such as two or more, optically transparent glass microneedles which may be guided into the bladder using a cystoscope and inserted into the bladder epithelium at desirable target positions, analogous to the dynamics of a mosquito bite. In certain embodiments, at least one fiber may be hollow, enabling delivery of exogenous photoabsorbers to specific tissue regions for targeted treatment. Subsequent or concurrent application of laser energy through a second solid fiber may be distributed throughout the target tissue containing the nanomaterials, thereby inducing selective photothermal or photochemical damage. Due to selective absorption of optical radiation by the nanoparticles in the target tissue, the extent and shape of thermal damage may be controlled, enabling a significant reduction in the unwanted collateral healthy tissue damage, while maximizing energy delivery to tumor tissue. In certain embodiments, a system comprising a single fiber may be used to perform the same functions.

The device and methods described in these embodiments may be well-suited to deliver photosensitizing drugs including, but not limited to, exogenous chromophores such as nanomaterials and porphyrins for selective photothermal or photochemical treatment of tumors while preserving surrounding healthy tissue. The device and methods may also introduce therapeutic agents locally to the tumor site rather than, or supplementing, systemically through intravenous injection (e.g. chemotherapeutic agents), thereby enhancing targeted tumor death and minimizing toxicity to healthy tissue.

The current method to locally deliver nanomaterials is manual syringe injection, which is difficult to position at depth and may not deliver small concentrations accurately. In contrast, devices and methods of the present invention may be sized appropriately to interface with existing clinical cystoscopes permitting optical image guidance to deliver nanoparticles to the tumor site. A person of ordinary skill in the art, with the benefit of this disclosure, would know the appropriate size to use for a specific application.

In preferred embodiments, the nanomaterials comprise light absorbing dyes. For example, the nanomaterials can comprise single walled carbon nanohorns (SWNH). SWNHs are hollow, single-walled carbon tubules, much like single-wall carbon nanotubes (SWNTs). However, the nanotubes may be short and conically-shaped, sealed graphene structures which form during synthesis into a tightly-bound aggregate nanoparticle. An outstanding benefit to the use of SWNHs for cancer therapy is that, in contrast to many other particles such as carbon nanotubes (CNTs), they are synthesized in the absence of a metal catalyst preventing associated toxicity and potential mutagenic effects of such metal ions. SWNHs possess substantially more surface area compared to other nanoparticles (e.g. gold nanoshells), making them an ideal platform for attachment of targeting moieties, imaging molecules, and treatment agent. SWNHs with specific properties can be repeatedly synthesized in a controlled manner, unlike single- and multi-walled CNTs whose properties vary widely within and between batches thereby limiting their use in clinical therapy. Surface properties, pore size, and encapsulation capacity of the SWNHs can be customized to enhance imaging, photothermal, and drug delivery through alterations in the synthesis process.

Even further, individual CNT tubules within SWNHs can be encapsulated with imaging or treatment agents. This disclosure demonstrates the ability to incorporate gadolinium and quantum dots on both the surface and interior pores of SWNHs, thereby significantly enhancing the efficiency of diagnostic imaging. The present invention discloses the ability to add targeting molecules to the SWNHs and shown selective photothermal destruction of tumor cells. Unlike PDT agents (e.g. porphyrins), SWNHs have a strong ability to absorb near infrared irradiation (700-1,000 nm) and convert electromagnetic energy into heat. This capability makes them ideal for use as photoabsorbers of NIR light for enhanced tumor destruction. SWNHs have been used with 670 nm laser irradiation to reduce the size of mouse tumors.

The present invention discloses the ability to destroy tumor cells when laser irradiation at 1064 nm was used in combination with SWNHs. Other irradiation wavelengths, or combinations of wavelengths, or protocols alternating between one or more wavelengths can be used, including for example, wavelengths from 630-2100 nm, such as 630-650 nm, or such as 640 nm; or 750-1400 nm, such as 915-980 nm, such as 915 nm, 920 nm, 924 nm, such as 924-970 nm, or 980 nm; 1210 nm; 1308 nm, 1320 nm, or 1440 nm; a combination of 1064 nm and 1440 nm light; or a combination of 1064 nm and 1320 nm light; or a combination of 1440 nm, 1064 nm, and 1320 nm of light.

The following examples are a demonstration of the invention using ex vivo urinary bladders. The ex vivo urinary bladders utilized in this example were excised from healthy, adult, mixed breed pigs of both sexes purpose-bred for research. The bladders were harvested from freshly sacrificed animals by a veterinarian in the Virginia-Maryland Regional College of Veterinary Medicine. Pigs ranged from approximately 5-10 months of age.

To create a consistent curvature of the bladder wall for the experiments in this study, the ex vivo bladders were clamped at the urethra prior to inflation with 500-750 mL of isotonic phosphate buffered saline solution (PBS). Additionally, the exterior of the bladder was moistened at approximately 5 minute intervals with PBS to prevent drying of the serosa that could impact the fluid dispersal properties of the bladder.

Single-walled carbon nanohorns (SWNHs) were synthesized by the Center for Nanophase Materials Sciences at Oak Ridge National Laboratories (Oak Ridge, Tenn.) by previously described methods. The SWNHs were prepared and suspended in a 1% pluronic solution, as previously described, at a concentration of 0.05 mg/mL. A HCF was affixed within the bore of a 22 gauge needle and attached to a syringe containing SWNH solution by plastic tubing. The HCF was manually inserted with gentle pressure into the serosal layer of an inflated bladder at an angle of approximately 10° from the wall's surface, an insertion depth of 1-2 mm beneath the tissue's surface, and an inserted fiber length of 1-2 cm. The syringe was mounted in an NE-500 syringe pump (New Era Pump Systems, Inc., Farmingdale, N.Y.), and the flow rate was set to 50 µL/min. Infusion was conducted for 15 minutes for a total infused volume of 750 µL. Images were captured with an SLR camera (Canon USA, Lake Success, N.Y.) every 30 seconds starting as the syringe pump was activated. The SWNH dispersal was traced and measured using ImageJ (NIH, Bethesda, Md.) by two independent observers. Any area measurements with deviation greater than 10% were re-measured by a third observer. These experiments were conducted on two ex vivo bladders with a total of four injections.

Figure 26:
FIG. 26 is a photograph of the experimental setup for FMD infusion of SWNHs into an isolated porcine bladder.

Experiments to determine the dispersal of SWNH solution through the thickness of the bladder wall were performed by infusing SWNHs into both inflated and uninflated healthy, ex vivo bladders. An uninflated bladder was bisected from the urethra to apex and pinned open with the urothelium displayed as shown in FIG. 26. A set of infusions was made in the thin-walled tissue near the neck of the first bladder, where the needle was introduced at an angle of approximately 10° to a superficial depth (>1 mm). These infusions were made at a flow rate of 50 µL/min for 5, 10, and 15 minutes. A second set of infusions was administered in a thicker-walled section near the apex of the bladder. The HCF was introduced at the same angle, but to a deeper penetration depth (2-4 mm) near the interface of the mucosa and muscularis propria. Infusions were conducted at a flow rate of 100 µL/min for 5, 10, and 15 minutes. Following the completion of both sets of infusions, the bladder tissue was attached to a styrofoam sheet and immediately submerged in 10% neutral buffered formalin solution for fixation. Following a minimum of 24 hours of fixation, tissues were removed and trimmed for further processing. Tissues were dehydrated in a graded series of aqueous ethanols of increasing ethanol concentration, transitioned to ethanol/xylene, xylene/paraffin, and finally paraffin polymer. These dehydration and embedding procedures were done by a Tissue Tek® VIP® 6 automated tissue processing system (Sakura Finetek USA, Inc., Torrance, Calif.). Once infiltrated with paraffin polymer, three micron sections were cut, rehydrated, and then stained with hematoxylin-eosin stain, using an automated tissue stainer (Leica Microsystems, Wetzlar, Germany). A third set of infusions was conducted near the apex of an inflated bladder. The HCF fiber was inserted at the same angle as above into the serosa of the bladder to a depth of 2-3 mm. Three infusions were administered at 50 µL/min for 5, 10, and 15 minutes, respectively. Immediately after the set of infusions was completed, the bladder was drained, the infused region excised, and the removed tissue attached to a styrofoam sheet for submersion in 10% neutral buffered formalin solution. Following a minimum of 24 hours of fixation, tissues were removed and cut into thin, cross-sectional strips before being photographed with an SLR camera.

Experiments were conducted to test laser heating of infused SWNHs in the bladder wall using a 1064 nm CW diode-pumped fiber laser (IPG Photonics, Oxford, Mass.). The first experimental set was designed to determine the heating differences produced by laser irradiation of a SWNH perfused area of the bladder wall versus a non-infused control. A laser handpiece, delivering a collimated beam with a 5 mm beam width was used to irradiate the surface of the inflated bladder's serosal layer. Laser energy was delivered at an irradiance of 0.95 W/cm$^2$ for 40 seconds. Irradiation of the SWNH perfused tissue was conducted at the center of the visually detectable perfused area. Irradiation of the non-infused tissue was conducted at a similar anatomical location on the bladder wall approximately 1 cm away from the edge of the distinguishable nanoparticle perfused region. During irradiation, thermographs of the temperature distribution across the bladder's surface were recorded at 60 Hz by an A40 Thermovision infrared thermal camera (FLIR Systems, Wilsonville, Oreg.).

To determine whether the SWNHs efficacy as exogenous chromophores was independent of the Gaussian distribution of the laser beam, experiments were performed with a 1.5 cm beam width offset from the SWNH perfused bladder tissue. The ex vivo bladder was inflated and infused with SWNHs as described previously. The 5 mm collimated laser beam was expanded to a 1.5 cm beam width using an achromatic doublet lens (ThorLabs, Sterling, Va.). The laser beam spot was offset from the discernibly perfused tissue such that only a portion of the beam's periphery was irradiating that tissue. The laser irradiance was 1.1 W/cm$^2$, and thermographs were taken over 40 seconds of laser heating.

Figure 27:
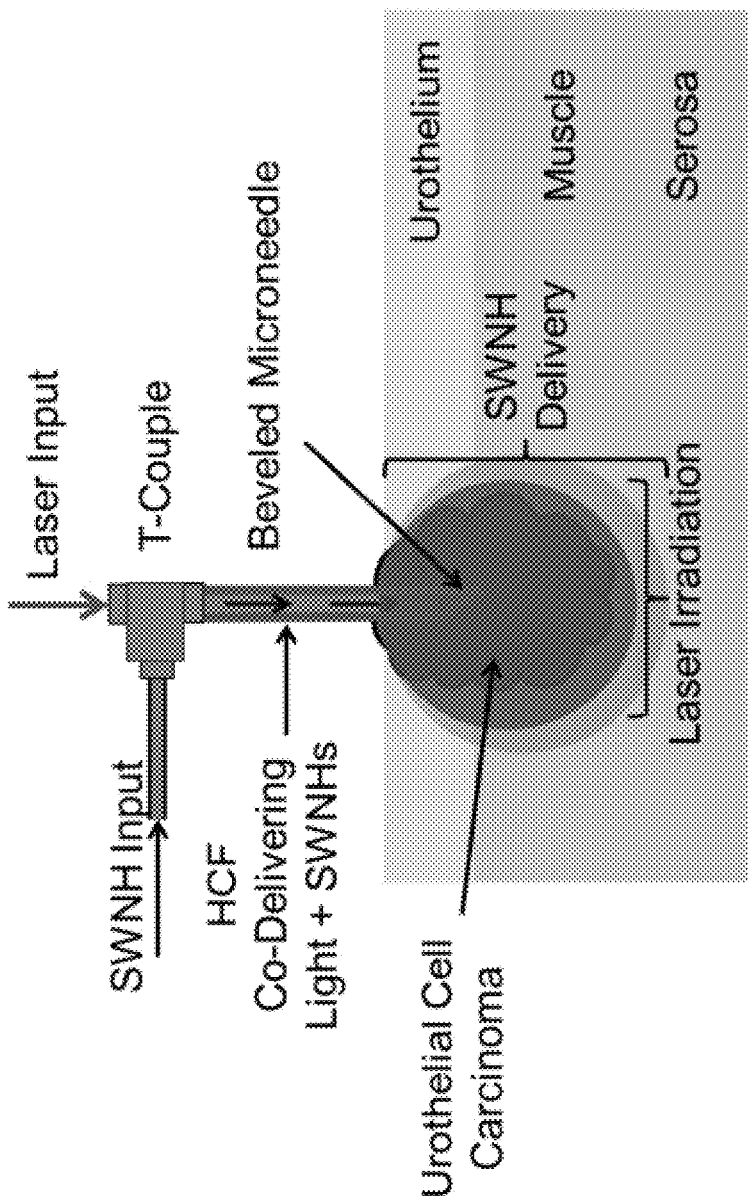
FIG. 27 is a schematic depicting the FMD design concept for bladder treatment, wherein light-guiding HCFs permit simultaneous co-delivery of laser light and fluid agents, enabling a combinatorial treatment.
Figure 28:
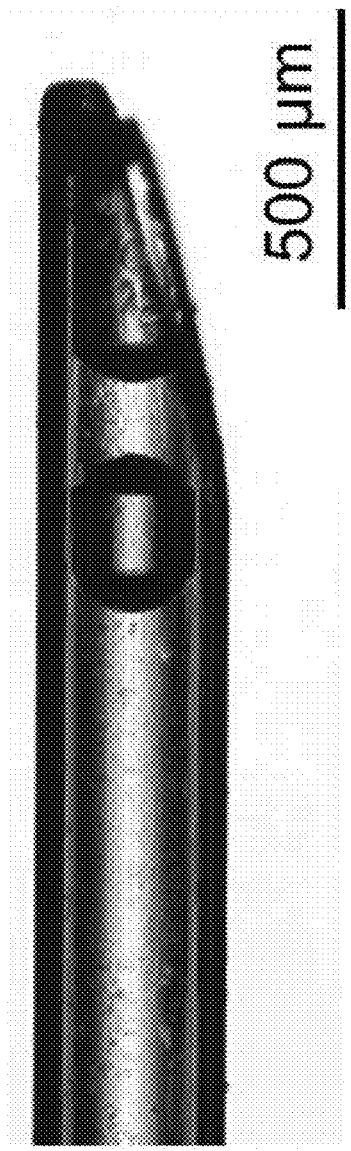
FIG. 28 is an image of a beveled microneedle showing at the tip of a hollow core fiber (HCF), wherein water is visible inside the hollow bore.

A concept depiction of this design is shown in FIG. 27. The HCF is commercially available light-guiding silica capillary tubing (365 μm outer diameter, 150 μm inner diameter, Polymicro Technologies, Phoenix, Ariz.) angle-polished at the tip to produce a sharp, beveled microneedle, shown in FIG. 28. Indeed, any size hollow core microneedle can be used, including microneedles having an outer diameter of 200-500 μm, an inner diameter of 50-450 μm, and a sharp beveled tip. Preferred microneedles can have an outer diameter ranging from 250-450 μm, or from 300-400 μm, or from 350-375 μm, with any inner diameter dimension, including from 50-400 μm, or from 75-350 μm, or from 100-300 μm, or from 150-250 μm, or from 200-225 μm. Light conduction is achieved by the principle of total internal reflection within the fused silica annular core (291 μm OD, n=1.46) by having an exterior cladding layer of doped silica (15 μm OD, n=1.44) and a fluid medium with a lower refractive index inside the inner bore.

To fabricate a prototype capable of co-delivery, the HCF was coupled with both a solid-core fiberoptic (80 μm outer diameter, 50 μm core diameter, Polymicro Technologies, Phoenix, Ariz.) and a 30 gauge syringe needle (Becton, Dickinson, Franklin Lakes, N.J.) inside a 410 μm inner bore sheath made from a 22 gauge dispensing needle (McMaster-Carr, Atlanta, Ga.). Again, the size of the solid core microneedle is not critical and can include microneedles having an outer diameter of from 25-150 μm and an inner core diameter of from 5-125 μm, such as an outer diameter of 80 μm and an inner core diameter of 50 μm, or such as an outer diameter of from 30-100 μm, or from 40-80 μm, or from 50-75 μm, or from 60-70 μm, and an inner diameter of from 5-120 μm, such as from 10-110 μm, such as from 20-90 μm, such as from 30-80 μm, such as from 40-70 μm, such as from 50-60 μm. A schematic of this co-delivery couple is shown in FIG. 29. Light from a 1064 nm laser was coupled into the 80 μm solid-core fiber using a free space to fiberoptic coupler (Newport Corporation, Irvine, Calif.). The distal end of the fiber was placed inside a 22 gauge sheath (approximately 1 cm long) simultaneously with a 30 gauge syringe needle. Once the fiber and 30 gauge needle were positioned, epoxy (Master Bond Inc., Hackensack, N.J.) was applied to the end of the sheath to hold them in place. The hollow-core fiber was aligned relative to the 80 μm fiber with a three-dimensional goniometer micropositioning stage (Opto Sigma, Santa Ana, Calif.). Coupling efficiency was determined by placing the distal end of the hollow-core fiber into an integrating sphere (Newport Corporation, Irvine, Calif.). Once a coupling efficiency of >30% was attained, the hollow-core fiber was also epoxied into the sheath. Both ends of the sheath were epoxied a second time to ensure a robust fluid seal.

Experiments demonstrating co-delivery through a single HCF were performed through sequential delivery of SWNH solution and laser light into healthy, ex vivo bladders. In embodiments, delivery of the SWNH or comparable material can be performed simultaneously with light delivery. Here, light from a 1064 nm laser was coupled into an 80 μm solid-core fiber using a free space to fiberoptic coupler. A 30 gauge needle fluid input was attached to a syringe filled with a 0.05 mg/mL SWNH solution. Pressurized flow was provided by an NE-500 syringe pump. The distal end of the co-delivery HCF was introduced into the wall of an inflated, ex vivo bladder (as described previously). HCFs were manually inserted at an angle of approximately 10° through the serosa of the inflated bladder. Insertion depths and inserted lengths varied between 1-2 mm and 1-2 cm, respectively. Infusion was conducted at 20 μL/min for 25 min, and the expanding nanoparticle perfused area was captured every 1 min with an SLR camera. After infusion was complete, the sample was irradiated with 1064 nm laser light conducted through a HCF at 400 W/cm$^2$ for 40 seconds. A control experiment irradiating a non-infused bladder wall with the same power was also performed. Thermographs of the irradiated tissue were captured via IR thermography as described previously. It is not critical the wavelength of light that is used for a particular application and those of skill in the art will know which wavelengths will be appropriate for particular therapies, especially in light of published literature to this effect.

The above examples showed that the silica HCFs were sufficiently robust to be inserted into the inflated, ex vivo bladder wall's serosa and muscularis numerous times without incurring breakage or breaching the bladder wall by overpenetration into the lumen. A representative series of time lapse images are shown below in FIGS. 30A-D.

Figure 31:
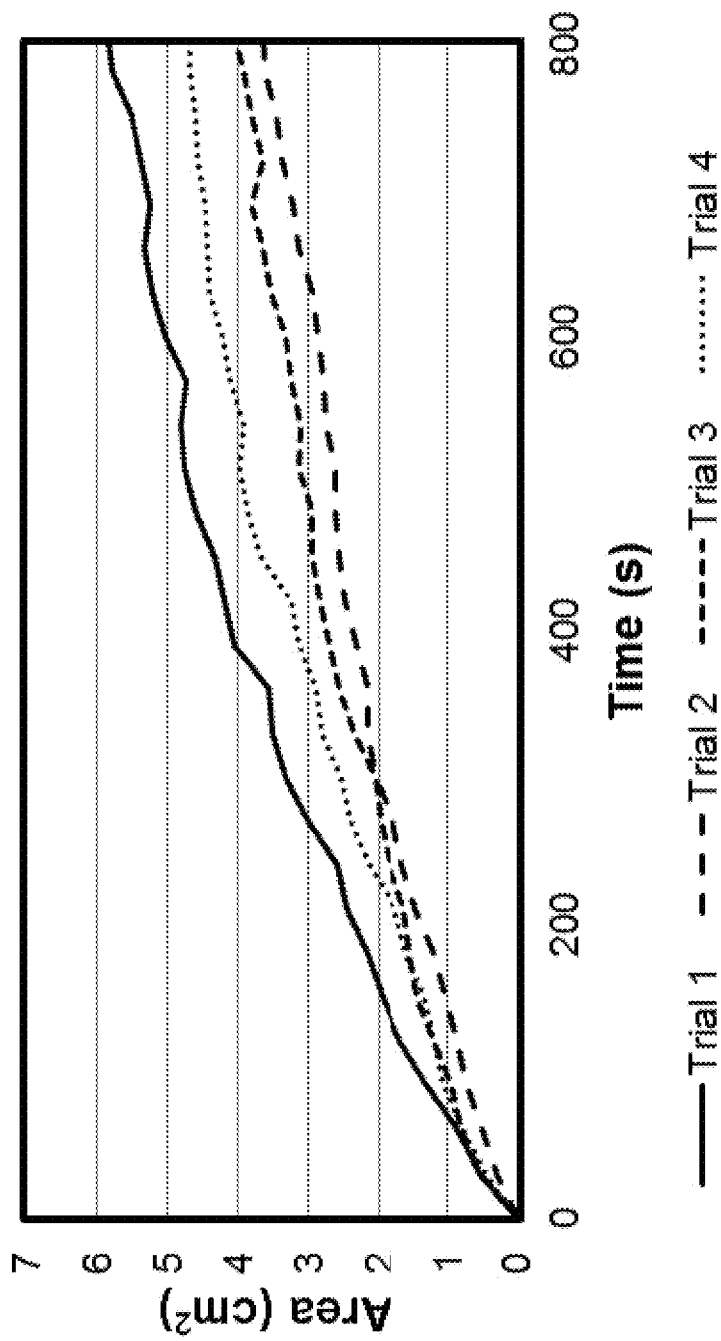
FIG. 31 is a graph showing the area versus time plot of data from the SWNH infusions into inflated bladders, wherein the SWNH area expansion across the serosa increased at a relatively linear average rate of 0.36±0.08 cm$^2$/min when infused at 50 µL/min.

SWNH area expansion across the serosa was shown to increase at a relatively linear average rate of 0.36±0.08 cm$^2$/min when infused at 50 μL/min. A graph of the average values across the 15 min experiments is shown in FIG. 31.

HCFs were placed into the bisected bladder without sustaining any damage. Reflux of fluid escaping the interstitial space by traveling along the fiber's length was dependent on flow rate. Infusions at 50 μL/min produced little to no reflux, while infusions at 100 μL/min caused obvious bolus formation and some reflux. Infusion rates can be modified and selected for particular results. Sufficient infusion rates, for example, can include infusions performed at 20 μL/min up to 200 μL/min, such as from about 30-150 μL/min, or from about 40-125 μL/min, or from about 60-90 μL/min, or from 75-85 μL/min. In particular, for treatment of other types of tissue a higher or lower flow rate may be desired.

Figure 32:
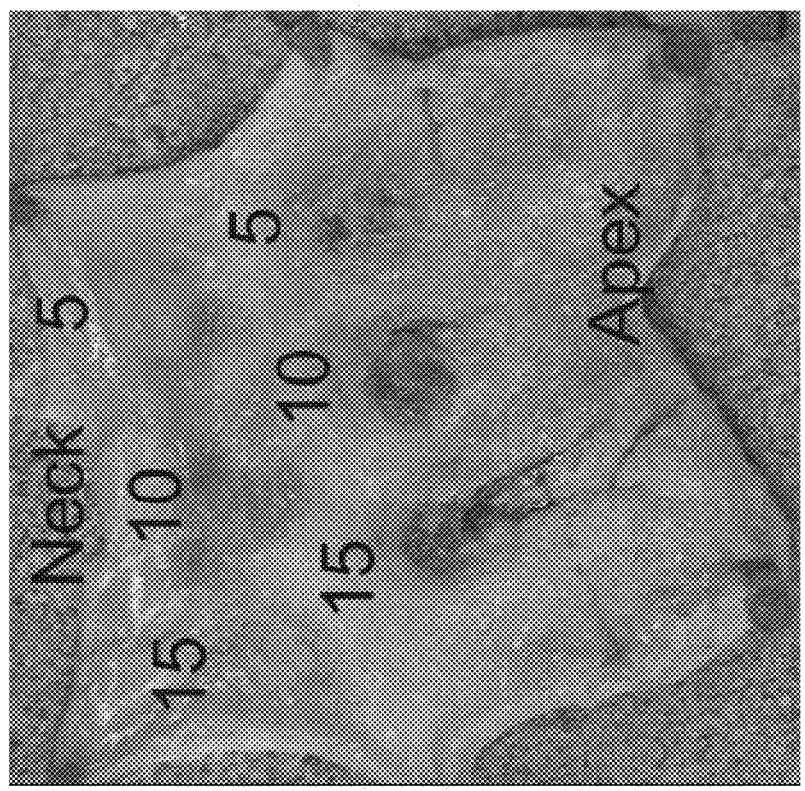
FIG. 32 is an image showing two sets of infusions, located proximal to the neck and apex of the bladder, wherein the infusion rate was 50 µL/min for the proximal infusions and 100 µL/min for the distal infusions.

A photograph of the first two sets of infusion is shown in FIG. 32. Formalin-fixed gross sections exhibited SWNH dispersal throughout the thickness of the tissue for each of the infusions near the neck of the bladder. Similar sections in thicker tissue near the bladder's apex showed SWNH dispersal through 4-5 mm of the wall's thickness. SWNH dispersal in the stained sections was evident by the expansion of the mucosal layer, which correlated highly with the localization of nanoparticles evident in the gross section from the thicker tissue shown in FIG. 33A. Fixed cross-sections from the infusion sites into the inflated bladder unanimously exhibited SWNH penetration throughout the thickness of the wall. A representative photograph is shown in FIG. 33D. The temperature increase of an inflated, ex vivo bladder wall irradiated with 1064 nm laser energy (0.95 W/cm$^2$) was measured at a region infused with SWNHs and a control region without infusion. Laser heating of a non-infused area yielded a temperature increase of approximately 5° C., while the heating of a SWNH infused area had a temperature increase of approximately 24° C. Thermographs of these results are shown in FIG. 34.

Figure 35:
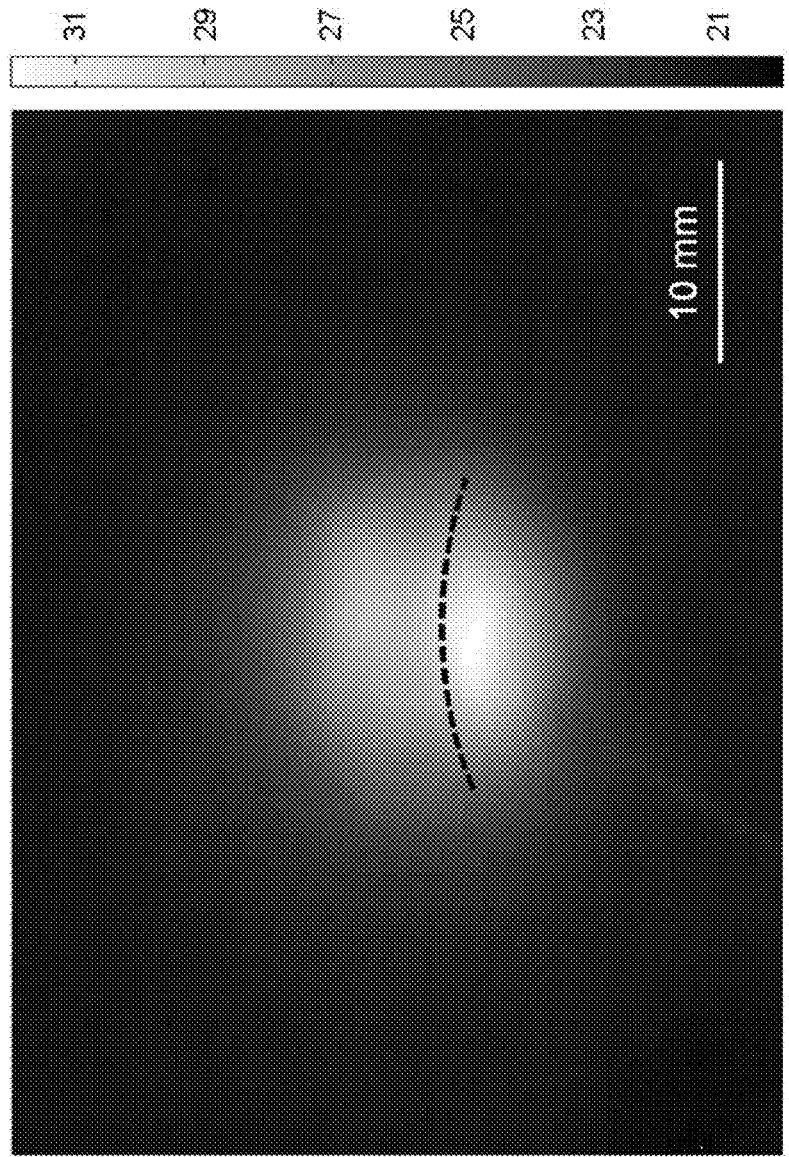
FIG. 35 depicts a thermograph of laser irradiation on SWNH perfused bladder wall with a 1.5 cm beam width, where the highest temperature correlates with the laser/SWNH overlap, the dotted line marks the top edge of the SWNH spread, and color scale is in Celsius.

Experiments utilizing an offset laser spot to heat the edge of the SWNH perfused tissue demonstrated that the significant difference in heating caused by the exogenous chromophores was independent of the Gaussian profile of the laser beam. A representative thermograph of the offset laser spot heating at an irradiance of 1.1 W/cm$^2$ for 40 seconds is shown in FIG. 35. A detectable temperature gradient was observed across the laser spot on the tissue correlating with the position of the nanoparticle spot.

Figure 36:
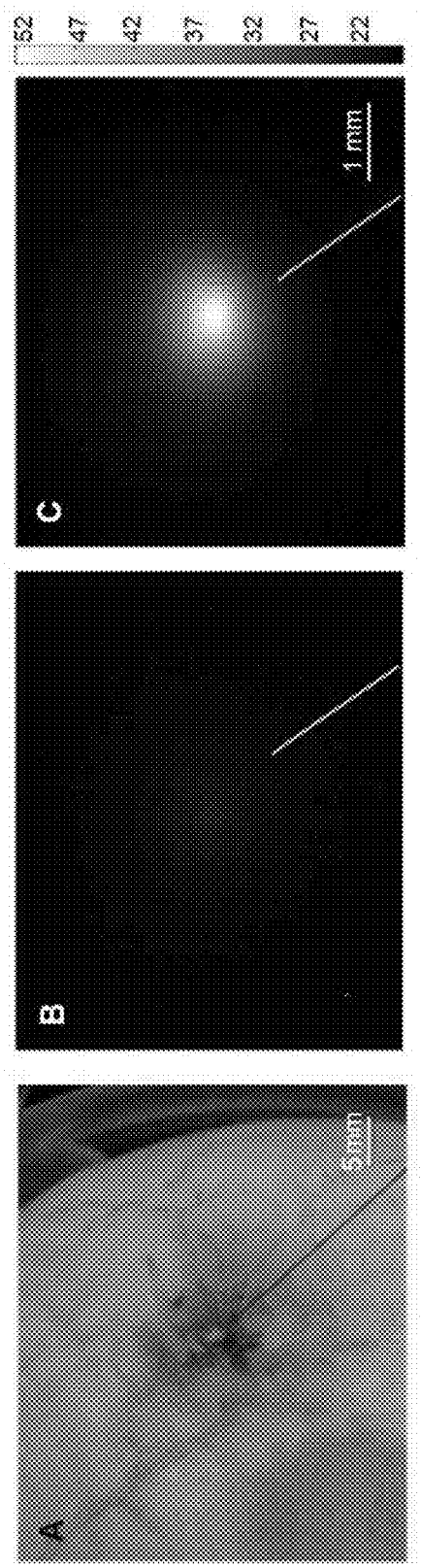

The co-delivery couple prototype had a light coupling efficiency of 35% between an 80 µm solid-core fiber and a HCF. Experiments demonstrating the feasibility of co-delivery through a single HCF exhibited a maximum temperature increase of 33° C. when irradiated at 400 W/cm$^2$ for 40 seconds. Temperature increase for non-perfused tissue at the same irradiance and time was 5° C. Representative images of the light delivery to both infused and non-infused regions of the bladder wall are shown in FIG. 36.

Therapies for Administering Doses of Diffuse Light, Including Fat Re-Shaping and Fat Reduction.

In body contouring or fat absorption embodiments of the present invention, new devices and microneedle designs are disclosed that deliver light circumferentially along, e.g., an acid-etched (cladding removed) length of about 3 mm, functioning as a microscale optical diffuser for laser therapy procedures. Light delivery in this design was evaluated with three sets of experiments described in the examples below: (i) photographic imaging of visible red light delivery onto white paper, (ii) thermal imaging of white paper irradiated with 1,064 nm CW light, and (iii) microscopic imaging of adipose tissue irradiated with 1,064 nm CW light. Excised porcine subdermal fat was used as a relevant translational model for demonstrating laser lipolysis, a potential clinical application for this tool. A flat-cleaved fiber (control) was used for comparison measurements due to the simplicity of its design and significant clinical use for mainstream laser therapy procedures. Representative devices that can be used for fat re-shaping and other techniques that are discussed in this section are shown in FIGS. 37-49.

The microneedles of the device in these embodiments may be solid or hollow fiberoptic microneedles or any combination thereof. In certain embodiments, the microneedles may be made from any light-guiding material. In some preferred embodiments, the microneedles may be made of optically transparent silica. These microneedles may be attached to one another, a housing, a guide sheath, a reservoir, a laser coupling apparatus, or any combination thereof.

The devices disclosed herein may comprise fiberoptics, sheaths, pressure regulators, reservoirs/bladders, and any combination thereof. In certain embodiments the fiberoptics may be hollow and/or solid core fiberoptics and form the central technical aspects of the disclosed device. The fiberoptics may comprise any light conducting material. In certain embodiments the light conducting material may be optically transparent silica, which has the advantages of being cheap to obtain and dependable for light transport applications. Silica fiberoptics are currently used in many medical applications and even for laser-assisted liposuction.

The disclosed device is significantly smaller/thinner than systems in use and will have applications for very precise fat removal and infusion for small volumes.

In some preferred embodiments, the device can have parallel arrays of solid core and hollow core fibers acting in concert to achieve either fat removal or fat infusion. These fibers may be employed simultaneously for a single purpose or have separate purposes, (e.g. some fibers deliver a local anesthetic). The distal end of fiber(s) may be placed within the tissue and can be coated with a drug. In embodiments, such drugs can be a local anesthetic to reduce patient discomfort, an anti-inflammatory, or cause other biological response to suit the intended purpose.

A novel feature leveraged by the device disclosed herein may be utilizing the fiber to fiber light communication and loss. The communicated light proceeds through the output fiber to where it is placed within the tissue to liquefy fat. A portion of the light that is not communicated travels down the inner bore of the hollow core fiber and may serve to continue heating liquid fat during transport through the device, which keeps the fat at a lower viscosity. In some embodiments, the fiberoptic portion of the device may be created by hand with jewelers tools or may be manufactured by an automated process that specifically positions the fiberoptics within the sheath is fairly simple to recreate.

In certain embodiments, the devices of the present invention comprise a sheath. In such embodiments, the sheath may enclose and align the fiberoptics with material that comprises any material with a heat tolerance of 125° C. The sheath may also serve to conduct heat away from the fiberoptic end-to-end coupling. A good conductor would be preferable but not mandatory.

In some embodiments, the sheath can easily be placed into an ice bath, cryogenically cooled, or associated with a similar heat sink to maintain a temperature range at the light couple that would be comfortable to a patient. The sheath can be made from an optically transparent material to limit generation from light absorption. A person of ordinary skill in the art, with the benefit of this disclosure, would know the type of material to use for the sheath. Possible materials include, but are not limited to, stainless steel, aluminum, brass, ceramic, copper, PEEK, silica, quartz, carbon fiber, and any combination thereof.

In certain embodiments, the devices of the present invention comprise a pressure regulator. Following fat liquefaction, thermal expansion of the fat volume and interstitial pressure causes the fat to enter the hollow core fiberoptic and/or sheath and flow through the device. However, this process may be aided by the inclusion of negative pressure within the fluid line transporting the liquefied fat and/or positive pressure in the tissue surrounding the liquefied fat volume. In some embodiments, pressure within the fluid line may be created by inclusion of a pump connected to the sheath either at the far end from the tissue or at a side port along the length. Alternatively, in other embodiments, a pump may be connected to a reservoir/bladder at either of those locations. This pressure may be constant, variant, or any combination thereof. In preferred embodiments, negative pressure could be utilized to aid fat removal, while positive pressure would allow fat infusion. In embodiments where positive pressure is used, positive pressure within the tissue may be caused by locally increasing the fluid pressure through mechanical pressure of the site surrounding the target fat volume or through infusion of a driving fluid local to the site. In some embodiments infusing a surfactant or fat-targeting solvent can help lower the liquefied fat's viscosity as well as increase local pressure to drive the fat.

Possible infusates for certain embodiments can include, but are not limited to, glycerol, acetic acid, diethyl ether, methyl alcohol, isopropyl alcohol, acetone, toluene, or any combination thereof.

In embodiments of the present invention, physical compression of the surrounding tissue may be accomplished through multiple means. Examples include, but are not limited to, simple pressure from a user's hands or a suction cuff connected to a pump that tightens around the area prior to liquefaction. This pressure can be constant, variant, or any combination thereof. In some embodiments, a suction cuff may be placed at the distal end of the device that can be utilized to provide positive driving pressure, be cryogenically cooled to regulate the tissue temperature surrounding the liquefaction site, or be applied with a topical anesthetic to numb an area before fat removal or infusion.

In certain embodiments, the devices of the present invention comprise a reservoir/bladder. In such embodiments, a reservoir may be attached to the sheath to collect liquefied fat or contain fat to be infused. This reservoir can be varied greatly and may include: active heating or cooling elements to aid in fat movement, containment for a fat solvent, multiple compartments, pressure pump(s), or multiple entry and exit ports. A person of ordinary skill in the art, with the benefit of this disclosure, would know what elements to include to the reservoir/bladder.

In a preferred embodiment, the reservoir would allow variable pressure and temperature control to allow removal of fat from a target tissue and re-infusion to a new location. Inclusion of a solvent may prevent fat from re-solidifying within the reservoir, allow easier cleaning, or allow the reservoir to be re-used. The reservoir may contain a drug to be mixed with the fat or infused into an area where fat has been removed. The drug could vary greatly to match application, but may include: analgesic or anti-inflammatory to relieve pain at any point before, during, or after treatment, chemotherapy, anti-inflammatories, fat reabsorption prevention, imaging markers, or any combination thereof. A person of ordinary skill in the art, with the benefit of this disclosure, will know the type of drug to use for a specific application.

In fat removal embodiments, the fiberoptic microneedle device can be used to liquefy, remove, infuse fat, or any combination thereof. Adipose tissue is made up of 80% fat and stores energy while aiding the body in maintaining thermal homeostasis, but can be considered physically unappealing. Adipose removal methods may include both mechanical and photothermal approaches. Unfortunately, these methods are limited around sensitive tissues (e.g. eyes) and are still associated with invasive probes and the need for general anesthesia. This disclosure provides devices that allow the removal of fat from sensitive areas with minimal invasiveness.

In a preferred embodiment of this disclosure, the microneedle device for fat liquefaction includes two or more optically transparent fibers, of either solid or hollow variety, communicating end-to-end (coupled) within a sheath. In such an embodiment, at least one fiber (input) may transport light from the laser to the second fiber (output) or set of fibers. The output fiber(s) may be hollow and both guides light into the target tissue to cause fat liquefaction and transports the liquid fat out of the body. An exit port(s) in the sheath immediately adjacent to where the input and output fiber(s) meet allow may allow liquefied fat to be vented.

In some embodiments, the device may include a reservoir or bladder attached to the exit port to store accumulating fat as it cools. This reservoir may employ active variable pressure to aid in drawing the fat from the tissue or infusing fat. The reservoir may also be temperature controlled to aid in both congealment of the fat and thermal stability of the laser couple. The reservoir may also contain a fat solvent, local anesthetic, drug, or any combination thereof for example.

In some embodiments, the device may include a suction device that attaches to the skin's surface during needle insertion to cause positive pressure within the tissue. This pressure may aid in the removal of the liquefied fat from the tissue. The suction device may also be cryogenically cooled to reduce patient discomfort and aid in the thermal stability of the laser couple.

In certain embodiment, the devices disclosed herein may be used in applications including: fat removal around sensitive areas (e.g. eyes), spot removal of small fatty deposits, fat liquefaction without removal, fat removal and reallocation, and any other application deemed possible by one of ordinary skill in the art with the benefit of this disclosure.

To fabricate microneedles for these examples, a novel manufacturing process was developed using acid etching, to remove cladding and core material from a multimode silica optical fiber with 105-mm core diameter and 125-mm cladding diameter, (AFS105/125Y, Fiber Guide Industries, NJ). This multimode substrate fiber is suited for transmitting 1,064 nm laser light, but can be used for delivering light at any wavelength between 630-2100 nm.

Figure 50:
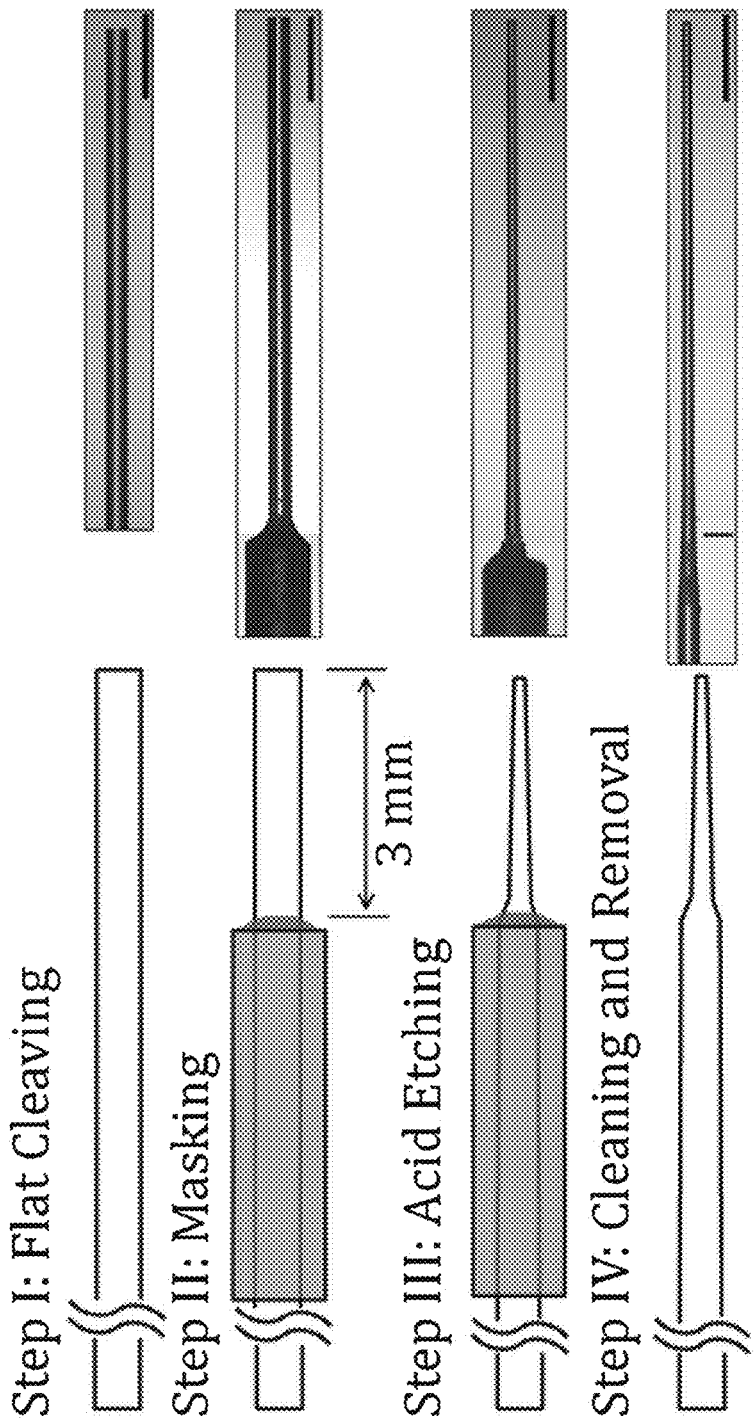
FIG. 50 is a schematic illustration of a representative fiberoptic microneedle manufacturing process disclosed in an embodiment of the present invention with a representative image from each step (500 μm scale bar).

In step I (see FIG. 50), the optical fiber was flat-cleaved at both ends to approximately 50 cm in length. In step II, one end of the fiber was housed in a capillary tube with 3 mm of fiber extending beyond the tube. The remainder of the fiber was then chemically masked inside the tube. In step III, the fiber was immersed to a depth of 3 mm in a 50% hydrofluoric (HF) acid aqueous solution (Acros Organics, Belgium). Optical fibers were etched for 10, 30, or 50 minutes with N=3 samples at each time. Etching time was varied to obtain microneedles with substantially different thick-nesses. In step 1V, the microneedles were removed from the HF solution and rinsed. In this example, the length of the microneedle can be referred to as 3 mm from base to tip, but it is recognized that it may include additional fiber optic material leading to a light source and/or may be coupled with fiber optic material to the light source.

In preferred embodiments, methods of re-shaping fat tissue can comprise inserting one or more fiber optic microneedles into fat tissue, which microneedle has a minimum outside diameter of about 25-150 µm, such as 30-70 µm, or 35-50 µm; and delivering light, at a wavelength in the range of 630-2100 nm, into the tissue for a time and under sufficient conditions to liquefy at least a portion of the fat tissue by delivery of the light at least in part circumferentially along a lateral aspect of the needle, e.g., the axial length of the needle. The minimum outside diameter refers to any point on the fiber or needle, including the base or the tip or the transitional region between the base and tip. Circumferential delivery of light refers to light radiating from the sides of the needle or fiber in a radial direction and can usually be observed along the lateral aspect of the needle, e.g., the length of the fiber, in the region between the base and the tip of the needle. As shown in the figures that follow, with increased etching of this lateral aspect of the needle, more light can escape circumferentially rather than all of the light radiating from the end or tip of the needle if no etching is removed.

Figure 51:
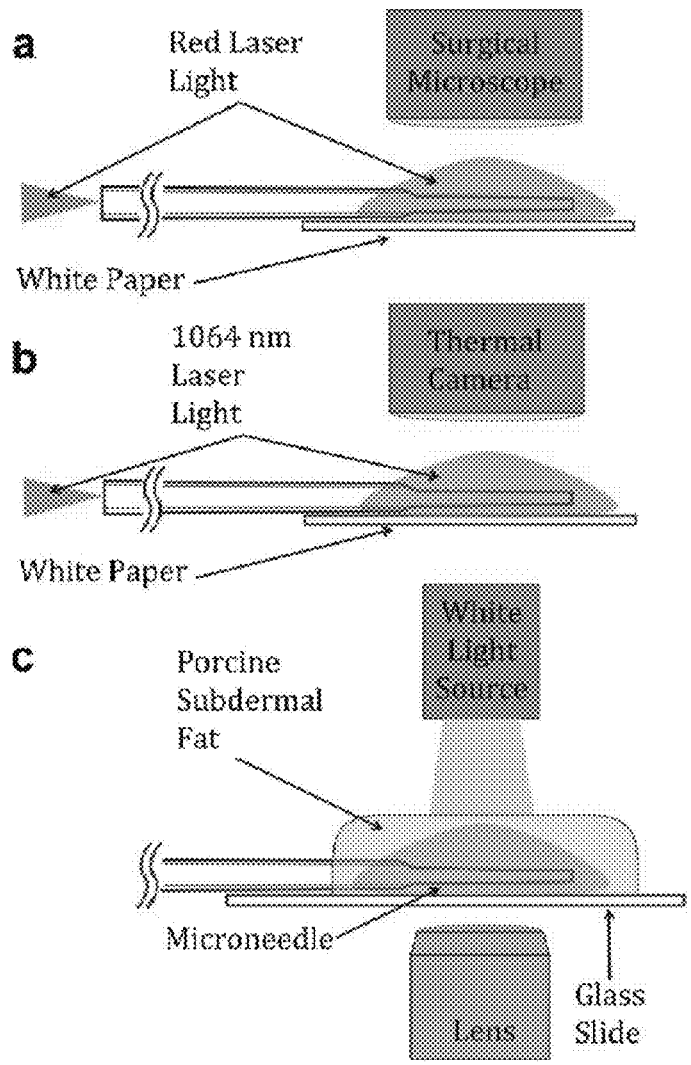
FIG. 51A is a schematic representation of microneedle light delivery and specimen interaction experiments with red light delivery/reflectance on white paper.
FIG. 51B is a schematic representation of microneedle light delivery and specimen interaction with 1,064 nm light delivery and photothermal response of white paper.
FIG. 51C is a schematic representation of microneedle light delivery and specimen interaction with 1,064 nm light delivery and structural response of adipose tissue.

Photographic imaging of visible light delivery has been used to evaluate the emission properties of optical diffusers. In this study, images of red light delivery were used to qualitatively compare the emission profiles of the different microneedles and the fiber control as shown in FIG. 51A. A free-space optical coupler (F915-T, Newport, Calif.) was used to launch collimated red light into the microneedles and the fiber control. The distal end (tip) of the fiber control and the microneedles were positioned flat on white paper. Images of the diffusely reflected light from paper were captured with a digital SLR camera (T1I, Canon USA, NY) attached to a surgical microscope (Revelation, Seiler, Mich.). The images were taken in a dark room, and the same camera exposure settings were used for each image.

Near-IR light, such as from about 750-1400 nm, delivered by fiberoptic microneedles was imaged using infrared thermography. The resultant temperature distribution of paper positioned beneath the microneedles and the fiber control experiments were com-pared. The region of paper receiving greater intensity of infrared light appeared warmer in thermography images, Continuous wave (CW), 1,064 nm light, generated by a diode-pumped fiber laser, (YLR-10-1064-LP, IPG Photonics, MA) was coupled into the microneedles and the fiber control in the manner described above for visible light delivery experiments (FIG. 51B). Total power delivered in all directions from each microneedle was measured using an integrating sphere (819C-OPT, Newport) with a silicon photodetector (918D-SL-OD1, Newport). Microneedles were positioned flat on white paper and a power of P=1 W was delivered. A thermal camera (Thermovision A40M, FLIR, MA) was used to image the temperature distribution around the microneedle and the fiber control during laser irradiation. The emissivity of the white paper (0.9) and the ambient temperature (293 K) were measured and factored into data analysis. The thermal camera was equipped with a focusing lens (Close-up lens LW 34/80, FLIR), and the resulting spatial resolution was 83 mm per pixel. The image-recording rate was 1 Hz.

Excised porcine abdominal belly skin, from young adult hogs, was acquired from a local abattoir. Subdermal fat specimens of 1-2 mm in thickness were prepared. To maintain hydration prior to the experiments, samples were placed between paper cloths saturated with isotonic saline and maintained at 4 degrees Celsius. The fiberoptic microneedles were placed on a glass slide, and the fat samples were placed over the microneedles. Fat samples were irradiated with 1,064 nm light for 60 seconds with P=5 W of power delivered by microneedles and the fiber control. Any length of time may be used that is sufficient to liquefy fat tissue and may be dependent on the actual wavelength of light used. For example, energy may be delivered into the tissue for 1 second, 5 seconds, 10 seconds, 30 seconds, and so on up to about 1 min., 2 min., 3 min., 4 min. or 5 min. Indeed any known fat liquefying or skin tightening protocol may be used in conjunction with the microneedle devices of the present invention. The conditions sufficient to achieve a particular result may also be modified according to those particular needs. For example, it may be desired to administer the light in a pulsed protocol, or alternate between one or more different intensities of light. It may be desirable to keep local temperature of the tissue and/or needle below 100° C., or higher temperatures may be desired, such as above 100° C., for some procedures.

Bright field imaging (DM IL LED; Leica Microsystems, Switzerland) was used to capture images of fat liquefaction, which was indicated by the disruption of adipocytes. Carbonization (charring) of the tissue around the microneedles and the fiber control was considered an indication that the local temperature of the tissue/needles exceeded 100° C. Pre- and post-experimental images of the microneedles were compared and any carbonization of the tissue was noted in Table 1 below. A schematic illustration of the experimental setup is given in FIG. 51C.

TABLE 1

Geometric Parameters of Microneedles

| Microneedles | Etching time (minutes) | Length (mm) | Average thickness (μm) | Tip thickness (μm) | Carbonization observed? |
|---|---|---|---|---|---|
| Control | n/a | n/a | 125 | 125 | yes |
| 10-I, 10-II, 10-III | 10 | 2.9, 3.0, 3.0 | 99, 98, 97 | 92, 95, 95 | yes |
| 30-I, 30-II, 30-III | 30 | 3.0, 2.7, 2.7 | 72, 70, 68 | 59, 65, 60 | yes |
| 50-I, 50-II, 50-III | 50 | 3.0, 2.9, 2.8 | 48, 38, 33 | 21, 20, 17 | No, no, yes |

Figure 52:
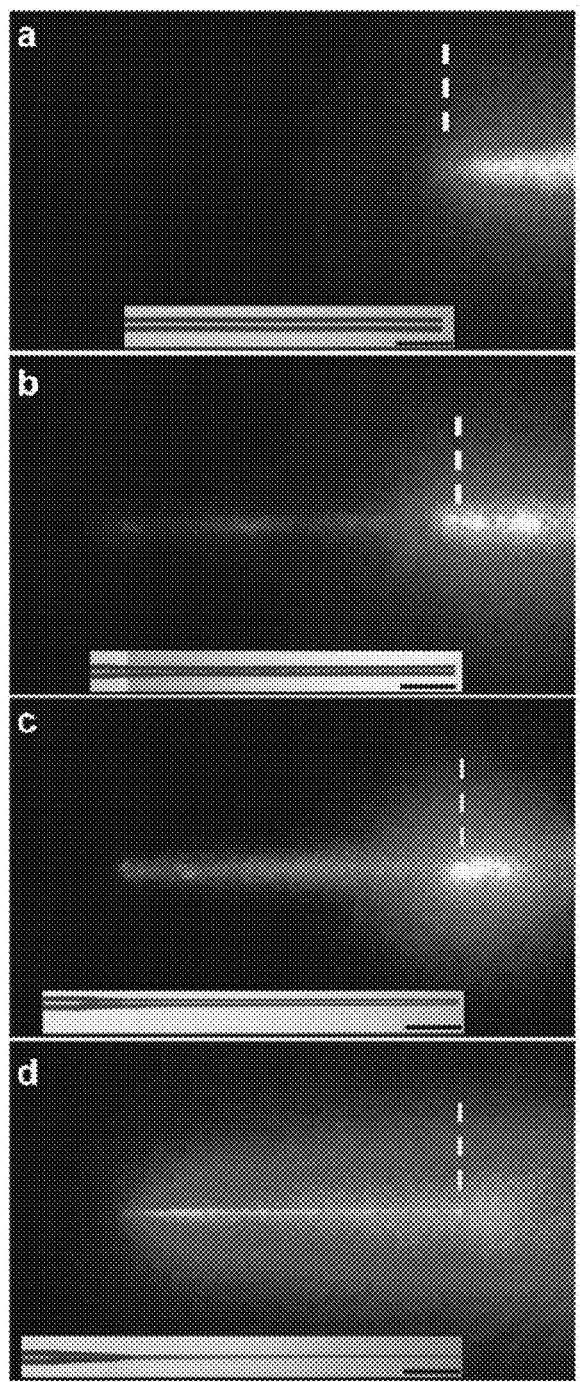
FIG. 52A is an image depicting the diffuse reflectance of red light from white paper during delivery by a control.
FIG. 52B is an image depicting the diffuse reflectance of red light from white paper during delivery by 10-I.
FIG. 52C is an image depicting the diffuse reflectance of red light from white paper during delivery by 30-I.
FIG. 52D is an image depicting the diffuse reflectance of red light from white paper during delivery by 50-III (500-μm scale bar).

Representative red light delivery images of microneedles and the fiber control are shown in FIG. 52. The bright field microscopy images of the microneedles and the fiber control are shown beneath each light delivery image with the same position and magnification. For the fiber control, all of the visible light was delivered from the flat end face (FIG. 52A). Thus, the fiber was not visible in this image. After leaving the tip, the light diverged in a conical beam as theoretically predicted, based on the numerical aperture (NA=0.22) of the fiber.

A representative microneedle is shown for each etching time of 10, 30, and 50 minutes in FIG. 52 B,C,D respectively. For all the microneedles, visible light was emitted from the circumference, rendering them visible. As the etching time was increased, a larger region of diffuse reflection from the underlying white paper was formed around the microneedles, and the area of the spot of saturated intensity near the tip was reduced.

Figure 53:
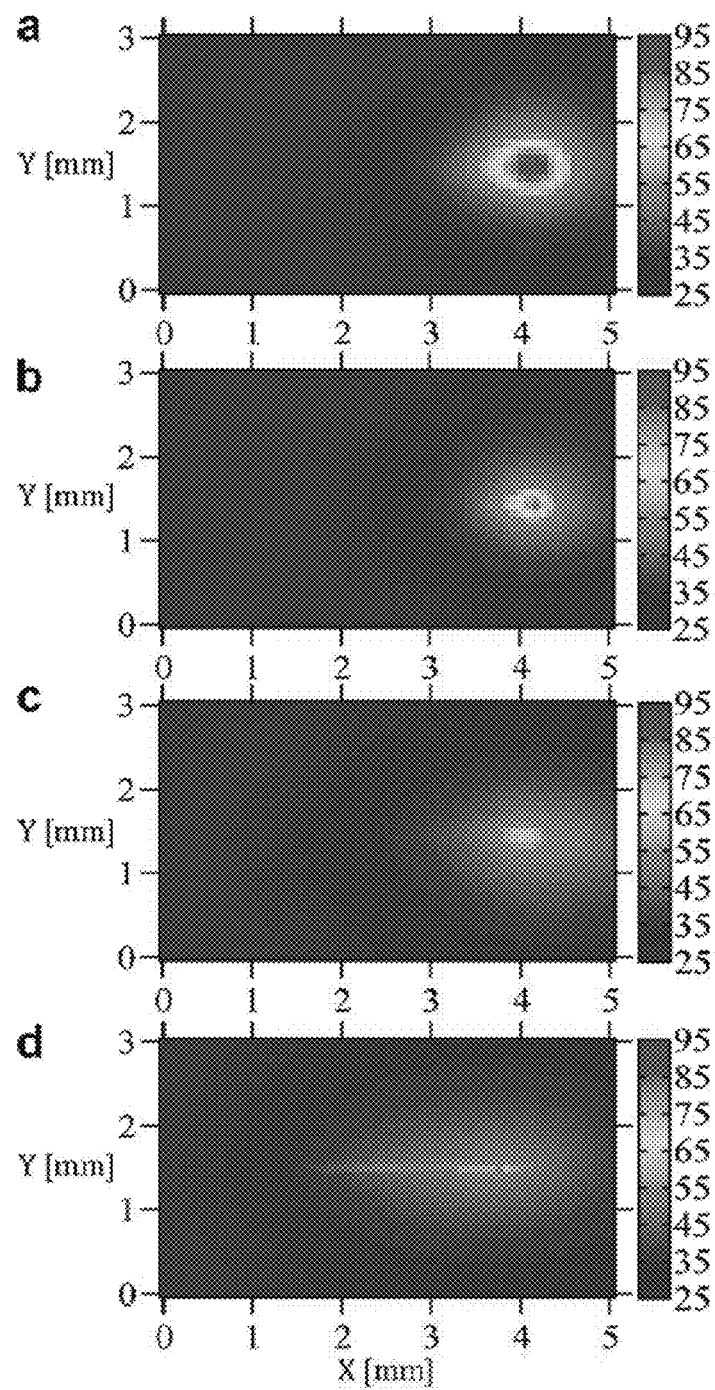
FIG. 53A is a thermograph depicting the temperature distribution after 15 seconds of irradiation (1,064 nm, P=1 W) for the control.
FIG. 53B is a thermograph depicting the temperature distribution after 15 seconds of irradiation (1,064 nm, P=1 W) for the 10-I.
FIG. 53C is a thermograph depicting the temperature distribution after 15 seconds of irradiation (1,064 nm, P=1 W) for the 30-I.
FIG. 53D is a thermograph depicting the temperature distribution after 15 seconds of irradiation (1,064 nm, P=1 W) for the 50-III.

The temperature distribution of the paper beneath the microneedles and the fiber control following 15 seconds of irradiation with 1,064 nm light (P=1 W) are shown in FIG. 53. The tip of each microneedle and the fiber control were positioned at x=4 mm and y=1.5 mm in each image. In FIG. 53, the region of higher temperature extended from the tip towards the base of the microneedle as the etching time was increased from zero (control, FIG. 53A) to 50 minutes (50-III, FIG. 53D).

Figure 54:
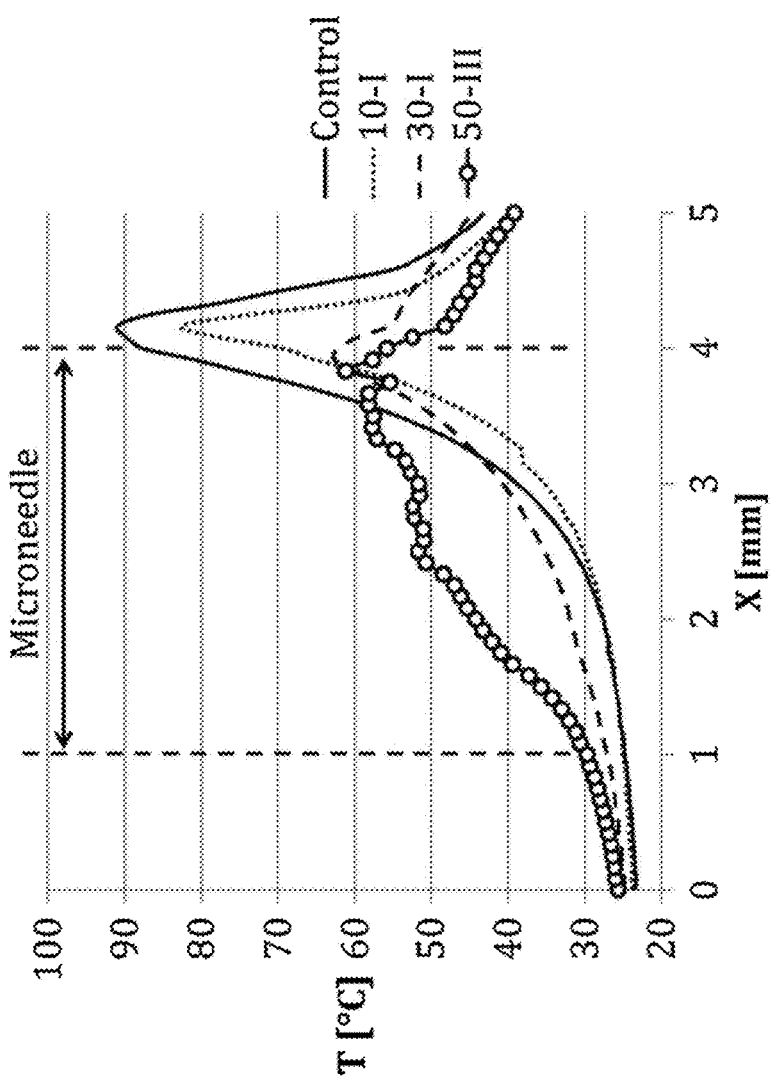
FIG. 54 is a graphical representation of the local temperature along the axes of the microneedles and the control fiber after 15 seconds of irradiation (1,064 nm, P=1 W).

To allow quantitative assessment of the 1,064 nm light delivery and resultant heat generation in the paper, the local temperature along the axes of the microneedles and the fiber control following 15 seconds of irradiation with 1,064 nm light (P=1 W) are plotted in FIG. 54. Axial temperature profiles in FIG. 54 demonstrate that as the etching time was increased the light was delivered more uniformly through the length of the microneedles. As a result, while light delivery by the control generated a large temperature peak right in front of the tip (x=4.1 mm), light delivery by 50-III generated relatively uniform temperatures along the length of the microneedle (x=1-4 mm).

Figure 55:
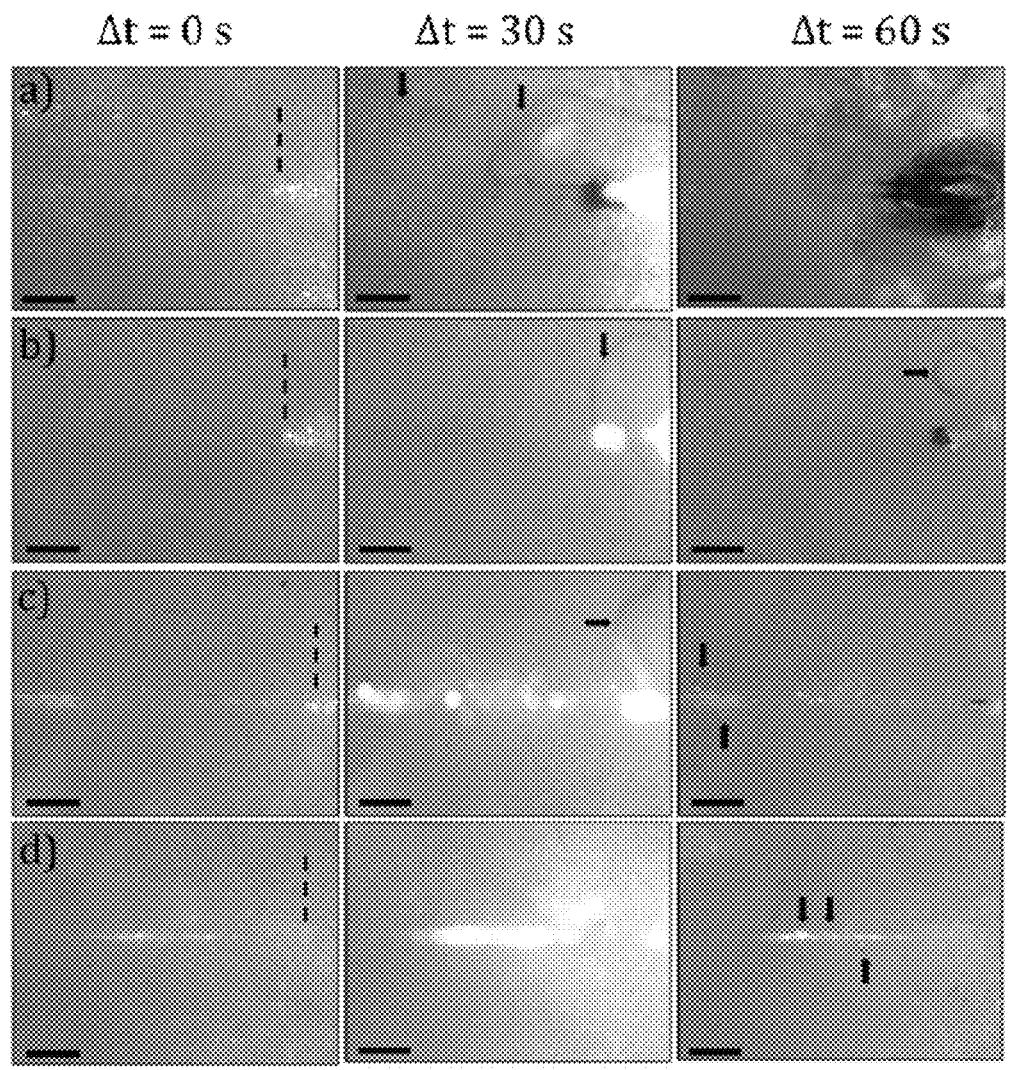
FIGS. 55A-D are photographs of the adipose tissue before, during, and after 1,064 nm, P=5 W irradiation for 60 seconds, where

A representative image for light delivery experiments conducted in adipose tissue with the microneedles of different etching times and fiber control are shown in FIG. 55. In the pre-irradiation images, (duration of laser irradiation, Dt=0 second), microneedles and the fiber control were delivering red laser light and individual adipocytes were visible. In these images, microneedle tips are marked with dashed lines.

Images captured during laser irradiation (Dt=30 seconds) show microneedles and the fiber control delivering 1,064 nm light (P=5 W), which saturated the camera. Post-experimental images (Dt=60 seconds) show disruption of adipocytes and carbonization of the tissue. Pools of liquefied fat (marked by arrows) were observed in all post-experimental images. Decreased microneedle diameter was correlated with decreased incidence of tissue and fiber tip carbonization (Table 1). All of the microneedles were intact following experimentation with the exception of 50-III that was severed at its base.

The qualitative observations obtained from the light delivery images were quantitatively supported by thermal imaging experiments. As the microneedle thickness decreased, more diffuse light delivery resulted in lower maximum temperatures (FIG. 55). Microneedles that were etched longer, such as 50-III, generated an increased and more uniform region of heating along their lengths (FIG. 54), which may be preferable for many photothermal therapy applications.

Fat irradiation experimental results highlighted several differences between the fiber control and microneedles of different thicknesses. First, the region of disrupted adipocytes shifted away from the tip (FIG. 55A) and towards the mid-length of the microneedle (FIG. 55D) as the microneedle thickness decreased. This is expected as more light was emitted prior to the tip with thinner microneedles. Secondly, the amount of carbonized tissue diminished with decreasing thickness. Minimizing carbonization is important in some applications, as carbonization of the tissue can have detrimental effects on the efficiency of laser photothermal therapy by limiting light propagation inside the tissue and visibility during surgery. Carbonized tissue can cover the surface of the microneedle, causing the local temperature around the microneedle to become extremely high, leading to more carbonization, and eventual failure.

The fiberoptic microneedles delivered light through a larger, circumferential surface area as opposed to the flat-cleaved fiber, which delivers light through the smaller, cross-sectional area of its core. The fiber control carbonized the tissue when delivering P=5 W through its 105 mm diameter core (Ir=577 W/mm$^2$). In contrast, the light delivery surface area of microneedle 50-H during fat liquefaction experiments was ~0.35 mm2 (obtained by approximating the microneedle as a cylinder). This microneedle was able to deliver P=5 W with a spatially averaged irradiance of Ir=14 W/mm$^2$ without causing any carbonization. Increasing the surface area available for light emission from a microneedle optical diffuser can reduce undesirable effects of high irradiance while still delivering high energy or power dose.

These results indicate that thinner microneedles (33-48 mm) are favorable for light delivery properties. Due to their slenderness, these microneedles can be damaged while being inserted into organs such as skin. Here, microneedle 50-III was damaged while liquefying fat. Mechanical damage caused the light-diffusing surface to reduce drastically and caused carbonization of the tissue. To address this issue, certain embodiments may use a microneedle insertion device, which can be used to mechanically strengthen the microneedles by limiting their unsupported length during insertion into tissue. Such ferrules can include known techniques in the art as well as the specific ferrules described in this specification.

The present invention has been described with reference to particular embodiments having various features. It will be apparent to those skilled in the art that various modifications and variations can be made in the practice of the present invention without departing from the scope or spirit of the invention. Indeed, numerous references have been cited in this specification to provide background about the current state of the art and to provide context to the present invention. These cited references can be used by those skilled in the art to supplement this disclosure. To this extent, all of the references cited in this specification are hereby incorporated by reference herein in their entireties to form part of the disclosure of the preferred embodiments of the present invention. For example, any of the desired properties or characteristics indicated in the cited references for desired fiber optic needles or materials used for such needles can be the desired properties of needles and devices of the present invention.

Further, one skilled in the art will recognize that the features of embodiments of the invention may be used singularly or in any combination based on the requirements and specifications of a given application or design, and one or more elements, constituents, or process steps may be omitted, incorporated, or altered as desired. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. It should be evident that the particular illustrative embodiments disclosed above may be altered or modified and all such variations are considered within the scope and spirit of the present invention. While compositions, devices, and methods are described in terms of "comprising," "containing," or "including" various components or steps, these facets of the invention can also "consist essentially of" or "consist of" the various components and steps.

All numbers and ranges disclosed in this specification, including the claims, may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:
1. A microneedle device comprising:
   one or more hollow core optical fiber microneedle having a core capable of conducting fluid and a tip adapted for piercing human tissue;
   a light source;
   and one or more solid core optical fiber;

wherein the light source and the solid core optical fiber are together disposed in a manner to deliver light into and through the hollow core optical fiber microneedle;

one or more fluid pump and one or more fluid reservoir disposed in a manner to facilitate aspiration of and delivery of fluids;

wherein the device is adapted to aspirate fluid into and to deliver fluid out through the tip and core of the hollow core optical fiber microneedle.

2. The microneedle device of claim 1, wherein the tip is sharp, sharpened, tapered, angled, polished, or beveled.

3. The microneedle device of claim 1 wherein the one or more solid core optical fiber is disposed in communication with the hollow core optical fiber microneedle in a manner to allow light to pass from the solid core optical fiber to the hollow core optical fiber microneedle during use.

4. The microneedle device of claim 3, wherein the solid core optical fiber and the hollow core optical fiber microneedle each have ends disposed facing one another.

5. The microneedle device of claim 4, wherein the end of the solid core optical fiber and the end of the hollow core optical fiber microneedle contact one another.

6. The microneedle device of claim 4, wherein the end of the solid core optical fiber and the end of the hollow core optical fiber microneedle do not contact one another.

7. The microneedle device of claim 1 comprising an outlet in the sheath for removing liquid from the sheath during use.

8. The microneedle device of claim 1, wherein the hollow core optical fiber microneedle has an outside diameter in the range of about 50 μm to 500 μm.

9. The microneedle device of claim 1 comprising an inlet for delivering a fluid agent chosen from an anesthetic or anti-inflammatory agent.

10. The microneedle device of claim 1, further comprising:

an elongated outer sheath with a wall defining a first lumen; and wherein the hollow core optical fiber microneedle is disposed within the first lumen and provides a wall defining a second lumen;

wherein the light source and the solid core optical fiber are disposed in a manner to deliver light into and through the wall of the hollow core optical fiber microneedle; and wherein the microneedle device is adapted to aspirate fluid into and deliver fluid out through the second lumen.

11. The microneedle device of claim 1, wherein the light source and the solid core optical fiber are together disposed in a manner to deliver light into and through a wall of the hollow core optical fiber microneedle which surrounds the core capable of conducting fluid.

12. The microneedle device of claim 1, wherein the solid core optical fiber is coupled with the hollow core optical fiber microneedle to deliver light from the light source at a coupling efficiency greater than 30%.

13. The microneedle device of claim 1, wherein the solid core optical fiber is coupled with the hollow core optical fiber microneedle to deliver light from the light source such that the wavelength of emitted light is the same as the wavelength of the light source.

* * * * *